(12) United States Patent
Morgan et al.

(10) Patent No.: US 7,763,612 B2
(45) Date of Patent: Jul. 27, 2010

(54) THERAPEUTIC AMINE-ARYLSULFONAMIDE CONJUGATE COMPOUNDS

(75) Inventors: Philip F. Morgan, Cary, NC (US); James L. Kelley, Raleigh, NC (US)

(73) Assignee: Algebra, Inc., Cary, NC (US)

( * ) Notice: Subject to any disclaimer, the term of this patent is extended or adjusted under 35 U.S.C. 154(b) by 852 days.

(21) Appl. No.: 11/619,291

(22) Filed: Jan. 3, 2007

(65) Prior Publication Data

US 2007/0155729 A1 Jul. 5, 2007

Related U.S. Application Data

(60) Provisional application No. 60/755,923, filed on Jan. 3, 2006.

(51) Int. Cl.
*A61K 31/5377* (2006.01)
*C07D 413/12* (2006.01)

(52) U.S. Cl. ............ 514/231.5; 514/217; 514/444; 514/471; 540/522; 544/152; 546/197; 549/60; 549/467; 549/494

(58) Field of Classification Search ............ 540/522; 544/152; 546/197; 549/60, 467, 494; 514/217, 514/231.5, 444, 471
See application file for complete search history.

(56) References Cited

U.S. PATENT DOCUMENTS

| | | | |
|---|---|---|---|
| 3,819,706 A | 6/1974 | Mehta | |
| 3,885,046 A | 5/1975 | Mehta | |
| 4,356,165 A | 10/1982 | Findlay et al. | |
| 4,495,180 A | 1/1985 | Alexander | |
| 5,104,870 A | 4/1992 | Kelley et al. | |
| 6,051,576 A | 4/2000 | Ashton et al. | |
| 6,274,579 B1 | 8/2001 | Morgan et al. | |
| 6,391,875 B2 | 5/2002 | Morgan et al. | |
| 2002/0142955 A1 | 10/2002 | DuBois et al. | |
| 2004/0214804 A1 | 10/2004 | Gulve et al. | |
| 2005/0008695 A1 | 1/2005 | Ashton et al. | |
| 2005/0014786 A1 | 1/2005 | Sun et al. | |
| 2005/0043332 A1 | 2/2005 | Castelhano et al. | |
| 2005/0187280 A1 | 8/2005 | Minnich et al. | |

OTHER PUBLICATIONS

Ahmad, et al., "Controlled trial of frusemide as an antiepileptic drug in focal epilepsy", Br. J. Clin. Pharmac. 1976, p. 621-25 vol. 3.
Alexander, J. et al., "(Acyloxy)alkyl Carbamates as Novel Bioreversible Prodrugs for Amines: Increased Permeation through Biological Membranes", J. Med. Chem., 1988, p. 318-322, vol. 31.
Bodor, Nicholas, "Soft Drugs. 1. Labile Quaternary Ammonium Salts as Soft Antimicrobials", J. Med. Chem., 1980, p. 469-474, vol. 23.
Boswell, G. Evan, et al., "Synthesis and Anti-tetrabenazine Activity of C-3 analogues of Dimethyl-2-phenylmorpholines", J. Heterocyclic Chem., 1996, p. 33-39, vol. 33.

Bundgaard, Hans, "Novel chemical approaches in prodrug design", Drugs of the Future, 1991, p. 443-458, vol. 16(5).
Cooper, Barrett, R., et al., "Animal Models Used in Prediction of Antidepressant Effects in Man", J. Clin. Psychiatry, 1983, p. 63-66, vol. 44:5(Sec. 2).
Crooks, P., et al., "Synthetic Strategies for the Preparation of "Gemini" Codrugs of Naltrexone, and Heterocodrugs of &[beta]-Naltrexol with Hydroxybupropion for Transdermal Delivery", 2005 AAPS Annual Meeting and Exposition Nov. 5, 2005-Nov. 10, 2005, Abstract.
Folkmann, Michael, et al., "Acyloxymethyl Carbonochloridates. New Intermediates in Prodrug Synthesis", Synthesis, Dec. 1990, p. 1159-1166.
Greene, Theodora, et al., Protective Groups in Organic Synthesis, 1991, p. 240.
Greene, Theodora, et al., Protective Groups in Organic Synthesis, 1991, p. 232.
Greene, Theodora, et al., Protective Groups in Organic Synthesis, 1991, p. 228.
Kelley, James L., et al., "(2S,3S,5R)-2-(3,5-Difluoropenyl)-3,5-dimethyl-2-morpholinol: A Novel Antidepressant Agent and Selective Inhibitor of Norepinephrine Uptake", J. Med Chem., 1996, p. 347-349, vol. 39.

(Continued)

*Primary Examiner*—Bernard Dentz
(74) *Attorney, Agent, or Firm*—Christopher J. Knors; Moore & Van Allen PLLC

(57) ABSTRACT

Therapeutic amine-arylsulfonamide conjugate compounds, of the general formula:

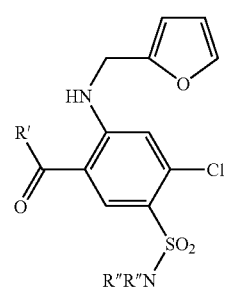

(I)

wherein
R' is [D-W-], hydroxyl, or alkoxyl;
R" is independently [D-W'-], hydrogen, alkoxy, alkyl, cycloalkyl, alkenyl, alkynyl or aryl, or R" and R" together with the nitrogen atom to which they are attached form a 4-, 5-, 6-, 7- or 8-membered ring optionally containing one or two further heteroatoms independently selected from nitrogen, oxygen and sulfur;
D is independently a therapeutic amine radical comprising at least one nitrogen atom and optionally at least one oxygen atom coupled to W or W' by a nitrogen or oxygen atom;
W and W' are a chemical bond or linker;
wherein either R' is [D-W-] or at least one R" is [D-W'-], and pharmaceutically acceptable esters, amides, salts or solvates thereof, pharmaceutical compositions containing same, methods for their preparation, and their use in treating psychiatric, neurologic and metabolic disorders are disclosed.

16 Claims, No Drawings

OTHER PUBLICATIONS

Lüddens, Hartmut, et al., "Structure—activity relationship of furosemide-derived compounds as antagonists of cerebellum-specific $GABA_A$ receptors", Eur. J. Pharmacol., 1998, p. 269-277, vol. 344.

Mendes, Eduarda, et al., "Synthesis, Stability and In Vitro Dermal Evaluation of Aminocarbonyloxymethyl Esters as Prodrugs of Carboxylic Acid Agents", Bioorganic & Medicinal Chemistry, 2002, p. 809-816, vol. 10.

Musso, David L., et al., "Design and Synthesis of a Chiral Hapten for a Radioimmunoassay of the Antidepressant (2S, 3S, 5R)-2-(3,5-Difluorophenyl)-3,5-dimethyl-2-morpholinol Hydrochloride", Tetrahedron: Assymetry, 1995, p. 1841-1844, vol. 6.

Musso, David L., et al., "Indanylidenes. 2. Design and Synthesis of (E)-2-(4-Chloro-6-fluoro-1-indanylidene)-N-methylacetamide, a Potent Antiinflammatory and Analgesic Agent without Centrally Acting Muscle Relaxant Activity", J. Med. Chem, 2003, p. 409-416, vol. 46.

Patonay, Tamás, et al., "α-Haloalkyl Haloformates and Related Compounds 1. A Convenient Synthesis of Carbamates *Via* Chloromethyl Carbonates", Synthetic Communications, 1990, p. 2865-2885, vol. 20(18).

Pitman, Ian H., "Pro-Drugs of Amides, Imides, and Amines", Medicinal Research Reviews, 1981, p. 189-214, vol. 1.

Rasmusson, Gary H., et al., "2-Cyclopentene-1,4-Dione", Organic Syntheses, 1973, p. 324-325, vol. 5.

Sandler, Stanley R., et al., "*Preparation of 4-Methylcyclohexanone* [14]", Organic Functional Group Preparations, 1968, p. 171.

Sandler, Stanley R., et al., "*Preparation of N-tert-Butylbenzylamine* [8]", Organic Functional Group Preparations, 1968, p. 324.

Sandler, Stanley R., et al., "*Preparation of Methyl Acetate* [1]", Organic Functional Group Preparations, 1968, p. 249.

Schlatter, E. et al., "Effect of "High Ceiling" Diuretics on Active Salt Transport in the Cortical Thick Ascending Limb of Henle's Loop of Rabbit Kidney", Pflügers Arch., 1983, p. 210-217, vol. 396.

Shani, J., et al., "Structure Activity Correlation for Diuretic Furosemide Congeners", Pharmacology, 1983, p. 172-180, vol. 26.

Yamaoka, Yumiko et al., "Low-Melting Phenytoin Prodrugs as Alternative Oral Delivery Modes for Phenytoin: A Model for Other High-Melting Sparingly Water-Soluble Drugs", Journal of Pharmaceutical Sciences, Apr. 1983, p. 400-405, vol. 72, No. 4.

THERAPEUTIC AMINE-ARYLSULFONAMIDE CONJUGATE COMPOUNDS

CROSS-REFERENCE TO RELATED APPLICATION

This application claims benefit of U.S. Provisional Patent Application No. 60/755,923, filed Jan. 3, 2006, which is incorporated herein by reference in its entirety.

FIELD

Therapeutic amines conjugated to arylsulfonamides, their pharmaceutical compositions, methods of making, and methods of using same are provided.

BACKGROUND

A number of therapeutic amine compounds have been developed for the treatment of psychiatric, neurologic and metabolic disorders including, but not limited to, depression, obesity, fibromyalgia, neuropathic pain, restless leg syndrome, attention deficit hyperactivity disorder (ADHD), migraine, pain, sexual dysfunction, Parkinson's disease, Alzheimer's disease, anxiety, narcolepsy-cataplexy syndrome, seizures or drug/substance addiction/cessation. These include bupropion hydrochloride salt, [1-(3-chlorophenyl)-2-[(1,1-dimethylethyl)amino]-1-propanone.HCl] which is the active ingredient of WELLBUTRIN®. It is marketed in the United States for the treatment of depression. Bupropion hydrochloride is also the active ingredient of ZYBAN®, which is marketed in the United States as an aid to smoking cessation.

The compound (+)-(2S,3S)-2-(3-chlorophenyl)-3,5,5-trimethyl-2-morpholinol hydrochloride salt, which is an active metabolite of bupropion hydrochloride, is the active ingredient of radafaxine, and is proposed for the treatment of depression, obesity and other conditions. (U.S. Pat. No. 6,274,579 and U.S. Pat. No. 6,391,875). Another therapeutic amine compound, for example, (2S,3S,5R)-2-(3,5-difluorophenyl)-3,5-dimethyl-2-morpholinol, the active ingredient of manifaxine, has been proposed for the treatment of depression, among other ailments (U.S. Pat. No. 5,104,870).

Bupropion, however, is known to cause seizures in high therapeutic doses (Harris, et al., Fatal bupropion overdose, *J. Toxicol. Clin Toxicol.* (1997) 35: 321-4; Kuate, et al., A. Bupropion-induced epileptic seizures, *Rev. Neurol.* (2004), 160: 701-3.) Several therapeutic amines, including bupropion and radafaxine, are known to elicit seizures in animals (U.S. Pat. No. 6,274,579; and U.S. Pat. No. 6,391,875; see also Shepard, *Pharmacotherapy* (2005) 10: 1378-82). Other undesirable side effects may also occur in the administration of therapeutic amine compounds and such compounds may be considered in trials conducted for potential abuse liability. Thus, such compounds may be under-utilized at administration dose maximums, even if favorable treatment outcomes are possible.

To the extent these and other therapeutic amine compounds exhibit undesirable side effects, compounds and/methods of treatment which avoid such side effects would be advantageous. The conjugate compounds and methods disclosed herein provide such advantages.

SUMMARY

Disclosed herein are therapeutic amine-arylsulfonamide conjugate compounds, processes for preparing them, pharmaceutical formulations containing them, and their preparation and use in medicine. The various embodiments encompass therapeutic amine-arylsulfonamide conjugate compounds, particularly those that contain therapeutic amine moieties with potentially intrinsic convulsant, pro-convulsant, or abuse liability properties. By conjugating therapeutic amines with arylsulfonamides via an in vivo cleavable chemical linker, otherwise seizure-prone or abuse liable compounds may be rendered effective as viable treatments to psychiatric, neurologic and metabolic disorders.

In embodiments, therapeutic-arylsulfonamide conjugate compounds are provided, including pharmaceutically acceptable esters, amides, salts or solvates thereof, comprising the structures:

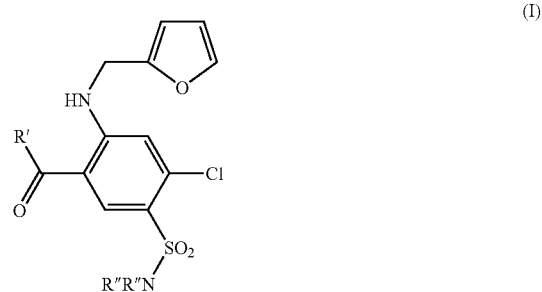

(I)

where R' is [D-W-], hydroxyl, or alkoxyl;

R" is independently [D-W'-], hydrogen, alkoxy, alkyl, cycloalkyl, alkenyl, alkynyl or aryl, or R" and R" together with the nitrogen atom to which they are attached form a 4-, 5-, 6-, 7- or 8-membered ring optionally containing one or two further heteroatoms independently selected from nitrogen, oxygen and sulfur;

D is independently a therapeutic amine radical comprising at least one nitrogen atom and optionally at least one oxygen atom coupled to W or W' by a nitrogen or oxygen atom; and W and W' are a chemical bond or linker;

wherein either R' is [D-W-] or at least one R" is [D-W'-].

In embodiments, the therapeutic amine radical is derived from an amine selected from: (2S,3S,5R)-2-(3,5-difluorophenyl)-3,5-dimethyl-2-morpholinol (manifaxine), 2-(1-(3,5-difluorobenzoyl)-(R,S)-ethylamino)-(R)-2-methylethanol, (2S,3S)-2-(3-chlorophenyl)-3,5,5-trimethyl-2-morpholinol, (+)-(2S,3S)-2-(3-chlorophenyl)-3,5,5-trimethyl-2-morpholinol (radafaxine), 2-(1-(3-chlorobenzoyl)-(R,S)-ethylamino)-2,2-dimethylethanol, 1-(3-chlorophenyl)-2-[(1,1-dimethylethyl)amino]-1-propanone (bupropion), citalopram, escitalopram, paroxetine, fluoxetine, fluvoxamine, sertraline, phenelzine, tranylcypromine, amitriptyline, amoxapine, clomipramine, desipramine, doxepine, imipramine, nortryptyline, protriptyline, trimipramine, maprotiline, mirtazapine, duloxetine, nefazodone, trazodone, and venlafaxine.

In embodiments, the linker W comprises:
—CHRO—;
—C(O)OCHRO—;
—C(O)OCHROC(O)R¹O—;
—C(O)R¹O—;
—CHROC(O)R¹O—;
—C(O)R¹OC(O)R¹O—;
—CHROC(O)R¹OC(O)R¹O—;
wherein R¹ is independently:
—(CH₂)ₙ—;
—(CH₂)ₒCHY(CH₂)ₙ—;

—(CH$_2$)$_o$CH=CH(CH$_2$)$_n$—;
—(CH$_2$)$_n$O(CH$_2$)$_n$—;
—(CH$_2$)$_n$NR(CH$_2$)$_n$—;
—(CH$_2$)$_o$C≡C(CH$_2$)$_n$—;
—(CH$_2$)$_n$S(O)$_m$(CH$_2$)$_n$—;
—(CH$_2$)$_n$C(O)O(CH$_2$)$_n$—;
—(CH$_2$)$_n$C(O)O(CH$_2$)$_n$CHY(CH$_2$)$_n$—;
—(CH$_2$)$_n$C(O)O(CH$_2$)$_n$CH=CH(CH$_2$)$_n$—;
—(CH$_2$)$_n$C(O)O(CH$_2$)$_n$O(CH$_2$)$_n$—;
—(CH$_2$)$_n$C(O)O(CH$_2$)$_n$NR(CH$_2$)$_n$—;
—(CH$_2$)$_n$C(O)O(CH$_2$)$_n$S(O)$_m$(CH$_2$)$_n$—;
—(CH$_2$)$_n$C(O)O(CH$_2$)$_n$C≡C(CH$_2$)$_n$—; or a 5- or 6-membered aromatic ring diradical optionally containing 1 or more heteroatoms independently selected from oxygen, nitrogen and sulfur;

R is independently hydrogen, alkyl, cycloalkyl or aryl;

Y is a halogen;

n is independently 1-8;

m is 0, 1, or 2; and o is 0-8.

In embodiments, the linker W' comprises:
—CHROC(O)R$^1$C(O)OCHR—;
—C(O)R$^1$C(O)OCHR—;
—C(O)OCHROC(O)R$^1$C(O)OCHR—;
—CHROC(O)R$^1$C(O)OCHROC(O)—;
—C(O)R$^1$C(O)OCHROC(O)—; or
—C(O)OCHROC(O)R$^1$C(O)OCHROC(O)—;

wherein R$^1$, R, Y, n, m and o are as described above.

In embodiments, the linker may provide for conjugation of more than one therapeutic amine radical and more than one arylsulfonamide radical to enable independently varying the dosage of each component of the conjugate.

In embodiments, the linker W or W' is enzymatically cleavable, enzymatically degradable, or physiologically hydrolyzable in vivo. The linker may provide for cleavage of either the therapeutic amine or arylsulfonamide from the conjugate compound with the remaining linker moiety, if any, being enzymatically degradable or physiologically hydrolyzable.

In embodiments, a method of making a pharmaceutical composition suitable for treating psychiatric, neurologic and metabolic disorders such as depression, obesity, fibromyalgia, neuropathic pain, restless leg syndrome, attention deficit hyperactivity disorder (ADHD), migraine, pain, sexual dysfunction, Parkinson's disease, Alzheimer's disease, anxiety, narcolepsy-cataplexy syndrome, seizures or drug/substance addiction/cessation, is disclosed, comprising reacting a therapeutic amine, an arylsulfonamide, and optionally a linker, and isolating a therapeutic amine-arylsulfonamide conjugate compound, or a pharmaceutically acceptable salt or solvate of the therapeutic amine-arylsulfonamide conjugate compound.

In embodiments, a method is provided for ameliorating or attenuating a convulsant, pro-convulsant, or abuse liability condition resulting from the administration of therapeutic amines used in treating psychiatric, neurologic and metabolic disorders, comprising administering to a patient in need thereof a therapeutically effective amount of an amine-arylsulfonamide conjugate compound:

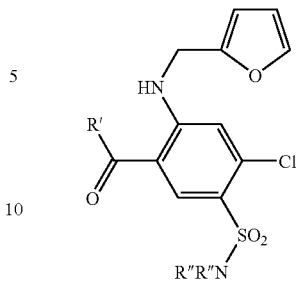

where R' is [D-W-], hydroxyl, or alkoxyl;

R" is independently [D-W'-], hydrogen, alkoxy, alkyl, cycloalkyl, alkenyl, alkynyl or aryl, or R" and R" together with the nitrogen atom to which they are attached form a 4-, 5-, 6-, 7- or 8-membered ring optionally containing one or two further heteroatoms independently selected from nitrogen, oxygen and sulfur;

D is independently a therapeutic amine radical comprising at least one nitrogen atom and optionally at least one oxygen atom coupled to W or W' by a nitrogen or oxygen atom; and W and W' are a chemical bond or linker;

wherein either R' is [D-W-] or at least one R" is [D-W'-];

or a pharmaceutically acceptable ester, amide, salt or solvate thereof.

DETAILED DESCRIPTION

A number of therapeutic amine compounds have been proposed and/or approved for a variety of psychiatric and/or neurologic and/or metabolic disorders. The mechanisms of action and side effects caused by such therapeutic amines are not all known. Therapeutic amine compounds such as bupropion and radafaxine are relatively weak inhibitors of the neuronal uptake of norepinephrine (NE), dopamine (DA), and to a lesser extent, serotonin (5-hydroxytryptamine, 5-HT). (U.S. Pat. No. 6,274,579; and U.S. Pat. No. 6,391,875, incorporated herein by reference in their entireties). The therapeutic amine compound manifaxine, like bupropion, exhibits significant activity in the mouse antitetrabenazine screen for antidepressant activity (U.S. Pat. No. 5,104,870 incorporated herein by reference in its entirety), a test that has been validated with a wide range of antidepressants known to act through norepinephrine mechanisms (Cooper, et al., Animal models used in the prediction of antidepressant effects in man, *Journal of Clinical Psychiatry*, (1983) 44: 63-66). While the mechanism of action of bupropion is unknown, it may be that this action is mediated by norepinephrine and/or dopaminergic mechanisms. Available evidence suggests that bupropion is a selective inhibitor of norepinephrine (NA) reuptake at doses that are predictive of antidepressant activity in animal models. (Ascher, et al., Bupropion: A Review of its Mechanism of Antidepressant Activity, *Journal of Clinical Psychiatry*, (1995) 56: 395-401.) Similarly, the therapeutic efficacy of manifaxine and radafaxine are also considered to be mediated by actions upon norepinephrine and/or dopaminergic reuptake mechanisms. (U.S. Pat. No. 5,104,870; U.S. Pat. No. 6,274,579; and U.S. Pat. No. 6,391,875).

However, bupropion and radafaxine are known to elicit seizures (U.S. Pat. No. 6,274,579; and U.S. Pat. No. 6,391,875). Another concern with drugs that block dopamine uptake sites is their potential reinforcing effects and abuse liability (Volkow, et al., The slow and long-lasting blockade of dopamine transporters in human brain induced by the new antidepressant drug radafaxine predict poor reinforcing effects, *Biol Psychiatry*, (2005) 15: 640-46.). Furthermore, the rate of entry of drugs into brain is thought to be a factor in their abuse liability (Stathis et al., Rate of binding of various inhibitors at the dopamine transporter in vivo, *Psychopharmacology*, (1995) 119(4): 376-84).

Arylsulfonamide compounds such as furosemide (or frusemide), which is the active ingredient in the antidiuretic LASIX®, may exhibit anticonvulsant properties. (Ahmad, et al., Controlled trial of frusemide as an antiepileptic drug in focal epilepsy, *Br. J. Clin. Pharmac.*, (1976) 3: 621-25; Ahmad, et al., The effect of frusemide, mexiletine, (+)-propranolol and three benzodizaepine drugs on the interictal spike discharges in the electroencephalograms of epileptic patients. *Br. J. Clin. Pharmac.*, (1977) 4:683-88; Espinosa, L. J., The anticonvulsant activity of Lasix (Spanish), *Medicina Espanola*, (1969) 61:280-82; Kielczewska-Mrozikiewicz, D., Experimental studies on the effect of Lasix on the occurrence of Cardiazol convulsions, *Przeglad Lekarski*, (1968) 24:716-18.)

Compounds and their compositions comprising conjugate compounds of at least one therapeutic amine radical with at least one arylsulfonamide radical are provided for treatment of psychiatric, neurologic and metabolic disorders. Such conjugate compounds may be suitable for use as therapeutics with the benefit of attenuation or amelioration of undesirable side effects of the therapeutic amine component of the conjugate. By virtue of potential intrinsic anticonvulsant properties of arylsulfonamides, amine-arylsulfonamide conjugate compounds may attenuate or ameliorate the adverse side effects such as convulsions associated with therapeutic amines, for example, bupropion, manifaxine and radafaxine. By way of example, such therapeutic amine radicals are derived from, but are not limited to, therapeutic amines including bupropion, manifaxine and radafaxine, and such arylsulfonamides radicals are derived from, without limitation, furosemide or furosemide congeners or derivatives.

In embodiments, an amine-arylsulfonamide conjugate compound:

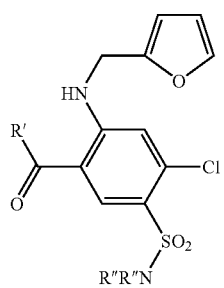

where R' is [D-W-], hydroxyl, or alkoxyl;
R" is independently [D-W'-], hydrogen, alkoxy, alkyl, cycloalkyl, alkenyl, alkynyl or aryl, or R" and R" together with the nitrogen atom to which they are attached form a 4-, 5-, 6-, 7- or 8-membered ring optionally containing one or two further heteroatoms independently selected from nitrogen, oxygen and sulfur;
D is independently a therapeutic amine radical comprising at least one nitrogen atom and optionally at least one oxygen atom coupled to W or W' by a nitrogen or oxygen atom; and W and W' are a chemical bond or linker;
wherein either R' is [D-W-] or at least one R" is [D-W'-]; or a pharmaceutically acceptable ester, amide, salt or solvate thereof is provided.

The therapeutic amine radical of the therapeutic amine-arylsulfonamide may be derived from at least one therapeutic amine selected from: manifaxine; 2-(1-(3,5-difluorobenzoyl)-(R,S)-ethylamino)-(R)-2-methylethanol; (2S,3S)-2-(3-chlorophenyl)-3,5,5-trimethyl-2-morpholinol; radafaxine; 2-(1-(3-chlorobenzoyl)-(R,S)-ethylamino)-2,2-dimethylethanol; bupropion; citalopram; escitalopram; paroxetine; fluoxetine; fluvoxamine; sertraline; phenelzine; tranylcypromine; amitriptyline; amoxapine; clomipramine; desipramine; doxepine; imipramine; nortryptyline; protriptyline; trimipramine; maprotiline; mirtazapine; duloxetine; nefazodone; trazodone; and venlafaxine.

Therapeutic amine radicals may be conjugated with arylsulfonamide radicals by employing a chemical bond or a linker. For example, a linker group may contain one or more chemical groups which are susceptible to catabolic hydrolysis, physiological hydrolysis, or enzymatic cleavage, including combinations thereof. Such hydrolysis may be, for example, by esterase enzymes within biocompartments such as blood plasma, brain, or GI tract. Such cleavage of the chemical linker may liberate at least one of the conjugated bioactive compounds, either simultaneously, or sequentially. Each component of the conjugate may have an independent or identical rate of cleavage from the linker, an independent or identical rate of uptake, an independent or identical rate of clearance, or combinations thereof.

Furthermore, by designing the linker chemistries between the therapeutic amine and aryl sulfonamide radicals to be enzymatically cleaved, the rate of appearance and rate of clearance of the active therapeutic amine drug substance in biocompartments, such as blood plasma, brain, or GI tract may be controlled. By controlling the rate of appearance or clearance of the therapeutic amine, seizure liability and potential drug abuse liability may be attenuated or ameliorated. This is particularly desirable following illicit intravenous bolus injection where rate of delivery of active drug substance and peak drug concentration are critical determinants of abuse liability.

An example of a linker group W is, but not limited to, a linker comprising a chemical bond, one or more ester groups or one or more carbamate groups selected from:
—CHRO—;
—C(O)OCHRO—;
—C(O)OCHROC(O)R$^1$O—;
—C(O)R$^1$O—;
—CHROC(O)R$^1$O—;
—C(O)R$^1$OC(O)R$^1$O—; or
—CHROC(O)R$^1$OC(O)R$^1$O—;
wherein R$^1$ is independently:
—(CH$_2$)$_n$—;
—(CH$_2$)$_o$CHY(CH$_2$)$_n$—;
—(CH$_2$)$_o$CH═CH(CH$_2$)$_n$—;
—(CH$_2$)$_n$O(CH$_2$)$_n$—;
—(CH$_2$)$_n$NR(CH$_2$)$_n$—;
—(CH$_2$)$_o$C≡C(CH$_2$)$_n$—;
—(CH$_2$)$_n$C(O)O(CH$_2$)$_n$—;
—(CH$_2$)$_n$C(O)O(CH$_2$)$_n$CHY(CH$_2$)$_n$—;
—(CH$_2$)$_n$C(O)O(CH$_2$)$_n$CH═CH(CH$_2$)$_n$—;
—(CH$_2$)$_n$C(O)O(CH$_2$)$_n$O(CH$_2$)$_n$—;
—(CH$_2$)$_n$C(O)O(CH$_2$)$_n$NR(CH$_2$)$_n$—;
—(CH$_2$)$_n$C(O)O(CH$_2$)$_n$S(O)$_m$(CH$_2$)$_n$—;
—(CH$_2$)$_n$C(O)O(CH$_2$)$_n$C≡C(CH$_2$)$_n$—; or
a 5- or 6-membered aromatic ring diradical optionally containing 1 or more heteroatoms independently selected from oxygen, nitrogen and sulfur, the 5- or 6-membered aromatic ring diradical optionally substituted by hydroxy, hydroxyalkyl, halogen, amino, alkyl, or alkoxyalkyl;

R is independently hydrogen, alkyl, cycloalkyl or aryl, wherein any of cycloalkyl or aryl are optionally substituted with alkyl, hydroxy, alkoxy, halogen or amino;

Y is a halogen;

n is independently 1-8;

m is 0, 1, or 2; and o is 0-8.

An example of a linker group W' is, but not limited to, a linker comprising one or more ester groups, one or more carbamate groups, or one or more chemical bonds selected from:

—CHROC(O)R$^1$C(O)OCHR—;

—C(O)R$^1$C(O)OCHR—;

—C(O)OCHROC(O)R$^1$C(O)OCHR—;

—CHROC(O)R$^1$C(O)OCHROC(O)—;

—C(O)R$^1$C(O)OCHROC(O)NH—; or

—C(O)OCHROC(O)R$^1$C(O)OCHROC(O)—;

wherein R$^1$, R, Y, n, m and o are as described above.

For example, such ester groups include groups which are susceptible to catabolic hydrolysis by esterase enzymes within various biocompartments such as blood plasma, brain, or GI tract.

In embodiments, one or more therapeutic amine radicals may be conjugated with one or more arylsulfonamide radicals employing a linker group comprising at least one carbamate group. In embodiments, only one of R' and R" is [D-W] or [D-W']. The above disclosed conjugate compound embodiments include pharmaceutically acceptable esters, amides, salts or solvates thereof.

It is further understood that the embodiments disclosed herein include enantiomeric and diastereomeric forms of compound (I) either individually or admixed in any proportion.

One or more therapeutic amines radicals may be conjugated with one or more arylsulfonamide radicals by employing a poly-functional chemical linker. In this embodiment, the ratio of therapeutic amine to arylsufonamide may be adjusted to a desired pharmacokinetic or pharmacodynamic profile range as needed to ameliorate or treat a particular disorder.

In addition, the conjugate compound embodiments further include prodrugs and active metabolites of compound (I). A prodrug includes any compound which, for example, when administered to a mammal, is converted in whole or in part to any of the embodiments represented by (I). An active metabolite is a physiologically active compound which results from the metabolism of (I), or a prodrug thereof, when such compound (I), or a prodrug thereof is administered to a mammal.

As used herein, the terms "alkyl" and "alkylene" refer to straight or branched hydrocarbon chains containing from 1 to 8 carbon atoms. By way of example, "alkyl" includes methyl, ethyl, n-propyl, n-butyl, n-pentyl, isobutyl, isopropyl, and tert-butyl. Examples of "alkylene" as used herein include, but are not limited to, methylene, ethylene, propylene, butylene, and isobutylene. "Alkyl" also includes substituted alkyl or alkylene. The alkyl groups may be optionally substituted one or more times on an available carbon with a substituent selected from hydroxy, alkoxy, amino, mercapto, nitro, cyano, cycloalkyl or halogen. By way of example, substituted alkyl includes trifluoromethyl, 2,2,2-trifluoroethyl, 2,2-difluoroethyl, 2-fluoroethyl, and cyclopropylmethyl.

As used herein, the terms "hydroxyalkyl" and "alkoxyalkyl" refer to alkyl groups of 1 to 6 carbon atoms substituted with a hydroxy functionality, for example, —CH$_2$CH$_2$OH, or an alkoxy functionality, for example, —CH$_2$CH$_2$OCH$_3$, respectively.

As used herein, the term "cycloalkyl" refers to a non-aromatic carbocyclic ring having from 3 to 8 carbon atoms absent any carbon-carbon double bonds. By way of example, "cycloalkyl" includes cyclopropyl, cyclobutyl, cyclopentyl, cyclohexyl, cycloheptyl and cyclooctyl. "Cycloalkyl" also includes substituted cycloalkyl. The cycloalkyl may optionally be substituted on an available carbon with one or more substituents selected from hydroxy, alkoxy, amino, mercapto, nitro, cyano, halogen, and alkyl.

As used herein, the term "alkenyl" refers to straight or branched hydrocarbon chains containing from 2 to 8 carbon atoms and at least one and up to three carbon-carbon double bonds. By way of example, "alkenyl" includes ethenyl and propenyl. "Alkenyl" also includes substituted alkenyl. The alkenyl groups may optionally be substituted on an available carbon with one or more substituents selected from the group consisting of hydroxy, alkoxy, amino, mercapto, nitro, cyano, halogen, and alkyl.

As used herein, the term "cycloalkenyl" refers to refers to a non-aromatic carbocyclic ring having from 3 to 8 carbon atoms and up to 3 carbon-carbon double bonds. By way of example, "cycloalkenyl" includes cyclobutenyl, cyclopentenyl and cyclohexenyl. "Cycloalkenyl" also includes substituted cycloalkenyl. The cycloalkenyl may optionally be substituted on an available carbon with one or more substituents selected from hydroxy, alkoxy, amino, mercapto, nitro, cyano, halogen, and alkyl.

As used herein, the term "alkynyl" refers to straight or branched hydrocarbon chains containing from 2 to 8 carbon atoms and at least one and up to three carbon-carbon triple bonds. By way of example, "alkynyl" includes ethynyl and 2-propynyl. "Alkynyl" also includes substituted alkynyl. The alkynyl may optionally be substituted on an available carbon with one or more substituents selected from hydroxy, alkoxy, amino, mercapto, nitro, cyano, halogen, and alkyl.

As used herein, the term "aryl" refers to monocyclic carbocyclic groups and fused bicyclic carbocyclic groups having from 6 to 10 carbon atoms and having at least one aromatic ring. By way of example, aryl includes phenyl, and naphthyl. "Aryl" also includes substituted aryl. The aryl may be optionally substituted on an available carbon with one or more substituents selected from alkyl, hydroxyalkyl, alkoxyalkyl, cycloalkyl, alkenyl, alkynyl, aryloxy, aryl, haloalkyl, haloalkoxy, cyano, nitro, sulfonamido, alkylsulfonyl, alkylsulfinyl, alkylthio, hydroxy, carboxyl, alkoxycarbonyl, carboxamido, sulfoxy, alkoxy, amino, alkylamino, carbamoyl or halogen. By way of example, substituted aryl includes benzyl and phenethyl.

As used herein, the term "R" and R" together with the nitrogen atom to which they are attached form a 4-, 5-, 6-, 7- or 8-membered ring" refers to a monocyclic saturated or unsaturated non-aromatic ring or a fused bicyclic aromatic and non-aromatic ring, the ring having the specified number of members (total carbon atoms and the nitrogen of the arylsulfonamide group). The ring may optionally contain 1, 2, 3 or 4 heteroatoms independently selected from N, O and S. The ring may be optionally substituted on any available carbon or heteroatom, with one or more substituents optionally selected from alkyl, hydroxyalkyl, alkoxyalkyl, cycloalkyl, alkenyl, alkynyl, aryloxy, aryl, haloalkyl, haloalkoxy, cyano, nitro, sulfonamido, alkylsulfonyl, alkylsulfinyl, alkylthio, hydroxy, carboxyl, alkoxycarbonyl, carboxamido, sulfoxy, alkoxy, amino, alkylamino, carbamoyl or halogen. By way of example, substituted ring substituents include hydroxy, hydroxyalkyl, oxo, alkyl, haloalkyl, and/or haloalkoxy.

"Halogen" means F, Cl, Br, or I.

"Radical" refers to one or more residues derived from: 1) the corresponding amine by eliminating a —H portion of a primary amine group or —H, -alkyl, or -alkoxyl portion of a secondary amine group, or an alkyl group of a quaternary ammonium salt; 2) the corresponding carbonyl by eliminating a —OH group, a —NH group, a —OR ester group, or a —R portion of the carbonyl group; and 3) the corresponding thiol by eliminating a —H portion of a —SH group.

"5- or 6-membered aromatic ring diradical" refers to a chemical moiety represented by the following:

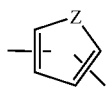

where Z is S, O, NR or C=C; and where R is hydrogen, alkyl, or cycloalkyl or aryl. The 5- or 6-membered aromatic ring diradical may be substituted on an available carbon with one or more substituents selected from alkyl, hydroxyalkyl, alkoxyalkyl, cycloalkyl, alkenyl, alkynyl, aryloxy, aryl, haloalkyl, haloalkoxy, cyano, nitro, sulfonamido, alkylsulfonyl, alkylsulfinyl, alkylthio, hydroxy, carboxyl, alkoxycarbonyl, carboxamido, sulfoxy, alkoxy, amino, alkylamino, carbamoyl or halogen. By way of example, diradical substituents include hydroxy, hydroxyalkyl, halogen, amino, alkyl, or alkoxyalkyl.

"Therapeutic amine radical" means a radical derived from an amine-containing chemical moiety that when administered to a subject provides for a therapeutic effect. Typically, the therapeutic amine radical from an amine-containing chemical moiety administered to a subject for treating psychiatric and/or neurologic and/or metabolic disorders, wherein the amine-containing chemical moiety may induce adverse side effects such as convulsant, pro-convulsant, or abuse liability. By way of example, therapeutic amine radicals may be derived from the therapeutic amines selected from manifaxine; 2-(1-(3,5-difluorobenzoyl)-(R,S)-ethylamino)-(R)-2-methylethanol; (2S,3S)-2-(3-chlorophenyl)-3,5,5-trimethyl-2-morpholinol; radafaxine; 2-(1-(3-chlorobenzoyl)-(R,S)-ethylamino)-2,2-dimethylethanol; bupropion; citalopram; escitalopram; paroxetine; fluoxetine; fluvoxamine; sertraline; phenelzine; tranylcypromine; amitriptyline; amoxapine; clomipramine; desipramine; doxepine; imipramine; nortryptyline; protriptyline; trimipramine; maprotiline; mirtazapine; duloxetine; nefazodone; trazodone; or venlafaxine.

"Arylsulfonamide radical" means a chemical moiety having the following general structure:

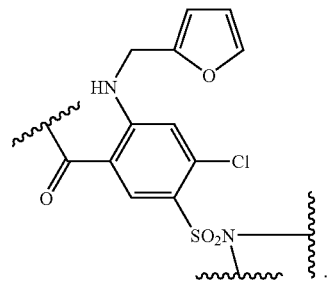

Exemplary embodiments of arylsulfonamide radicals include, but are not limited to radicals derived from furosemide (or frosemide) or furosemide congeners. In embodiments, the arylsulfonamide radical is covalently bonded to a linker moiety by the carbonyl portion of the corresponding carbonyl group. In embodiments, the arylsulfonamide radical is covalently bonded to at least one linker moiety by one or more of the sulfamidyl portions of the corresponding sulfamidyl group. In embodiments, the arylsulfonamide radical is covalently bonded to a therapeutic amine moiety by a single bond.

The term "linker" and "chemical linker" are used herein interchangeably. The term "linker" refers to an atom, or a collection of atoms used to link interconnecting moieties such as a therapeutic amine radical and an arylsulfonamide radical. A linker may be hydrolytically stable or undergo spontaneous cleavage in the presence of water, or may include a physiologically hydrolyzable, enzymatically cleavable, or enzymatically degradable linkage. "Linker" comprises functional groups selected from carboxylate, carbonyl, carboxyl, carbamate, carbonate, ester, thioamidyl, thiocarbamyl, or thiolester groups.

"Enzymatically degradable" refers to a chemical bond or a linker, wherein all or part of the bond or linker may be degraded by one or more enzymes.

"Enzymatically cleavable" refers to a chemical bond or a linker, wherein either the therapeutic amine or the arylsulfonamide constitutents may be cleaved from the chemical bond or linker, by one or more enzymes. A linker may provide an enzymatic cleavage site with the remaining portion of the linker being enzymatically degradable or physiologically hydrolyzable. The linker may be enzymatically degraded or physiologically hydrolyzable prior to cleavage of either the therapeutic amine or the arylsulfonamide constitutents from the chemical bond or linker.

"Physiological hydrolysis" or "physiologically hydrolyzable," or "physiologically hydrolyzing" means replacement of the linker that is connected to either the therapeutic amine radical or the arylsulfonamide radical of the conjugate compound with a hydroxyl group on the carbonyl radical of the arylsulfonamide, or a hydrogen on the sulfonamide radical of the arylsulfonamide or the nitrogen or oxygen atom of the therapeutic amine connected to the linker, in the presence of water or aqueous media of biological origin.

"Psychiatric, neurologic and metabolic disorders" is meant to include, but not be limited to, depression, obesity, fibromyalgia, neuropathic pain, restless leg syndrome, attention deficit hyperactivity disorder (ADHD), migraine, pain, sexual dysfunction, Parkinson's disease, Alzheimer's disease, anxiety, narcolepsy-cataplexy syndrome, seizures, drug/substance addiction/cessation and combinations thereof.

"Conjugate compound" refers to at least one first compound or part of a first compound that has pharmacological activity linked to at least one second compound or part of a second compound that has independent pharmacological activity, whereas the linked first and second compound form a conjugate that optionally has pharmacological activity. Typically, both the first or second compounds have independent pharmacologic activity without being linked as in the conjugate. The conjugate may facilitate therapeutic use of both the first and second compounds by providing independent pharmacologic activity, independent clearance, and independent uptake of each first and second compound. A conjugate formed from a first compound and a second compound can have higher or lower pharmacologic activity, clearance activity, or uptake activity than either compound alone. The individual compounds (or constituents) of a conjugate compound may be linked by covalent bonds. Additional compounds, for example a third, fourth, etc., compound are also within the scope of the various conjugate compound embodiments herein described. Preferably, the conjugate compound has at least one of a first compound derived from a therapeutic amine and at least one of a second compound derived from an arylsulfonamide.

"Therapeutically effective amount" means the quantity of conjugate compound, that when administered to an individual or animal results in a sufficiently high level of therapeutic amine and/or arylsulfonamide constituent in the individual or animal to cause a discernible attenuation or amelioration of symptoms of an underlying psychiatric, neurologic or metabolic disorder with a concomitant reduced likelihood of adverse effects.

As used herein, the term "treatment" and its grammatical equivalents refer to the alleviation, amelioration, attenuation or elimination of etiological or pathological symptoms and include, for example, the elimination of such symptom causation either on a temporary or permanent basis, or to alter or slow the appearance of such symptoms or symptom worsening. For example, the term "treatment" includes alleviation or elimination of causation of symptoms associated with, but not limited to, any of the adverse effects caused by the therapeutic amine or the psychiatric, neurologic and metabolic disorders described herein.

"Pharmaceutically acceptable salts" refers to relatively non-toxic, inorganic and organic acid addition salts of compound (I). Pharmaceutically acceptable salts suitable for medical applications, due to their greater solubility in water compared with the starting or base compounds are also envisaged as additional embodiments. Said salts have a pharmaceutically acceptable anion or cation. Suitable pharmaceutically acceptable acid addition salts of compound (I) include salts of inorganic acids such as hydrochloric acid, hydrobromic acid, phosphoric acid, metaphosphoric acid, nitric acid, sulfonic acid, and sulfuric acid, and also of organic acids such as, for example, acetic acid, benzenesulfonic acid, benzoic acid, citric acid, ethanesulfonic acid, fumaric acid, gluconic acid, glycolic acid, isethionic acid, lactic acid, lactobionic acid, maleic acid, malic acid, methanesulfonic acid, succinic acid, p-toluenesulfonic acid, tartaric acid and trifluoroacetic acid and, additionally L-ascorbic acid, salicylic acid, 1,2-benzisothiazol-3(2H)-one and 6-methyl-1,2,3-oxathiazin-4(3H)-one 2,2-dioxide. Suitable pharmaceutically acceptable basic salts include ammonium salts, alkali metal salts (such as sodium salts and potassium salts) and alkaline earth metal salts (such as magnesium salts and calcium salts). Salts having a pharmaceutically unacceptable anion or cation are likewise included within the scope of the present invention as useful intermediates for preparing or purifying pharmaceutically acceptable salts and/or for use in nontherapeutic applications, for example in vitro applications. Suitable pharmaceutically acceptable carriers and their formulations are described in standard formulation treaties, e.g., Remington's Pharmaceutical Science by E. W. Martin. See also Wang et al., Parental Formulations of Proteins and Peptides: Stability and Stabilizer, *Journals of Parental Sciences and Technology*, Technical Report No. 10, Supp. 42: 2S (1988). In addition, the pharmaceutically acceptable salt of compound (I) may be a quaternary ammonium compound formed by reacting a tertiary amine of the therapeutic amine with an alkyl derivative of the arylsulfonamide.

Exemplary therapeutic amine-arysulfonamide conjugate compounds, where the arylsulfonamide radical is covalently bonded to a linker moiety by the carbonyl portion of the corresponding carbonyl group are presented in Table I. A chemical bond between the therapeutic amine radical and linker radical is represented by the wavy line. A chemical bond between the linker radical and arylsulfonamide is represented by the dashed line. The wavy and dashed lines taken together would represent a chemical bond between the therapeutic amine radical and arylsulfonamide radical.

TABLE I

| Therapeutic amine radical | W linker examples | Arylsulfonamide radical |
|---|---|---|
| 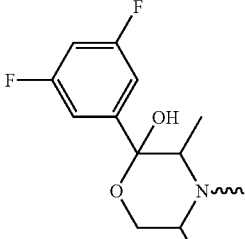 or 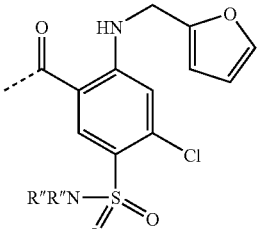 or 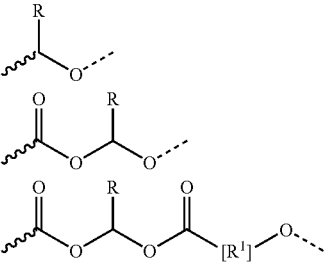 or  or 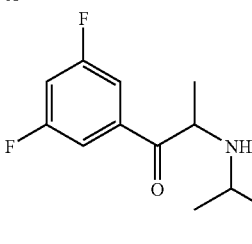 | chemical bond; 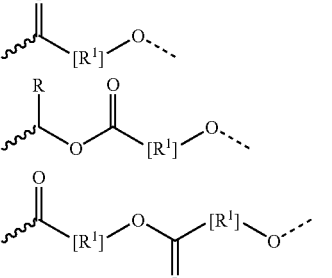  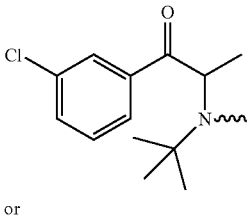 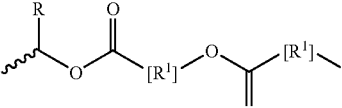 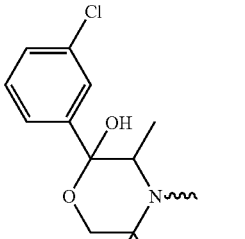 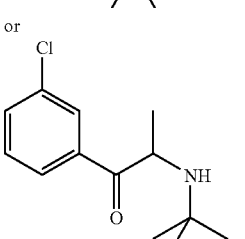 wherein $R^1$ may be<br>i —(CH$_2$)$n$—<br>ii —(CH$_2$)$o$—CHY—(CH$_2$)$n$—<br>iii —(CH$_2$)$n$—S(O)$_{0,1, or 2}$—(CH$_2$)$n$—<br>iv —(CH$_2$)$n$—O—(CH$_2$)$n$—<br>v —(CH$_2$)$n$—C(O)—O—(CH$_2$)$n$—<br>vi —(CH$_2$)$o$—CH=CH—(CH$_2$)$n$— cis or trans<br>vii —(CH$_2$)$o$—C≡C—(CH$_2$)$n$—<br>viii —(CH$_2$)$n$—NR—(CH$_2$)$n$—<br>ix 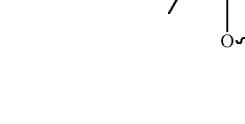<br>x (CH$_2$)$n$—C(O)—O—Q<br><br>wherein R may be independently hydrogen, alkyl, or cycloalkyl or aryl;<br>wherein Q is any one of ii–ix;<br>Y is halogen;<br>n is 1–8;<br>o is 0–8; and<br>Z is O, S, NR or C=C; where R may be hydrogen, alkyl, or cycloalkyl or aryl. | <br><br>R″ as described above |

TABLE II

| Therapeutic amine radical examples | W' linker examples | Arylsulfonamide radical |
|---|---|---|
| 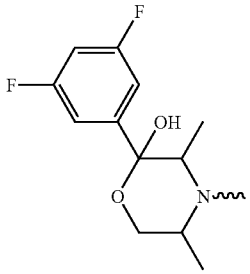 or 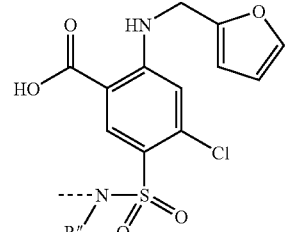 or 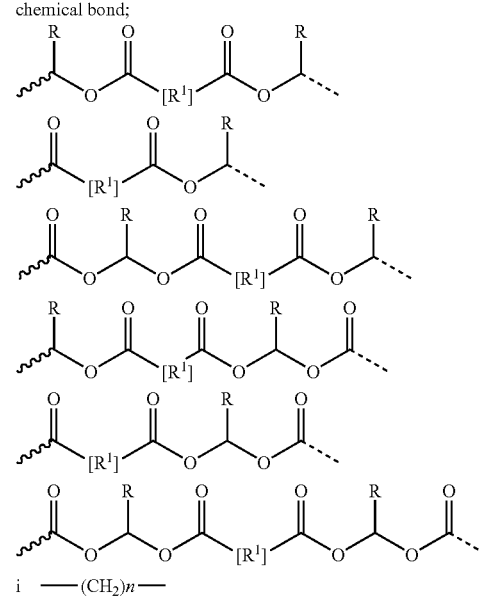 or 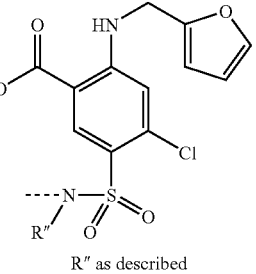 or 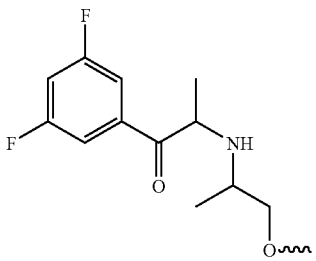 | chemical bond; 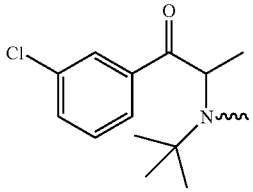<br>i —(CH$_2$)$n$—<br>ii —(CH$_2$)$o$—C(Y)(H)—(CH$_2$)$n$—<br>iii —(CH$_2$)$n$—S(O)$_{0,1,or 2}$—(CH$_2$)$n$—<br>iv —(CH$_2$)$n$—O—(CH$_2$)$n$—<br>v —(CH$_2$)$n$—C(O)—O—(CH$_2$)$n$—<br>vi —(CH$_2$)$o$—CH=CH—(CH$_2$)$n$— cis or trans<br>vii —(CH$_2$)$o$—C≡C—(CH$_2$)$n$—<br>viii —(CH$_2$)$n$—N(R)—(CH$_2$)$n$—<br>ix 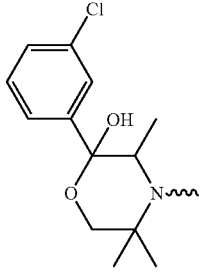<br>x (CH$_2$)$n$—C(O)—O—Q | 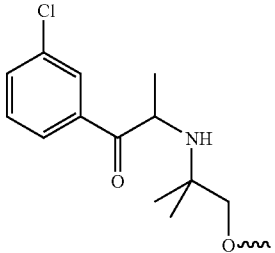<br>R″ as described above or covalent bond to linker moiety | wherein R may be independently hydrogen, alkyl, or cycloalkyl or aryl;
wherein Q is any one of ii–ix;
Y is halogen;
n is 1–8;
o is 0–8; and
Z is O, S, NR or C=C; where R may be hydrogen, alkyl, or cycloalkyl or aryl.

Exemplary therapeutic amine-arysulfonamide conjugate compounds, where the arylsulfonamide radical is covalently bonded to a linker moiety by one or more of the sulfamidyl portions of the corresponding sulfamidyl group are shown in Table II.

Specific therapeutic amine-arysulfonamide conjugate compounds include, but are not limited to, the following:

2-(1-(3,5-difluorobenzoyl)-(R,S)-ethylamino)-(R)-2-methylethyl 5-(aminosulfonyl)-4-chloro-2-[(2-furanylmethyl)amino]benzoate;

2-(1-(3-chlorobenzoyl)-(R,S)-ethylamino)-2,2-dimethylethyl 5-(aminosulfonyl)-4-chloro-2-[(2-furanylmethyl)amino]benzoate;

2-(1-(3,5-difluorobenzoyl)-(R,S)-ethylamino)-(R)-2-methylethyl 4-(5-(aminosulfonyl)-4-chloro-2-[(2-furanylmethyl)amino]benzoyloxy)butanoate;

2-(1-(3-chlorobenzoyl)-(R,S)-ethylamino)-2,2-dimethylethyl 4-(5-(aminosulfonyl)-4-chloro-2-[(2-furanylmethyl)amino]benzoyloxy)butanoate;

2-(1-(3,5-difluorobenzoyl)-(R,S)-ethylamino)-(R)-2-methylethyl 2-(5-(aminosulfonyl)-4-chloro-2-[(2-furanylmethyl)amino]benzoyloxy)ethanoate;

2-(1-(3,5-difluorobenzoyl)-(R,S)-ethylamino)-(R)-2-methylethyl 3-(5-(aminosulfonyl)-4-chloro-2-[(2-furanylmethyl)amino]benzoyloxy)propanoate;

2-(1-(3,5-difluorobenzoyl)-(R,S)-ethylamino)-(R)-2-methylethyl 2-(5-(aminosulfonyl)-4-chloro-2-[(2-furanylmethyl)amino]benzoyloxy)propanoate;

2-(1-(3,5-difluorobenzoyl)-(R,S)-ethylamino)-(R)-2-methylethyl 4-(5-(aminosulfonyl)-4-chloro-2-[(2-furanylmethyl)amino]benzoyloxy)crotonate;

2-(1-(3,5-difluorobenzoyl)-(R,S)-ethylamino)-(R)-2-methylethyl 5-(5-(aminosulfonyl)-4-chloro-2-[(2-furanylmethyl)amino]benzoyloxy)pentanoate;

2-(1-(3,5-difluorobenzoyl)-(R,S)-ethylamino)-(R)-2-methylethyl 6-(5-(aminosulfonyl)-4-chloro-2-[(2-furanylmethyl)amino]benzoyloxy)hexanoate;

2-(1-(3,5-difluorobenzoyl)-(R,S)-ethylamino)-(R)-2-methylethyl 8-(5-(aminosulfonyl)-4-chloro-2-[(2-furanylmethyl)amino]benzoyloxy)octanoate;

2-(1-(3,5-difluorobenzoyl)-(R,S)-ethylamino)-(R)-2-methylethyl 2-(2-(5-(aminosulfonyl)-4-chloro-2-[(2-furanylmethyl)amino]benzoyloxy)ethoxy)ethanoate;

2-(1-(3,5-difluorobenzoyl)-(R,S)-ethylamino)-(R)-2-methylethyl 2-(2-(5-(aminosulfonyl)-4-chloro-2-[(2-furanylmethyl)amino]benzoyloxy)ethylthio)ethanoate;

2-(1-(3,5-difluorobenzoyl)-(R,S)-ethylamino)-(R)-2-methylethyl 2-(2-(5-(aminosulfonyl)-4-chloro-2-[(2-furanylmethyl)amino]benzoyloxy)ethylsulfinyl)ethanoate;

2-(1-(3,5-difluorobenzoyl)-(R,S)-ethylamino)-(R)-2-methylethyl 2-(2-(5-(aminosulfonyl)-4-chloro-2-[(2-furanylmethyl)amino]benzoyloxy)ethylsulfonyl)ethanoate;

2-(1-(3,5-difluorobenzoyl)-(R,S)-ethylamino)-(R)-2-methylethyl 2-((2-(5-(aminosulfonyl)-4-chloro-2-[(2-furanylmethyl)amino]benzoyloxy)ethyl)(methyl)amino)ethanoate;

2-(1-(3,5-difluorobenzoyl)-(R,S)-ethylamino)-(R)-2-methylethyl 4-(5-(aminosulfonyl)-4-chloro-2-[(2-furanylmethyl)amino]benzoyloxy)(2-fluoro)butanoate;

(2S,3S,5R)-4-(5-(aminosulfonyl)-4-chloro-2-[(2-furanylmethyl)amino]benzoyloxymethyl)-2-(3,5-difluorophenyl)-3,5-dimethyl-2-morpholinol;

(2S,3S)-4-(5-(aminosulfonyl)-4-chloro-2-[(2-furanylmethyl)amino]benzoyloxymethyl)-2-(3-chlorophenyl)-3,5,5-trimethyl-2-morpholinol;

(2S,3S,5R)-4-(1-(5-(aminosulfonyl)-4-chloro-2-[(2-furanylmethyl)amino]benzoyloxy)-(R,S)-ethyl)-2-(3,5-difluorophenyl)-3,5-dimethyl-2-morpholinol;

(2S,3S)-4-(1-(5-(aminosulfonyl)-4-chloro-2-[(2-furanylmethyl)amino]benzoyloxy)-(R,S)-ethyl)-2-(3-chlorophenyl)-3,5,5-trimethyl-2-morpholinol;

(2S,3S,5R)-4-[4-(5-(aminosulfonyl)-4-chloro-2-[(2-furanylmethyl)amino]benzoyloxy)butanoyloxymethyl]-2-(3,5-difluorophenyl)-3,5-dimethyl-2-morpholinol;

(2S,3S,5R)-4-[1-(4-(5-(aminosulfonyl)-4-chloro-2-[(2-furanylmethyl)amino]benzoyloxy)butanoyloxy)-(R,S)-ethyl]-2-(3,5-difluorophenyl)-3,5-dimethyl-2-morpholinol;

(2S,3S)-4-[1-(4-(5-(aminosulfonyl)-4-chloro-2-[(2-furanylmethyl)amino]benzoyloxy)butanoyloxy)-(R,S)-ethyl]-2-(3-chlorophenyl)-3,5,5-trimethyl-2-morpholinol;

2-[(1-(4-(5-(aminosulfonyl)-4-chloro-2-[(2-furanylmethyl)amino]benzoyloxy)butanoyloxy)-(R,S)-ethyl)(1,1-dimethylethyl)amino]-1-(3-chlorophenyl)-1-propanone;

2-[(5-(aminosulfonyl)-4-chloro-2-[(2-furanylmethyl)amino]benzoyloxymethyl) (1,1-dimethylethyl)amino]-1-(3-chlorophenyl)-1-propanone;

(2S,3S)-4-[5-(aminosulfonyl)-4-chloro-2-[(2-furanylmethyl)amino]benzoyloxymethyl]-2-(3-chlorophenyl)-3,5,5-trimethyl-2-morpholinol;

(2S,3S,5R)-4-[5-(aminosulfonyl)-4-chloro-2-[(2-furanylmethyl)amino]benzoyloxymethyl]-2-(3,5-difluorophenyl)-3,5-dimethyl-2-morpholinol;

2-(1-(3,5-difluorobenzoyl)-(R,S)-ethylamino)-(R)-2-methylethyl 4-(3-(5-(aminosulfonyl)-4-chloro-2-[(2-furanylmethyl)amino]benzoyloxy)propoxy)(4-oxo)butanoate;

2-(1-(3-chlorobenzoyl)-(R,S)-ethylamino)-2,2-dimethylethyl 4-(3-(5-(aminosulfonyl)-4-chloro-2-[(2-furanylmethyl)amino]benzoyloxy)propoxy)(4-oxo)butanoate;

2-[(4-(3-(5-(aminosulfonyl)-4-chloro-2-[(2-furanylmethyl)amino]benzoyloxy)propoxy)(4-oxo)butanoyloxymethyl)(1,1-dimethylethyl)amino]-1-(3-chlorophenyl)-1-propanone;

2-[(5-(aminosulfonyl)-4-chloro-2-[(2-furanylmethyl)amino]benzoyloxymethoxycarbonyl)(1,1-dimethylethyl)amino]-1-(3-chlorophenyl)-1-propanone;

(2S,3S)-4-[5-(aminosulfonyl)-4-chloro-2-[(2-furanylmethyl)amino]benzoyloxymethoxycarbonyl]-2-(3-chlorophenyl)-3,5,5-trimethyl-2-morpholinol;

(2S,3S,5R)-4-[5-(aminosulfonyl)-4-chloro-2-[(2-furanylmethyl)amino]benzoyloxymethoxycarbonyl]-2-(3,5-difluorophenyl)-3,5-dimethyl-2-morpholinol;

(5-(aminosulfonyl)-4-chloro-2-[(2-furanylmethyl)amino]benzoyloxymethyl)(10,11-dihydro-5H-dibenz[b,f]azepine-5-propyl)dimethylammonium chloride;

2-[(6-(5-carboxy-2-chloro-4-[(2-furanylmethyl)amino]phenylsulfonamidomethoxy)(6-oxo)hexanoyloxymethyl)(1,1-dimethylethyl)amino]-1-(3-chlorophenyl)-1-propanone;

2-(1-(3,5-difluorobenzoyl)-(R,S)-ethylamino)-(R)-2-methylethyl 6-(5-carboxy-2-chloro-4-[(2-furanylmethyl)amino]phenylsulfonamidocarbonyloxymethoxy)(6-oxo)hexanoate;

(2S,3S,5R)-4-[2-(5-(aminosulfonyl)-4-chloro-2-[(2-furanylmethyl)amino]benzoyloxy)ethanoyloxymethoxycarbonyl]-2-(3,5-difluorophenyl)-3,5-dimethyl-2-morpholinol;

(2S,3S,5R)-4-[2-(5-(aminosulfonyl)-4-chloro-2-[(2-furanylmethyl)amino]benzoyloxy)propanoyloxymethoxycarbonyl]-2-(3,5-difluorophenyl)-3,5-dimethyl-2-morpholinol;

(2S,3S,5R)-4-[3-(5-(aminosulfonyl)-4-chloro-2-[(2-furanylmethyl)amino]benzoyloxy)propanoyloxymethoxycarbonyl]-2-(3,5-difluorophenyl)-3,5-dimethyl-2-morpholinol;

(2S,3S,5R)-4-[2-(5-(aminosulfonyl)-4-chloro-2-[(2-furanylmethyl)amino]benzoyloxy)butanoyloxymethoxycarbonyl]-2-(3,5-difluorophenyl)-3,5-dimethyl-2-morpholinol;

(2S,3S,5R)-4-[3-(5-(aminosulfonyl)-4-chloro-2-[(2-furanylmethyl)amino]benzoyloxy)butanoyloxymethoxycarbonyl]-2-(3,5-difluorophenyl)-3,5-dimethyl-2-morpholinol;

(2S,3S,5R)-4-[4-(5-(aminosulfonyl)-4-chloro-2-[(2-furanylmethyl)amino]benzoyloxy)butanoyloxymethoxycarbonyl]-2-(3,5-difluorophenyl)-3,5-dimethyl-2-morpholinol;

(2S,3S,5R)-4-[4-(5-(aminosulfonyl)-4-chloro-2-[(2-furanylmethyl)amino]benzoyloxy)crotonyloxymethoxycarbonyl]-2-(3,5-difluorophenyl)-3,5-dimethyl-2-morpholinol;

(2S,3S,5R)-4-[5-(5-(aminosulfonyl)-4-chloro-2-[(2-furanylmethyl)amino]benzoyloxy)pentanoyloxymethoxycarbonyl]-2-(3,5-difluorophenyl)-3,5-dimethyl-2-morpholinol;

(2S,3S,5R)-4-[6-(5-(aminosulfonyl)-4-chloro-2-[(2-furanylmethyl)amino]benzoyloxy)hexanoyloxymethoxycarbonyl]-2-(3,5-difluorophenyl)-3,5-dimethyl-2-morpholinol;

(2S,3S,5R)-4-[8-(5-(aminosulfonyl)-4-chloro-2-[(2-furanylmethyl) amino]benzoyloxy)octanoyloxymethoxycarbonyl]-2-(3,5-difluorophenyl)-3,5-dimethyl-2-morpholinol;

(2S,3S,5R)-4-[2-(2-(5-(aminosulfonyl)-4-chloro-2-[(2-furanylmethyl)amino]benzoyloxy)ethoxy)ethanoyloxymethoxycarbonyl]-2-(3,5-difluorophenyl)-3,5-dimethyl-2-morpholinol;

(2S,3S,5R)-4-[2-(2-(5-(aminosulfonyl)-4-chloro-2-[(2-furanylmethyl)amino]benzoyloxy)ethylthio)ethanoyloxymethoxycarbonyl]-2-(3,5-difluorophenyl)-3,5-dimethyl-2-morpholinol;

(2S,3S,5R)-4-[2-(2-(5-(aminosulfonyl)-4-chloro-2-[(2-furanylmethyl)amino]benzoyloxy)ethylthio)ethanoyloxymethoxycarbonyl]-2-(3,5-difluorophenyl)-3,5-dimethyl-2-morpholinol;

(2S,3S,5R)-4-[2-(2-(5-(aminosulfonyl)-4-chloro-2-[(2-furanylmethyl)amino]benzoyloxy)ethylsulfinyl)ethanoyloxymethoxycarbonyl]-2-(-3,5-difluorophenyl)-3,5-dimethyl-2-morpholinol;

(2S,3S,5R)-4-[2-((2-(5-(aminosulfonyl)-4-chloro-2-[(2-furanylmethyl)amino]benzoyloxy)ethyl)(methyl)amino)ethanoyloxymethoxycarbonyl]-2-(3,5-difluorophenyl)-3,5-dimethyl-2-morpholinol (2S,3S)-4-[2-(5-(aminosulfonyl)-4-chloro-2-[(2-furanylmethyl)amino]benzoyloxy)ethanoyloxymethoxycarbonyl]-2-(3-chlorophenyl)-3,5,5-trimethyl-2-morpholinol;

(2S,3S)-4-[2-(5-(aminosulfonyl)-4-chloro-2-[(2-furanylmethyl)amino]benzoyloxy)propanoyloxymethoxycarbonyl]-2-(3-chlorophenyl)-3,5,5-trim ethyl-2-morpholinol;

(2S,3S)-4-[3-(5-(aminosulfonyl)-4-chloro-2-[(2-furanylmethyl)amino]benzoyloxy)propanoyloxymethoxycarbonyl]-2-(3-chlorophenyl)-3,5,5-trimethyl-2-morpholinol;

(2S,3S)-4-[2-(5-(aminosulfonyl)-4-chloro-2-[(2-furanylmethyl)amino]benzoyloxy)butanoyloxymethoxycarbonyl]-2-(3-chlorophenyl)-3,5,5-trimethyl-2-morpholinol;

(2S,3S)-4-[3-(5-(aminosulfonyl)-4-chloro-2-[(2-furanylmethyl)amino]benzoyloxy)butanoyloxymethoxycarbonyl]-2-(3-chlorophenyl)-3,5,5-trimethyl-2-morpholinol;

(2S,3S)-4-[4-(5-(aminosulfonyl)-4-chloro-2-[(2-furanylmethyl)amino]benzoyloxy)butanoyloxymethoxycarbonyl]-2-(3-chlorophenyl)-3,5,5-trimethyl-2-morpholinol;

(2S,3S)-4-[4-(5-(aminosulfonyl)-4-chloro-2-[(2-furanylmethyl)amino]benzoyloxy)crotonyloxymethoxycarbonyl]-2-(3-chlorophenyl)-3,5,5-trimethyl-2-morpholinol;

(2S,3S)-4-[5-(5-(aminosulfonyl)-4-chloro-2-[(2-furanylmethyl)amino]benzoyloxy)pentanoyloxymethoxycarbonyl]-2-(3-chlorophenyl)-3,5,5-trimethyl-2-morpholinol;

(2S,3S)-4-[6-(5-(aminosulfonyl)-4-chloro-2-[(2-furanylmethyl)amino]benzoyloxy)hexanoyloxymethoxycarbonyl]-2-(3-chlorophenyl)-3,5,5-trimethyl-2-morpholinol;

(2S,3S)-4-[8-(5-(aminosulfonyl)-4-chloro-2-[(2-furanylmethyl)amino]benzoyloxy)octanoyloxymethoxycarbonyl]-2-(3-chlorophenyl)-3,5,5-trimethyl-2-morpholinol;

(2S,3S)-4-[2-(2-(5-(aminosulfonyl)-4-chloro-2-[(2-furanylmethyl)amino]benzoyloxy)ethoxy)ethanoyloxymethoxycarbonyl]-2-(3-chlorophenyl)-3,5,5-trimethyl-2-morpholinol;

(2S,3S)-4-[2-(2-(5-(aminosulfonyl)-4-chloro-2-[(2-furanylmethyl)amino]benzoyloxy)ethylthio)ethanoyloxymethoxycarbonyl]-2-(3-chlorophenyl)-3,5,5-trimethyl-2-morpholinol;

(2S,3S)-4-[2-(2-(5-(aminosulfonyl)-4-chloro-2-[(2-furanylmethyl)amino]benzoyloxy)ethylsulfinyl)ethanoyloxymethoxycarbonyl]-2-(3-chlorophenyl)-3,5,5-trimethyl-2-morpholinol;

(2S,3S)-4-[2-(2-(5-(aminosulfonyl)-4-chloro-2-[(2-furanylmethyl)amino]benzoyloxy)ethylsulfonyl)ethanoyloxymethoxycarbonyl]-2-(3-chlorophenyl)-3,5,5-trimethyl-2-morpholinol;

(2S,3S)-4-[2-((2-(5-(aminosulfonyl)-4-chloro-2-[(2-furanylmethyl)amino]benzoyloxy)ethyl)(methyl)amino)ethanoyloxymethoxycarbonyl]-2-(3-chlorophenyl)-3,5,5-trimethyl-2-morpholinol;

(2S,3S,5R)-4-[2-(3-(5-(aminosulfonyl)-4-chloro-2-[(2-furanylmethyl)amino]benzoyloxy)propoxy)(2-oxo)ethanoyloxymethoxycarbonyl]-2-(3,5-difluorophenyl)-3,5-dimethyl-2-morpholinol;

(2S,3S,5R)-4-[2-(2-(5-(aminosulfonyl)-4-chloro-2-[(2-furanylmethyl)amino]benzoyloxy)ethoxy)(2-oxo)ethanoyloxymethoxycarbonyl]-2-(3,5-difluorophenyl)-3,5-dimethyl-2-morpholinol;

(2S,3S,5R)-4-[2-(4-(5-(aminosulfonyl)-4-chloro-2-[(2-furanylmethyl)amino]benzoyloxy)butoxy)(2-oxo)ethanoyloxymethoxycarbonyl]-2-(3,5-difluorophenyl)-3,5-dimethyl-2-morpholinol;

(2S,3S,5R)-4-[2-(5-(5-(aminosulfonyl)-4-chloro-2-[(2-furanylmethyl)amino]benzoyloxy)pentyloxy)(2-oxo)ethanoyloxymethoxycarbonyl]-2-(3,5-difluorophenyl)-3,5-dimethyl-2-morpholinol;

(2S,3S,5R)-4-[2-(6-(5-(aminosulfonyl)-4-chloro-2-[(2-furanylmethyl)amino]benzoyloxy)hexyloxy)(2-oxo)ethanoyloxymethoxycarbonyl]-2-(3,5-difluorophenyl)-3,5-dimethyl-2-morpholinol;

(2S,3S,5R)-4-[2-(2-(2-(5-(aminosulfonyl)-4-chloro-2-[(2-furanylmethyl)amino]benzoyloxy)ethoxy)ethoxy)(2-oxo)ethanoyloxymethoxycarbonyl]-2-(3,5-difluorophenyl)-3,5-dimethyl-2-morpholinol;

(2S,3S,5R)-4-[3-(3-(5-(aminosulfonyl)-4-chloro-2-[(2-furanylmethyl)amino]benzoyloxy)propoxy)(3-oxo)propanoyloxymethoxycarbonyl]-2-(3,5-difluorophenyl)-3,5-dimethyl-2-morpholinol;

(2S,3S,5R)-4-[3-(2-(5-(aminosulfonyl)-4-chloro-2-[(2-furanylmethyl)amino]benzoyloxy)ethoxy)(3-oxo)propanoyloxymethoxycarbonyl]-2-(3,5-difluorophenyl)-3,5-dimethyl-2-morpholinol;

(2S,3S,5R)-4-[3-(4-(5-(aminosulfonyl)-4-chloro-2-[(2-furanylmethyl)amino]benzoyloxy)butoxy)(3-oxo)propanoyloxymethoxycarbonyl]-2-(3,5-difluorophenyl)-3,5-dimethyl-2-morpholinol;

(2S,3S,5R)-4-[3-(5-(5-(aminosulfonyl)-4-chloro-2-[(2-furanylmethyl)amino]benzoyloxy)pentyloxy)(3-oxo)propanoyloxymethoxycarbonyl]-2-(3,5-difluorophenyl)-3,5-dimethyl-2-morpholinol;

(2S,3S,5R)-4-[3-(6-(5-(aminosulfonyl)-4-chloro-2-[(2-furanylmethyl)amino]benzoyloxy)hexyloxy)(3-oxo)propanoyloxymethoxycarbonyl]-2-(3,5-difluorophenyl)-3,5-dimethyl-2-morpholinol;

(2S,3S,5R)-4-[3-(2-(2-(5-(aminosulfonyl)-4-chloro-2-[(2-furanylmethyl)amino]benzoyloxy)ethoxy)ethoxy)(3-oxo)propanoyloxymethoxycarbonyl]-2-(3,5-difluorophenyl)-3,5-dimethyl-2-morpholinol;

(2S,3S,5R)-4-[4-(3-(5-(aminosulfonyl)-4-chloro-2-[(2-furanylmethyl)amino]benzoyloxy)propoxy)(4-oxo)butanoyloxymethoxycarbonyl]-2-(3,5-difluorophenyl)-3,5-dimethyl-2-morpholinol;

(2S,3S,5R)-4-[4-(2-(5-(aminosulfonyl)-4-chloro-2-[(2-furanylmethyl)amino]benzoyloxy)ethoxy)(4-oxo)butanoyloxymethoxycarbonyl]-2-(3,5-difluorophenyl)-3,5-dimethyl-2-morpholinol;

(2S,3S,5R)-4-[4-(4-(5-(aminosulfonyl)-4-chloro-2-[(2-furanylmethyl)amino]benzoyloxy)butoxy)(4-oxo)butanoyloxymethoxycarbonyl]-2-(3,5-difluorophenyl)-3,5-dimethyl-2-morpholinol;

(2S,3S,5R)-4-[4-(5-(5-(aminosulfonyl)-4-chloro-2-[(2-furanylmethyl)amino]benzoyloxy)pentyloxy)(4-oxo)butanoyloxymethoxycarbonyl]-2-(3,5-difluorophenyl)-3,5-dimethyl-2-morpholinol;

(2S,3S,5R)-4-[4-(6-(5-(aminosulfonyl)-4-chloro-2-[(2-furanylmethyl)amino]benzoyloxy)hexyloxy)(4-oxo)butanoyloxymethoxycarbonyl]-2-(3,5-difluorophenyl)-3,5-dimethyl-2-morpholinol;

(2S,3S,5R)-4-[4-(2-(2-(5-(aminosulfonyl)-4-chloro-2-[(2-furanylmethyl)amino]benzoyloxy)ethoxy)ethoxy)(4-oxo)butanoyloxymethoxycarbonyl]-2-(3,5-difluorophenyl)-3,5-dimethyl-2-morpholinol;

(2S,3S,5R)-4-[5-(3-(5-(aminosulfonyl)-4-chloro-2-[(2-furanylmethyl)amino]benzoyloxy)propoxy)(5-oxo)pentanoyloxymethoxycarbonyl]-2-(3,5-difluorophenyl)-3,5-dimethyl-2-morpholinol;

(2S,3S,5R)-4-[5-(2-(5-(aminosulfonyl)-4-chloro-2-[(2-furanylmethyl)amino]benzoyloxy)ethoxy)(5-oxo)pentanoyloxymethoxycarbonyl]-2-(3,5-difluorophenyl)-3,5-dimethyl-2-morpholinol;

(2S,3S,5R)-4-[5-(4-(5-(aminosulfonyl)-4-chloro-2-[(2-furanylmethyl)amino]benzoyloxy)butoxy)(5-oxo)pentanoyloxymethoxycarbonyl]-2-(3,5-difluorophenyl)-3,5-dimethyl-2-morpholinol;

(2S,3S,5R)-4-[5-(5-(5-(aminosulfonyl)-4-chloro-2-[(2-furanylmethyl)amino]benzoyloxy)pentyloxy)(5-oxo)pentanoyloxymethoxycarbonyl]-2-(3,5-difluorophenyl)-3,5-dimethyl-2-morpholinol;

(2S,3S,5R)-4-[5-(6-(5-(aminosulfonyl)-4-chloro-2-[(2-furanylmethyl)amino]benzoyloxy)hexyloxy)(5-oxo)pentanoyloxymethoxycarbonyl]-2-(3,5-difluorophenyl)-3,5-dimethyl-2-morpholinol;

(2S,3S,5R)-4-[5-(2-(2-(5-(aminosulfonyl)-4-chloro-2-[(2-furanylmethyl)amino]benzoyloxy)ethoxy)ethoxy)(5-oxo)pentanoyloxymethoxycarbonyl]-2-(3,5-difluorophenyl)-3,5-dimethyl-2-morpholinol (2S,3S)-4-[2-(3-(5-(aminosulfonyl)-4-chloro-2-[(2-furanylmethyl)amino]benzoyloxy)propoxy)(2-oxo)ethanoyloxymethoxycarbonyl]-2-(3-chlorophenyl)-3,5,5-trimethyl-2-morpholinol;

(2S,3S)-4-[2-(2-(5-(aminosulfonyl)-4-chloro-2-[(2-furanylmethyl)amino]benzoyloxy)ethoxy)(2-oxo)ethanoyloxymethoxycarbonyl]-2-(3-chlorophenyl)-3,5,5-trimethyl-2-morpholinol;

(2S,3S)-4-[2-(4-(5-(aminosulfonyl)-4-chloro-2-[(2-furanylmethyl)amino]benzoyloxy)butoxy)(2-oxo)ethanoyloxymethoxycarbonyl]-2-(3-chlorophenyl)-3,5,5-trimethyl-2-morpholinol;

(2S,3S)-4-[2-(5-(5-(aminosulfonyl)-4-chloro-2-[(2-furanylmethyl)amino]benzoyloxy)pentyloxy)(2-oxo)ethanoyloxymethoxycarbonyl]-2-(3-chlorophenyl)-3,5,5-trimethyl-2-morpholinol;

(2S,3S)-4-[2-(6-(5-(aminosulfonyl)-4-chloro-2-[(2-furanylmethyl)amino]benzoyloxy)hexyloxy)(2-oxo)ethanoyloxymethoxycarbonyl]-2-(3-chlorophenyl)-3,5,5-trimethyl-2-morpholinol;

(2S,3S)-4-[2-(2-(2-(5-(aminosulfonyl)-4-chloro-2-[(2-furanylmethyl)amino]benzoyloxy)ethoxy)ethoxy)(2-oxo)ethanoyloxymethoxycarbonyl]-2-(3-chlorophenyl)-3,5,5-trimethyl-2-morpholinol;

(2S,3S)-4-[3-(3-(5-(aminosulfonyl)-4-chloro-2-[(2-furanylmethyl)amino]benzoyloxy)propoxy)(3-oxo)propanoyloxymethoxycarbonyl]-2-(3-chlorophenyl)-3,5,5-trimethyl-2-morpholinol;

(2S,3S)-4-[3-(2-(5-(aminosulfonyl)-4-chloro-2-[(2-furanylmethyl)amino]benzoyloxy)ethoxy)(3-oxo)propanoyloxymethoxycarbonyl]-2-(3-chlorophenyl)-3,5,5-trimethyl-2-morpholinol;

(2S,3S)-4-[3-(4-(5-(aminosulfonyl)-4-chloro-2-[(2-furanylmethyl)amino]benzoyloxy)butoxy)(3-oxo)propanoyloxymethoxycarbonyl]-2-(3-chlorophenyl)-3,5,5-trimethyl-2-morpholinol;

(2S,3S)-4-[3-(5-(5-(aminosulfonyl)-4-chloro-2-[(2-furanylmethyl)amino]benzoyloxy)pentyloxy)(3-oxo)propanoyloxymethoxycarbonyl]-2-(3-chlorophenyl)-3,5,5-trimethyl-2-morpholinol;

(2S,3S)-4-[3-(6-(5-(aminosulfonyl)-4-chloro-2-[(2-furanylmethyl)amino]benzoyloxy)hexyloxy)(3-oxo)propanoyloxymethoxycarbonyl]-2-(3-chlorophenyl)-3,5,5-trimethyl-2-morpholinol;

(2S,3S)-4-[3-(2-(2-(5-(aminosulfonyl)-4-chloro-2-[(2-furanylmethyl)amino]benzoyloxy)ethoxy)ethoxy)(3-oxo)propanoyloxymethoxycarbonyl]-2-(3-chlorophenyl)-3,5,5-trimethyl-2-morpholinol;

(2S,3S)-4-[4-(3-(5-(aminosulfonyl)-4-chloro-2-[(2-furanylmethyl)amino]benzoyloxy)propoxy)(4-oxo)butanoyloxymethoxycarbonyl]-2-(3-chlorophenyl)-3,5,5-trimethyl-2-morpholinol;

(2S,3S)-4-[4-(2-(5-(aminosulfonyl)-4-chloro-2-[(2-furanylmethyl)amino]benzoyloxy)ethoxy)(4-oxo)butanoyloxymethoxycarbonyl]-2-(3-chlorophenyl)-3,5,5-trimethyl-2-morpholinol;

(2S,3S)-4-[4-(4-(5-(aminosulfonyl)-4-chloro-2-[(2-furanylmethyl)amino]benzoyloxy)butoxy)(4-oxo)butanoyloxymethoxycarbonyl]-2-(3-chlorophenyl)-3,5,5-trimethyl-2-morpholinol;

(2S,3S)-4-[4-(5-(5-(aminosulfonyl)-4-chloro-2-[(2-furanylmethyl)amino]benzoyloxy)pentyloxy)(4-oxo)butanoyloxymethoxycarbonyl]-2-(3-chlorophenyl)-3,5,5-trimethyl-2-morpholinol;

(2S,3S)-4-[4-(6-(5-(aminosulfonyl)-4-chloro-2-[(2-furanylmethyl)amino]benzoyloxy)hexyloxy)(4-oxo)butanoyloxymethoxycarbonyl]-2-(3-chlorophenyl)-3,5,5-trimethyl-2-morpholinol;

(2S,3S)-4-[4-(2-(2-(5-(aminosulfonyl)-4-chloro-2-[(2-furanylmethyl)amino]benzoyloxy)ethoxy)ethoxy)(4-oxo)butanoyloxymethoxycarbonyl]-2-(3-chlorophenyl)-3,5,5-trimethyl-2-morpholinol;

(2S,3S)-4-[5-(3-(5-(aminosulfonyl)-4-chloro-2-[(2-furanylmethyl)amino]benzoyloxy)propoxy)(5-oxo)pentanoyloxymethoxycarbonyl]-2-(3-chlorophenyl)-3,5,5-trimethyl-2-morpholinol;

(2S,3S)-4-[5-(2-(5-(aminosulfonyl)-4-chloro-2-[(2-furanylmethyl)amino]benzoyloxy)ethoxy)(5-oxo)pentanoyloxymethoxycarbonyl]-2-(3-chlorophenyl)-3,5,5-trimethyl-2-morpholinol;

(2S,3S)-4-[5-(4-(5-(aminosulfonyl)-4-chloro-2-[(2-furanylmethyl)amino]benzoyloxy)butoxy)(5-oxo)pentanoyloxymethoxycarbonyl]-2-(3-chlorophenyl)-3,5,5-trimethyl-2-morpholinol;

(2S,3S)-4-[5-(5-(5-(aminosulfonyl)-4-chloro-2-[(2-furanylmethyl)amino]benzoyloxy)pentyloxy)(5-oxo)pentanoyloxymethoxycarbonyl]-2-(3-chlorophenyl)-3,5,5-trimethyl-2-morpholinol;

(2S,3S)-4-[5-(6-(5-(aminosulfonyl)-4-chloro-2-[(2-furanylmethyl)amino]benzoyloxy)hexyloxy)(5-oxo)pentanoyloxymethoxycarbonyl]-2-(3-chlorophenyl)-3,5,5-trimethyl-2-morpholinol;

(2S,3S)-4-[5-(2-(2-(5-(aminosulfonyl)-4-chloro-2-[(2-furanylmethyl)amino]benzoyloxy)ethoxy)ethoxy)(5-oxo)pentanoyloxymethoxycarbonyl]-2-(3-chlorophenyl)-3,5,5-trimethyl-2-morpholinol;

2-[(5-(aminosulfonyl)-4-chloro-2-[(2-furanylmethyl)amino]benzoyloxymethoxycarbonyl)(1,1-dimethyl ethyl)amino]-1-(3-chlorophenyl)-1-propanone;

2-[(2-(5-(aminosulfonyl)-4-chloro-2-[(2-furanylmethyl)amino]benzoyloxy)ethanoyloxymethoxycarbonyl)(1,1-dimethylethyl)amino]-1-(3-chlorophenyl)-1-propanone;

2-[(2-(5-(aminosulfonyl)-4-chloro-2-[(2-furanylmethyl)amino]benzoyloxy)propanoyloxymethoxycarbonyl)(1,1-dimethylethyl)amino]-1-(3-chlorophenyl)-1-propanone;

2-[(3-(5-(aminosulfonyl)-4-chloro-2-[(2-furanylmethyl)amino]benzoyloxy)propanoyloxymethoxycarbonyl)(1,1-dimethylethyl)amino]-1-(3-chlorophenyl)-1-propanone;

2-[(2-(5-(aminosulfonyl)-4-chloro-2-[(2-furanylmethyl)amino]benzoyloxy)butanoyloxymethoxycarbonyl)(1,1-dimethylethyl)amino]-1-(3-chlorophenyl)-1-propanone;

2-[(3-(5-(aminosulfonyl)-4-chloro-2-[(2-furanylmethyl)amino]benzoyloxy)butanoyloxymethoxycarbonyl)(1,1-dimethylethyl)amino]-1-(3-chlorophenyl)-1-propanone;

2-[(4-(5-(aminosulfonyl)-4-chloro-2-[(2-furanylmethyl)amino]benzoyloxy)butanoyloxymethoxycarbonyl)(1,1-dimethylethyl)amino]-1-(3-chlorophenyl)-1-propanone;

2-[(4-(5-(aminosulfonyl)-4-chloro-2-[(2-furanylmethyl)amino]benzoyloxy)crotonyloxymethoxycarbonyl)(1,1-dimethylethyl)amino]-1-(3-chlorophenyl)-1-propanone;

2-[(5-(5-(aminosulfonyl)-4-chloro-2-[(2-furanylmethyl)amino]benzoyloxy)pentanoyloxymethoxycarbonyl)(1,1-dimethylethyl)amino]-1-(3-chlorophenyl)-1-propanone;

2-[(6-(5-(aminosulfonyl)-4-chloro-2-[(2-furanylmethyl)amino]benzoyloxy)hexanoyloxymethoxycarbonyl)(1,1-dimethylethyl)amino]-1-(3-chlorophenyl)-1-propanone;

2-[(8-(5-(aminosulfonyl)-4-chloro-2-[(2-furanylmethyl)amino]benzoyloxy)octanoyloxymethoxycarbonyl)(1,1-dimethylethyl)amino]-1-(3-chlorophenyl)-1-propanone;

2-[(2-(2-(5-(aminosulfonyl)-4-chloro-2-[(2-furanylmethyl)amino]benzoyloxy)ethoxy)ethanoyloxymethoxycarbonyl)(1,1-dimethylethyl)amino]-1-(3-chlorophenyl)-1-propanone;

2-[(2-(2-(5-(aminosulfonyl)-4-chloro-2-[(2-furanylmethyl)amino]benzoyloxy)ethylthio)ethanoyloxymethoxycarbonyl)(1,1-dimethylethyl)amino]-1-(3-chlorophenyl)-1-propanone;

2-[(2-(2-(5-(aminosulfonyl)-4-chloro-2-[(2-furanylmethyl)amino]benzoyloxy)ethylsulfinyl)ethanoyloxymethoxycarbonyl)(1,1-dimethylethyl)amino]-1-(3-chlorophenyl)-1-propanone;

2-[(2-(2-(5-(aminosulfonyl)-4-chloro-2-[(2-furanylmethyl)amino]benzoyloxy)ethylsulfonyl)ethanoyloxymethoxycarbonyl)(1,1-dimethylethyl)amino]-1-(3-chlorophenyl)-1-propanone;

2-[(2-((2-(5-(aminosulfonyl)-4-chloro-2-[(2-furanylmethyl)amino]benzoyloxy)ethyl)(methyl)amino)ethanoyloxymethoxycarbonyl) (1,1-dimethylethyl)amino]-1-(3-chlorophenyl)-1-propanone;

2-[(2-(3-(5-(aminosulfonyl)-4-chloro-2-[(2-furanylmethyl)amino]benzoyloxy)propoxy)(2-oxo)ethanoyloxymethoxycarbonyl)(1,1-dimethylethyl)amino]-1-(3-chlorophenyl)-1-propanone;

2-[(2-(2-(5-(aminosulfonyl)-4-chloro-2-[(2-furanylmethyl)amino]benzoyloxy)ethoxy)(2-oxo)ethanoyloxymethoxycarbonyl)(1,1-dimethylethyl)amino]-1-(3-chlorophenyl)-1-propanone;

2-[(2-(4-(5-(aminosulfonyl)-4-chloro-2-[(2-furanylmethyl)amino]benzoyloxy)butoxy)(2-oxo)ethanoyloxymethoxycarbonyl)(1,1-dimethylethyl)amino]-1-(3-chlorophenyl)-1-propanone;

2-[(2-(5-(5-(aminosulfonyl)-4-chloro-2-[(2-furanylmethyl)amino]benzoyloxy)pentyloxy)(2-oxo)ethanoyloxymethoxycarbonyl)(1,1-dimethylethyl)amino]-1-(3-chlorophenyl)-1-propanone;

2-[(2-(6-(5-(aminosulfonyl)-4-chloro-2-[(2-furanylmethyl)amino]benzoyloxy)hexyloxy)(2-oxo)ethanoyloxymethoxycarbonyl)(1,1-dimethylethyl)amino]-1-(3-chlorophenyl)-1-propanone;

2-[(2-(2-(2-(5-(aminosulfonyl)-4-chloro-2-[(2-furanylmethyl)amino]benzoyloxy)ethoxy)ethoxy)(2-oxo)ethanoyloxymethoxycarbonyl)(1,1-dimethylethyl)amino]-1-(3-chlorophenyl)-1-propanone;

2-[(3-(3-(5-(aminosulfonyl)-4-chloro-2-[(2-furanylmethyl)amino]benzoyloxy)propoxy)(3-oxo)propanoyloxymethoxycarbonyl)(1,1-dimethylethyl)amino]-1-(3-chlorophenyl)-1-propanone;

2-[(3-(2-(5-(aminosulfonyl)-4-chloro-2-[(2-furanylmethyl)amino]benzoyloxy)ethoxy)(3-oxo)propanoyloxymethoxycarbonyl)(1,1-dimethylethyl)amino]-1-(3-chlorophenyl)-1-propanone;

2-[(3-(4-(5-(aminosulfonyl)-4-chloro-2-[(2-furanylmethyl)amino]benzoyloxy)butoxy)(3-oxo)propanoyloxymethoxycarbonyl)(1,1-dimethylethyl)amino]-1-(3-chlorophenyl)-1-propanone;

2-[(3-(5-(5-(aminosulfonyl)-4-chloro-2-[(2-furanylmethyl)amino]benzoyloxy)pentyloxy)(3-oxo)propanoyloxymethoxycarbonyl)(1,1-dimethylethyl)amino]-1-(3-chlorophenyl)-1-propanone;

2-[(3-(6-(5-(aminosulfonyl)-4-chloro-2-[(2-furanylmethyl)amino]benzoyloxy)hexyloxy)(3-oxo)propanoyloxymethoxycarbonyl)(1,1-dimethylethyl)amino]-1-(3-chlorophenyl)-1-propanone;

2-[(3-(2-(2-(5-(aminosulfonyl)-4-chloro-2-[(2-furanylmethyl)amino]benzoyloxy)ethoxy)ethoxy)(3-oxo)propanoyloxymethoxycarbonyl)(1,1-dimethylethyl)amino]-1-(3-chlorophenyl)-1-propanone;

2-[(4-(3-(5-(aminosulfonyl)-4-chloro-2-[(2-furanylmethyl)amino]benzoyloxy)propoxy)(4-oxo)butanoyloxymethoxycarbonyl)(1,1-dimethylethyl)amino]-1-(3-chlorophenyl)-1-propanone;

2-[(4-(2-(5-(aminosulfonyl)-4-chloro-2-[(2-furanylmethyl) amino]benzoyloxy)ethoxy)(4-oxo)butanoyloxymethoxycarbonyl)(1,1-dimethylethyl)amino]-1-(3-chlorophenyl)-1-propanone;

2-[(4-(4-(5-(aminosulfonyl)-4-chloro-2-[(2-furanylmethyl) amino]benzoyloxy)butoxy)(4-oxo)butanoyloxymethoxycarbonyl)(1,1-dimethylethyl)amino]-1-(3-chlorophenyl)-1-propanone;

2-[(4-(5-(5-(aminosulfonyl)-4-chloro-2-[(2-furanylmethyl) amino]benzoyloxy)pentyloxy)(4-oxo)butanoyloxymethoxycarbonyl)(1,1-dimethylethyl)amino]-1-(3-chlorophenyl)-1-propanone;

2-[(4-(6-(5-(aminosulfonyl)-4-chloro-2-[(2-furanylmethyl) amino]benzoyloxy)hexyloxy)(4-oxo)butanoyloxymethoxycarbonyl)(1,1-dimethylethyl)amino]-1-(3-chlorophenyl)-1-propanone;

2-[(4-(2-(2-(5-(aminosulfonyl)-4-chloro-2-[(2-furanylmethyl)amino]benzoyloxy)ethoxy)ethoxy)(4-oxo)butanoyloxymethoxycarbonyl)(1,1-dimethylethyl)amino]-1-(3-chlorophenyl)-1-propanone;

2-[(5-(3-(5-(aminosulfonyl)-4-chloro-2-[(2-furanylmethyl) amino]benzoyloxy)propoxy)(5-oxo)pentanoyloxymethoxycarbonyl)(1,1-dimethylethyl)amino]-1-(3-chlorophenyl)-1-propanone;

2-[(5-(2-(5-(aminosulfonyl)-4-chloro-2-[(2-furanylmethyl) amino]benzoyloxy)ethoxy)(5-oxo)pentanoyloxymethoxycarbonyl)(1,1-dimethylethyl)amino]-1-(3-chlorophenyl)-1-propanone;

2-[(5-(4-(5-(aminosulfonyl)-4-chloro-2-[(2-furanylmethyl) amino]benzoyloxy)butoxy)(5-oxo)pentanoyloxymethoxycarbonyl)(1,1-dimethylethyl)amino]-1-(3-chlorophenyl)-1-propanone;

2-[(5-(5-(5-(aminosulfonyl)-4-chloro-2-[(2-furanylmethyl) amino]benzoyloxy)pentyloxy)(5-oxo)pentanoyloxymethoxycarbonyl)(1,1-dimethylethyl)amino]-1-(3-chlorophenyl)-1-propanone;

2-[(5-(6-(5-(aminosulfonyl)-4-chloro-2-[(2-furanylmethyl) amino]benzoyloxy)hexyloxy)(5-oxo)pentanoyloxymethoxycarbonyl)(1,1-dimethylethyl)amino]-1-(3-chlorophenyl)-1-propanone;

2-[(5-(2-(2-(5-(aminosulfonyl)-4-chloro-2-[(2-furanylmethyl)amino]benzoyloxy)ethoxy)ethoxy)(5-oxo)pentanoyloxymethoxycarbonyl)(1,1-dimethylethyl)amino]-1-(3-chlorophenyl)-1-propanone; and pharmaceutically acceptable esters, amides, salts or solvates thereof.

The conjugate compound (I) and their salts and solvates may be prepared in accordance with the methods hereinafter described, or in any manner known in the art for the preparation of compounds of analogous structure.

By way of illustration, therapeutic amine-arylsulfonamide conjugate compounds may be prepared by processes that are known to those skilled in the art of organic synthesis. The following Examples illustrate the present invention but should not be construed as a limitation to the scope thereof.

Prophetic Example 1

Preparation of 2-(1-(3,5-difluorobenzoyl)-(R,S)-ethylamino)-(R)-2-methylethyl 5-(aminosulfonyl)-4-chloro-2-[(2-furanylmethyl)amino]benzoate (220)

Scheme A depicts a synthesis of a therapeutic amine-arylsulfonamide conjugate compound wherein the linking group (W) represents a chemical bond. The free base of (2S,3S,5R)-2-(3,5-difluorophenyl)-3,5-dimethyl-2-morpholinol (20a) and/or (20b) (0.023 mole) (U.S. Pat. No. 5,104,870) and benzene (30 mL) (or toluene) is added to a round-bottomed flask. Furosemide (5-(aminosulfonyl)-4-chloro-2-[(2-furanylmethyl)amino]benzoic acid, (10) (Aldrich) (0.025 mole), benzene (30 mL), and p-toluenesulfonic acid (0.026 mole) catalyst is added to the flask. A Dean-Stark trap is filled with benzene, and the contents of the flask is refluxed with stirring for several hours or until no additional water is collected in the trap. The reaction is cooled, extracted with sodium bicarbonate solution, washed with water, and then with a saturated sodium chloride solution. The organic layer is dried over sodium sulfate, filtered and concentrated in vacuo to give crude product, which may be purified by column chromatography on silica gel with hexanes/ethyl acetate as eluent. The fractions that contain pure product may be combined and spin evaporated in vacuo to give a solid that may be recrystallized to give 2-(1-(3,5-difluorobenzoyl)-(R, S)-ethylamino)-(R)-2-methylethyl 5-(aminosulfonyl)-4-chloro-2-[(2-furanylmethyl)amino]benzoate (220). See eg., Sandler et al., Organic Functional Group Preparations, p. 249 (1968).

SCHEME A

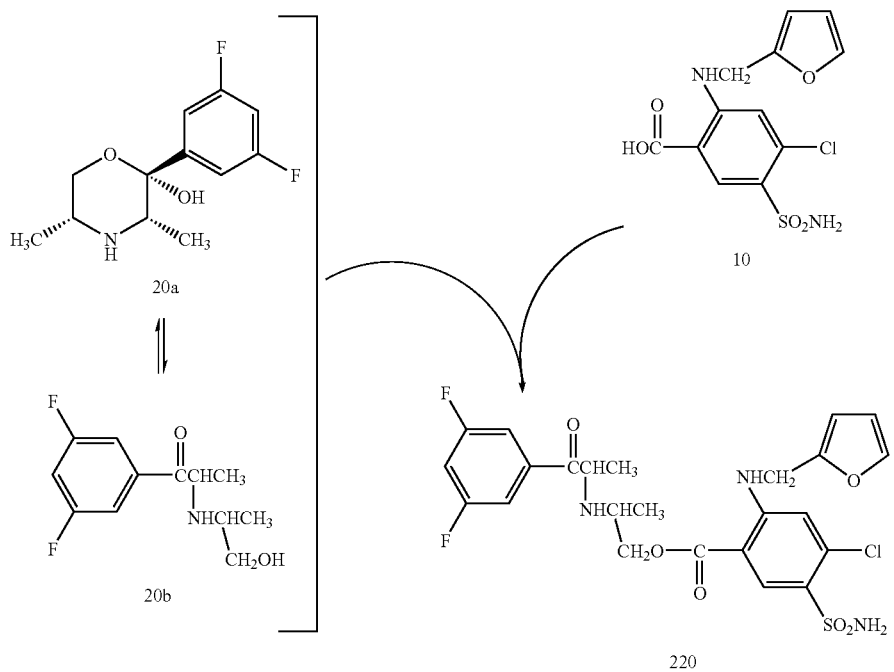

The following conjugate compound may be prepared by the same general method:
2-(1-(3-chlorobenzoyl)-(R,S)-ethylamino)-2,2-dimethylethyl 5-(aminosulfonyl)-4-chloro-2-[(2-furanylmethyl)amino]benzoate.

Prophetic Example 2

Alternate preparation of 2-(1-(3,5-difluorobenzoyl)-(R,S)-ethylamino)-(R)-2-methylethyl 5-(aminosulfonyl)-4-chloro-2-[(2-furanylmethyl)amino]benzoate (220)

Scheme B depicts an alternate synthesis of a therapeutic amine-arylsulfonamide conjugate compound (220) as previously described in Example 1 by a three step process (a-c), wherein the linker (W) is a chemical bond, by way of reduction of the morpholinol group of the therapeutic amine, esterification with the arylsulfonamide, followed by oxidation of the difluorophenyl hydroxyl group to prepare the conjugate compound.

a Preparation of (rac)-(R*,S*)-2-((2-hydroxy-(R)-1-methylethyl)amino)-1-(3,5-difluorophenyl)propanol The hydrobromide salt of (2S,3S,5R)-2-(3,5-difluorophenyl)-3,5-dimethyl-2-morpholinol (0.023 mole) (U.S. Pat. No. 5,104,870) is dissolved in a 50:50 mixture of ethanol/water (150 mL) and chilled to 0° C. while being stirred under a nitrogen atmosphere. A solution of sodium borohydride (0.093 mole) in water (25 mL) is added dropwise, and the solution is allowed to warm to room temperature while being stirred overnight. The solution is cooled to 0° C., and concentrated hydrochloric acid (25 mL) is carefully added dropwise. The mixture is concentrated under reduced pressure to remove ethanol and then diluted with water to dissolve the solids. This solution is cooled with an ice bath, made basic by treatment with 40% aqueous sodium hydroxide and extracted three times with diethyl ether. The combined ether extracts is washed with a saturated sodium chloride solution, dried over sodium sulfate and spin evaporated in vacuo to give the free base of (rac)-(R*,S*)-2-((2-hydroxy-(R)-1-methylethyl)amino)-1-(3,5-difluorophenyl)propanol (21). A sample of the free base is treated with ethereal hydrogen chloride to give a solid that may be recrystallized from ethanol/ether to give the hydrochloride salt of (rac)-(R*,S*)-2-((2-hydroxy-(R)-1-methylethyl)amino)-1-(3,5-difluorophenyl)propanol. See eg., Boswell et al., *J. Heterocyclic Chem.*, (1996) 33:33.

b Preparation of (rac)-(R*,S*)-2-((2-(3,5-difluorophenyl)-2-hydroxy-1-methylethyl)amino)-(R)-2-methylethyl 5-(aminosulfonyl)-4-chloro-2-[(2-furanylmethyl)amino]benzoate The free base of (rac)-(R*,S*)-2-((2-hydroxy-(R)-1-methylethyl)amino)-1-(3,5-difluorophenyl)propanol (21) (0.023 mole) and benzene (30 mL) (or toluene) is added to a round-bottomed flask. Furosemide (5-(aminosulfonyl)-4-chloro-2-[(2-furanylmethyl)amino]benzoic acid (10), (Aldrich) (0.025 mole), benzene (30 mL), and p-toluenesulfonic acid (0.026 mole) catalyst is added to the flask. A Dean-Stark trap is filled with benzene, and the contents of the flask is refluxed with stirring for several hours or until no additional water is collected in the trap. The reaction is cooled, extracted with sodium bicarbonate solution, washed with water, and then with a saturated sodium chloride solution. The organic layer is dried over sodium sulfate, filtered and concentrated in vacuo to give crude product, which may be purified by column chromatography on silica gel with hexanes/ethyl acetate as eluent. The fractions that contain pure product may be combined and spin evaporated in vacuo to give a solid that may be recrystallized to give (rac)-(R*,S*)-2-((2-(3,5-difluorophenyl)-2-hydroxy-1-methylethyl)amino)-(R)-2-methylethyl 5-(aminosulfonyl)-4-chloro-2-[(2-furanylmethyl)amino]benzoate (210). [See eg., Sandier et al., Organic Functional Group Preparations, p. 249 (1968)]

c Preparation of 2-(1-(3,5-difluorobenzoyl)-(R,S)-ethylamino)-(R)-2-methylethyl 5-(aminosulfonyl)-4-chloro-2-[(2-furanylmethyl)amino]benzoate 5-(aminosulfonyl)-4-chloro-2-[(2-furanylmethyl)amino]benzoate (220). See eg., Sandler et al., Organic Functional Group Preparations, p. 171 (1968).

The following conjugate compound may be prepared by the same general method:

2-(1-(3-chlorobenzoyl)-(R,S)-ethylamino)-2,2-dimethylethyl 5-(aminosulfonyl)-4-chloro-2-[(2-furanylmethyl)amino]benzoate.

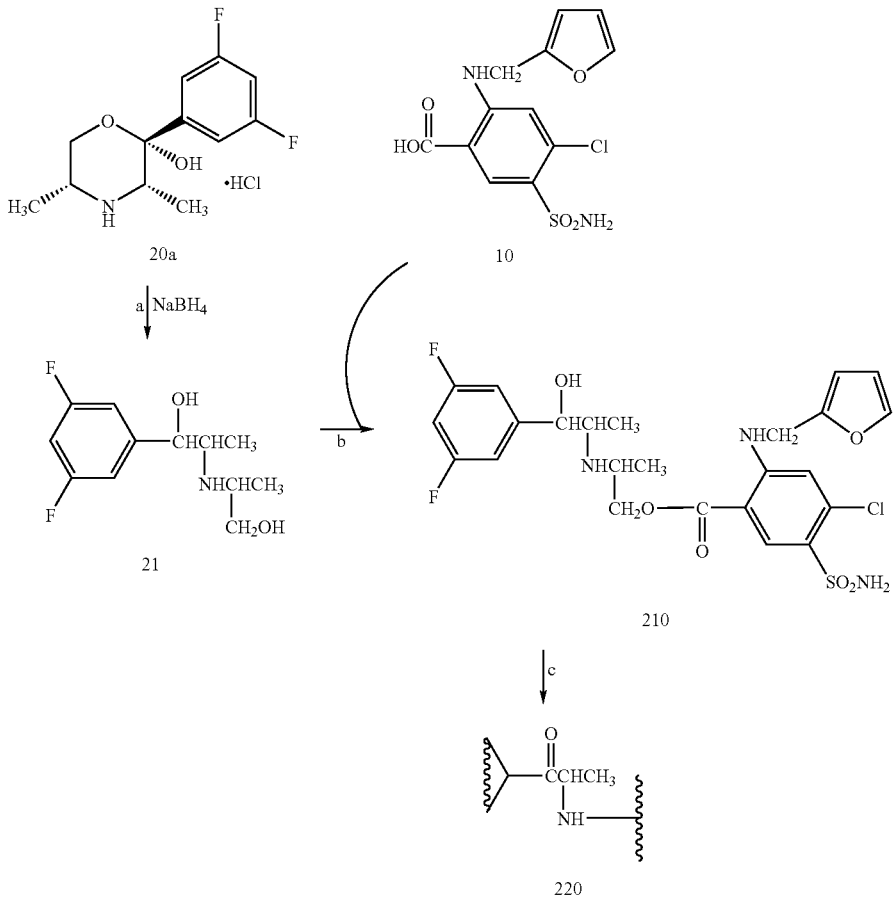

A solution of chromic oxide (9.2 mmole) in 80% acetic acid (10 mL) is added to a stirred solution of (rac)-(R*,S*)-2-((2-(3,5-difluorophenyl)-2-hydroxy-1-methylethyl)amino)-(R)-2-methylethyl 5-(aminosulfonyl)-4-chloro-2-[(2-furanylmethyl)amino]benzoate (210) (18 mmole) in glacial acetic acid (10 mL) at a rate as to maintain a temperature of 50° C. The mixture is allowed to stand for 24 hours and then extracted with benzene (three 20 mL portions). The combined extracts is washed with sodium bicarbonate solution, with water, and then with a saturated sodium chloride solution. The organic layer is dried over sodium sulfate, filtered and concentrated in vacuo to give crude product, which may be purified by column chromatography on silica gel with hexanes/ethyl acetate as eluent. The fractions that contain pure product may be combined and spin evaporated in vacuo to give a white solid that may be recrystallized to give 2-(1-(3,5-difluorobenzoyl)-(R,S)-ethylamino)-(R)-2-methylethyl Prophetic Example 3

Scheme C, synthetic route (i) depicts a synthesis of a therapeutic amine-arylsulfonamide conjugate compound wherein the linker (W) is —C(O)R$^1$O—; where R$^1$ is —(CH$_2$)$_n$—; and n is 3.

Preparation of 2-(1-(3,5-difluorobenzoyl)-(R,S)-ethylamino)-(R)-2-methylethyl 4-(5-(aminosulfonyl)-4-chloro-2-[(2-furanylmethyl)amino]benzoyloxy)butanoate (320)

A mixture of furosemide (5-(aminosulfonyl)-4-chloro-2-[(2-furanylmethyl)amino]benzoic acid (10), (Aldrich) (0.060 mole), ethyl 4-bromobutyrate (Aldrich) (0.055 mole), DBN (1,5-diazabicyclo[4.3.0]non-5-ene, Aldrich) (0.060 mole) and dry acetonitrile (100 mL) is stirred at ambient temperature for 10 hours. The reaction mixture is diluted with dichloromethane (200 mL) and extracted with sodium bicarbonate solution, washed with water, and then with a saturated sodium chloride solution. The organic layer is dried over sodium sulfate, filtered and concentrated in vacuo to give crude product, which may be purified by column chromatography on silica gel with hexanes/ethyl acetate as eluent. The fractions that contain pure product may be combined and spin evaporated in vacuo to give ethyl 4-(5-(aminosulfonyl)-4-chloro-2-[(2-furanylmethyl)amino]benzoyloxy)butanoate (300). See eg., T. W. Greene and P. G. M. Wuts, Protective Groups in Organic Synthesis, p. 228 (1991).

with a saturated sodium chloride solution. The organic layer is dried over sodium sulfate, filtered and concentrated in vacuo to give crude product, which may be purified by column chromatography on silica gel with hexanes/ethyl acetate as eluent. The fractions that contain pure product may be combined and spin evaporated in vacuo to give a solid that may be recrystallized to give 2-(1-(3,5-difluorobenzoyl)-(R,S)-ethylamino)-(R)-2-methylethyl 4-(5-(aminosulfonyl)-4-chloro-2-[(2-furanylmethyl)amino]benzoyloxy)butanoate (320). See eg., Sandler et al., Organic Functional Group Preparations, p. 249 (1968).

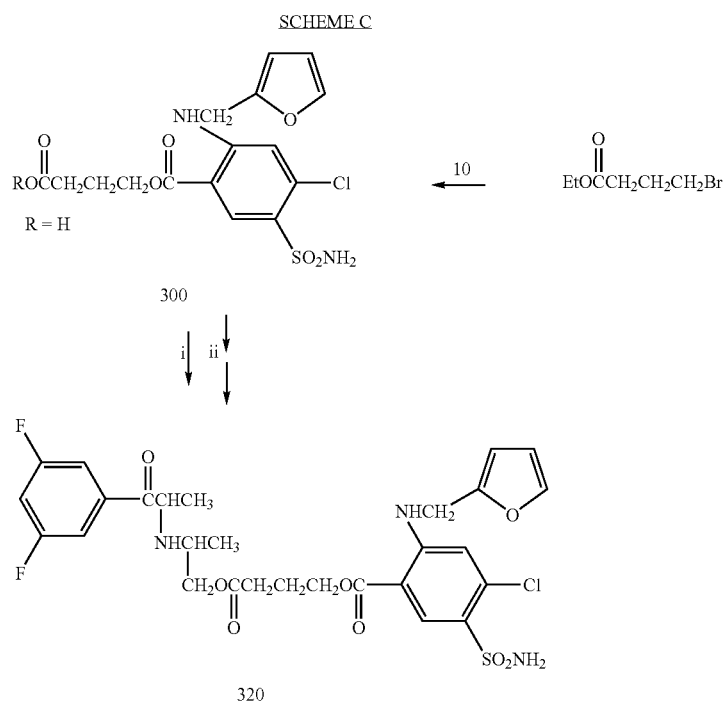

A mixture of ethyl 4-(5-(aminosulfonyl)-4-chloro-2-[(2-furanylmethyl)amino]benzoyloxy)butanoate (300) (0.060 mole) in ethanol (100 mL) is cooled in an ice water bath. A solution of 1.0 N sodium hydroxide (60 mL) is added dropwise with stirring, and the reaction is stirred for 12 hours at ambient temperature. The volatiles is removed by spin evaporation in vacuo. The residue is dissolved in cold water, and the solution is washed with diethyl ether. The aqueous solution is cooled in an ice bath and acidified by dropwise addition of 1.0 N hydrochloric acid solution (60 mL). The resulting solid may be collected and recrystallized to give 4-(5-(aminosulfonyl)-4-chloro-2-[(2-furanylmethyl)amino]benzoyloxy)butanoic acid.

The free base of (2S,3S,5R)-2-(3,5-difluorophenyl)-3,5-dimethyl-2-morpholinol (0.023 mole) (U.S. Pat. No. 5,104,870) and benzene (30 mL) (or toluene) is added to a round-bottomed flask. 4-(5-(Aminosulfonyl)-4-chloro-2-[(2-furanylmethyl)amino]benzoyloxy)butanoic acid (0.025 mole), benzene (30 mL), and p-toluenesulfonic acid (0.026 mole) catalyst is added to the flask. A Dean-Stark trap is filled with benzene, and the contents of the flask is refluxed with stirring for several hours or until no additional water is collected in the trap. The reaction is cooled, extracted with sodium bicarbonate solution, washed with water, and then The following conjugate compounds may be prepared, for example, by the same general method as described above in Example 3 and depicted in Scheme C:

2-(1-(3-chlorobenzoyl)-(R,S)-ethylamino)-2,2-dimethylethyl 4-(5-(aminosulfonyl)-4-chloro-2-[(2-furanylmethyl) amino]benzoyloxy)butanoate;

2-(1-(3,5-difluorobenzoyl)-(R,S)-ethylamino)-(R)-2-methylethyl 2-(5-(aminosulfonyl)-4-chloro-2-[(2-furanylmethyl)amino]benzoyloxy)ethanoate;

2-(1-(3,5-difluorobenzoyl)-(R,S)-ethylamino)-(R)-2-methylethyl 3-(5-(aminosulfonyl)-4-chloro-2-[(2-furanylmethyl)amino]benzoyloxy)propanoate;

2-(1-(3,5-difluorobenzoyl)-(R,S)-ethylamino)-(R)-2-methylethyl 2-(5-(aminosulfonyl)-4-chloro-2-[(2-furanylmethyl)amino]benzoyloxy)propanoate;

2-(1-(3,5-difluorobenzoyl)-(R,S)-ethylamino)-(R)-2-methylethyl 4-(5-(aminosulfonyl)-4-chloro-2-[(2-furanylmethyl)amino]benzoyloxy)crotonate;

2-(1-(3,5-difluorobenzoyl)-(R,S)-ethylamino)-(R)-2-methylethyl 5-(5-(aminosulfonyl)-4-chloro-2-[(2-furanylmethyl)amino]benzoyloxy)pentanoate;

2-(1-(3,5-difluorobenzoyl)-(R,S)-ethylamino)-(R)-2-methylethyl 6-(5-(aminosulfonyl)-4-chloro-2-[(2-furanylmethyl)amino]benzoyloxy)hexanoate;

2-(1-(3,5-difluorobenzoyl)-(R,S)-ethylamino)-(R)-2-methylethyl 8-(5-(aminosulfonyl)-4-chloro-2-[(2-furanylmethyl)amino]benzoyloxy)octanoate;

2-(1-(3,5-difluorobenzoyl)-(R,S)-ethylamino)-(R)-2-methylethyl 2-(2-(5-(aminosulfonyl)-4-chloro-2-[(2-furanylmethyl)amino]benzoyloxy)ethoxy)ethanoate;

2-(1-(3,5-difluorobenzoyl)-(R,S)-ethylamino)-(R)-2-methylethyl 2-(2-(5-(aminosulfonyl)-4-chloro-2-[(2-furanylmethyl)amino]benzoyloxy)ethylthio)ethanoate;

2-(1-(3,5-difluorobenzoyl)-(R,S)-ethylamino)-(R)-2-methylethyl 2-(2-(5-(aminosulfonyl)-4-chloro-2-[(2-furanylmethyl)amino]benzoyloxy)ethylsulfinyl)ethanoate;

2-(1-(3,5-difluorobenzoyl)-(R,S)-ethylamino)-(R)-2-methylethyl 2-(2-(5-(aminosulfonyl)-4-chloro-2-[(2-furanylmethyl)amino]benzoyloxy)ethylsulfonyl)ethanoate;

2-(1-(3,5-difluorobenzoyl)-(R,S)-ethylamino)-(R)-2-methylethyl 2-((2-(5-(aminosulfonyl)-4-chloro-2-[(2-furanylmethyl)amino]benzoyloxy)ethyl)(methyl)amino)ethanoate; and 2-(1-(3,5-difluorobenzoyl)-(R,S)-ethylamino)-(R)-2-methylethyl 4-(5-(aminosulfonyl)-4-chloro-2-[(2-furanylmethyl)amino]benzoyloxy)(2-fluoro)butanoate.

Prophetic Example 4

Scheme C, synthetic route (ii) depicts an alternate synthesis of a therapeutic amine-arylsulfonamide conjugate compound (320) having a linker (W) that is —C(O)R$^1$O—; where R$^1$ is —(CH$_2$)$_n$—; and n is 3.

Preparation of 2-(1-(3,5-difluorobenzoyl)-(R,S)-ethylamino)-(R)-2-methylethyl 4-(5-(aminosulfonyl)-4-chloro-2-[(2-furanylmethyl)amino]benzoyloxy)butanoate (320)

Preparation of (rac)-(R*,S*)-2-((2-(3,5-difluorophenyl)-2-hydroxy-1-methylethyl)amino)-(R)-2-methylethyl 4-(5-(aminosulfonyl)-4-chloro-2-[(2-furanylmethyl)amino]benzoyloxy)butanoate The free base of (rac)-(R*,S*)-2-((2-hydroxy-(R)-1-methylethyl)amino)-1-(3,5-difluorophenyl)propanol (21) (0.023 mole) and benzene (30 mL) (or toluene) is added to a round-bottomed flask. 4-(5-(Aminosulfonyl)-4-chloro-2-[(2-furanylmethyl)amino]benzoyloxy)butanoic acid (0.025 mole), benzene (30 mL), and p-toluenesulfonic acid (0.026 mole) catalyst is added to the flask. A Dean-Stark trap is filled with benzene, and the contents of the flask is refluxed with stirring for several hours or until no additional water is collected in the trap. The reaction is cooled, extracted with sodium bicarbonate solution, washed with water, and then with a saturated sodium chloride solution. The organic layer is dried over sodium sulfate, filtered and concentrated in vacuo to give crude product, which may be purified by column chromatography on silica gel with hexanes/ethyl acetate as eluent. The fractions that contain pure product may be combined and spin evaporated in vacuo to give a solid that may be recrystallized to give (rac)-(R*,S*)-2-((2-(3,5-difluorophenyl)-2-hydroxy-1-methylethyl)amino)-(R)-2-methylethyl 4-(5-(aminosulfonyl)-4-chloro-2-[(2-furanylmethyl)amino]benzoyloxy)butanoate. See eg., Sandler et al., Organic Functional Group Preparations, p. 249 (1968).

Preparation of 2-(1-(3,5-difluorobenzoyl)-(R,S)-ethylamino)-(R)-2-methylethyl 4-(5-(aminosulfonyl)-4-chloro-2-[(2-furanylmethyl)amino]benzoyloxy)butanoate (320)

A solution of chromium trioxide (10 mmole) and 1.6 mL of concentrated sulfuric acid in water (5 mL) is added dropwise to an ice water bath cooled, stirred solution of (rac)-(R*,S*)-2-((2-(3,5-difluorophenyl)-2-hydroxy-1-methylethyl)amino)-(R)-2-methylethyl 4-(5-(aminosulfonyl)-4-chloro-2-[(2-furanylmethyl)amino]benzoyloxy)butanoate (19 mmole) in water (5 mL) and dichloromethane (10 mL). The reaction is stirred at ambient temperature for 1 hour and then dichloromethane (20 mL) is added. The mixture is stirred for 15 minutes, and the organic layer is separated. The aqueous layer is extracted with dichloromethane (two 10 mL portions). The combined organic extracts is washed with sodium bicarbonate solution, with water, and then with a saturated sodium chloride solution. The organic layer is dried over sodium sulfate, filtered and concentrated in vacuo to give crude product, which may be purified by column chromatography on silica gel with hexanes/ethyl acetate as eluent. The fractions that contain pure product may be combined and spin evaporated in vacuo to give a solid that may be recrystallized to give 2-(1-(3,5-difluorobenzoyl)-(R,S)-ethylamino)-(R)-2-methylethyl 4-(5-(aminosulfonyl)-4-chloro-2-[(2-furanylmethyl)amino]benzoyloxy)butanoate (320). See eg., Org. Syn. Coll. (1973) 5:324.

The following conjugate compound may be prepared by the same general method:

2-(1-(3-chlorobenzoyl)-(R,S)-ethylamino)-2,2-dimethylethyl 4-(5-(aminosulfonyl)-4-chloro-2-[(2-furanylmethyl)amino]benzoyloxy)butanoate.

Prophetic Example 5

Scheme D depicts a synthesis of a therapeutic amine-arylsulfonamide conjugate compound wherein the linker (W) is —CH$_2$O—.

Preparation of (2S,3S,5R)-4-(5-(aminosulfonyl)-4-chloro-2-[(2-furanylmethyl)amino]benzoyloxymethyl)-2-(3,5-difluorophenyl)-3,5-dimethyl-2-morpholinol (520)

a Preparation of 5-(aminosulfonyl)-4-chloro-2-[(2-furanylmethyl)amino]benzoyl chloride (13)

A solution of oxalyl chloride (0.040 mole) in dichloromethane (20 mL) is added dropwise to an ice bath cooled solution of furosemide (5-(aminosulfonyl)-4-chloro-2-[(2-furanylmethyl)amino]benzoic acid), (10) (Aldrich) (0.040 mole) in dichloromethane (50 mL). The reaction is stirred at ambient temperature for 5 hours. The reaction solution is washed with 5% aqueous sodium bicarbonate, with water, and then with a saturated sodium chloride solution. The organic layer is dried over sodium sulfate, filtered and may be concentrated in vacuo to give 5-(aminosulfonyl)-4-chloro-2-[(2-furanylmethyl)amino]benzoyl chloride (13). See eg., Musso, et. al., J. Med. Chem., (2003) 46:409.

b Preparation of chloromethyl 5-(aminosulfonyl)-4-chloro-2-[(2-furanylmethyl)amino]benzoate (15)

A mixture of 5-(aminosulfonyl)-4-chloro-2-[(2-furanylmethyl)amino]benzoyl chloride (13) (0.040 mole) and paraformaldehyde (0.040 mole) is heated in a sealed vessel at 90° C. for 3 hours. The reaction is cooled, and the solids is dissolved in dichloromethane. The solution is washed with 5% aqueous sodium bicarbonate, with water, and then with a saturated sodium chloride solution. The organic layer is dried over sodium sulfate, filtered and concentrated in vacuo to give crude product, which may be purified by column chromatography on silica gel with hexanes/ethyl acetate as eluent. The fractions that contain pure product may be combined and spin evaporated in vacuo to give chloromethyl 5-(aminosulfonyl)-4-chloro-2-[(2-furanylmethyl)amino]benzoate (15). See eg., Bodor, et al., *J. Med. Chem.*, (1980) 23: 469, and Ulich et al., *J. Am. Chem. Soc.*, (1921) 43: 660.

fied by column chromatography on silica gel with hexanes/ethyl acetate as eluent. The fractions that contain pure product may be combined and spin evaporated in vacuo to give a solid that may be recrystallized to give (2S,3S,5R)-4-(5-(aminosulfonyl)-4-chloro-2-[(2-furanylmethyl)amino]benzoyloxymethyl)-2-(3,5-difluorophenyl)-3,5-dimethyl-2-morpholinol (520). See eg., U.S. Pat. No. 5,104,870) and Sandler, et al., Organic Functional Group Preparations, p. 324 (1968).

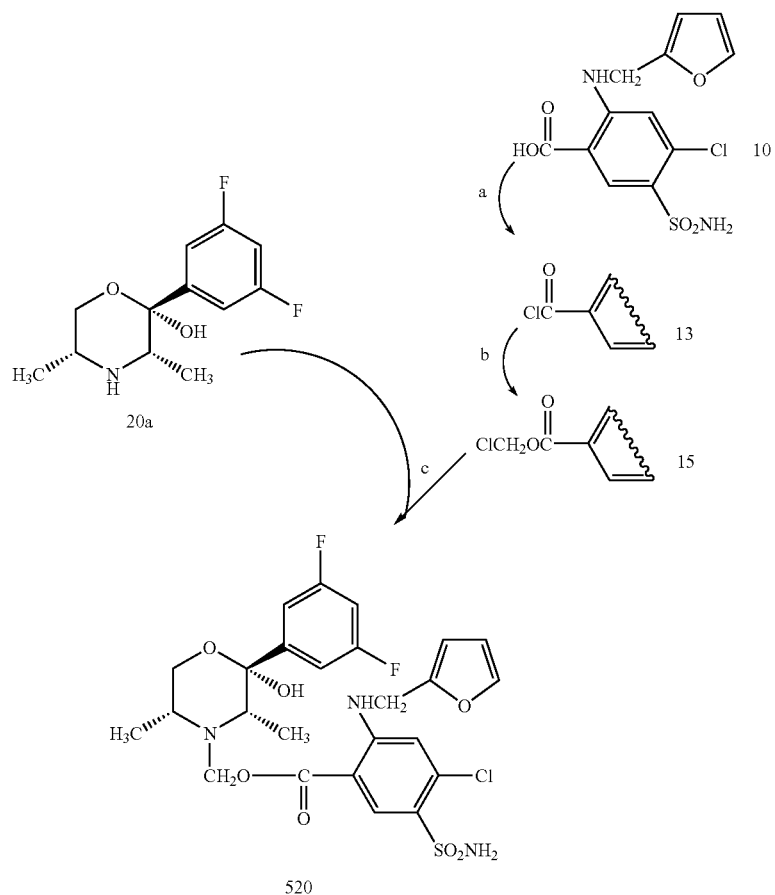

c Preparation of (2S,3S,5R)-4-(5-(aminosulfonyl)-4-chloro-2-[(2-furanylmethyl)amino]benzoyloxymethyl)-2-(3,5-difluorophenyl)-3,5-dimethyl-2-morpholinol (520)

A solution of free base of (2S,3S,5R)-2-(3,5-difluorophenyl)-3,5-dimethyl-2-morpholinol (20a) (0.023 mole) (U.S. Pat. No. 5,104,870), triethylamine (0.055 mole) and acetonitrile (30 mL) is stirred with cooling on an ice bath. A solution of chloromethyl 5-(aminosulfonyl)-4-chloro-2-[(2-furanylmethyl)amino]benzoate (15) (0.025 mole) in acetonitrile (30 mL) is added dropwise. After the addition is complete, the reaction is heated to reflux for 2 hours. The reaction is cooled, the volatiles removed by spin evaporation, and the residue partitioned between dichloromethane and 5% aqueous sodium bicarbonate. The organic layer is washed with water, and then with a saturated sodium chloride solution. The organic layer is dried over sodium sulfate, filtered and concentrated in vacuo to give crude product, which may be puri- The following conjugate compounds may be prepared, for example, by the same general method:
(2S,3S)-4-(5-(aminosulfonyl)-4-chloro-2-[(2-furanylmethyl)amino]benzoyloxymethyl)-2-(3 chlorophenyl)-3,5,5-trimethyl-2-morpholinol;
(2S,3S,5R)-4-(1-(5-(aminosulfonyl)-4-chloro-2-[(2-furanylmethyl)amino]benzoyloxy)-(R,S)-ethyl)-2-(3,5-difluorophenyl)-3,5-dimethyl-2-morpholinol; and
(2S,3S)-4-(1-(5-(aminosulfonyl)-4-chloro-2-[(2-furanylmethyl)amino]benzoyloxy)-(R,S)-ethyl)-2-(3-chlorophenyl)-3,5,5-trimethyl-2-morpholinol.

Prophetic Example 6

Scheme E depicts a synthesis of a therapeutic amine-arylsulfonamide conjugate compound wherein the linker (W) is —CHROC(O)R$^1$O—; where R is H; R$^1$ is —(CH$_2$)$_n$—; and where n is 3.

Preparation of (2S,3S,5R)-4-[4-(5-(aminosulfonyl)-

4-chloro-2-[(2-furanylmethyl)amino]benzoyloxy) butanoyloxymethyl]-2-(3,5-difluorophenyl)-3,5-dimethyl-2-morpholinol (620)

a Preparation of 4-(5-(aminosulfonyl)-4-chloro-2-[(2-furanylmethyl)amino]benzoyloxy)butanoyl chloride (313)

A solution of oxalyl chloride (0.040 mole) in dichloromethane (20 mL) is added dropwise to an ice bath cooled solution of 4-(5-(aminosulfonyl)-4-chloro-2-[(2-furanylmethyl)amino]benzoyloxy)butanoic acid (300) (0.040 mole) in dichloromethane (50 mL). The reaction is stirred at ambient temperature for 5 hours. The reaction solution is washed with 5% aqueous sodium bicarbonate, with water, and then with a saturated sodium chloride solution. The organic layer is dried over sodium sulfate, filtered and concentrated in vacuo to give 4-(5-(aminosulfonyl)-4-chloro-2-[(2-furanylmethyl)amino] benzoyloxy)butanoyl chloride (313). See eg., D. L. Musso, et. al., *J. Med. Chem.*, (2003) 46: 409.

b Preparation of chloromethyl 4-(5-(aminosulfonyl)-4-chloro-2-[(2-furanylmethyl)amino]benzoyloxy) butanoate (315)

A mixture of 4-(5-(aminosulfonyl)-4-chloro-2-[(2-furanylmethyl)amino]benzoyloxy)butanoyl chloride (313) (0.040 mole) and paraformaldehyde (0.040 mole) is heated in a sealed vessel at 90° C. for 3 hours. The reaction is cooled, and the solids dissolved in dichloromethane. The solution is washed with 5% aqueous sodium bicarbonate, with water, and then with a saturated sodium chloride solution. The organic layer is dried over sodium sulfate, filtered and concentrated in vacuo to give crude product, which may be purified by column chromatography on silica gel with hexanes/ethyl acetate as eluent. The fractions that contain pure product may be combined and spin evaporated in vacuo to give chloromethyl 4-(5-(aminosulfonyl)-4-chloro-2-[(2-furanylmethyl)amino]benzoyloxy)butanoate (315). See eg., Bodor, et al., *J. Med. Chem.*, 23, 469 (1980), and Ulich, et al., *J. Am. Chem. Soc.*, (1921) 43: 660.

c Preparation of (2S,3S,5R)-4-[4-(5-(aminosulfonyl)-4-chloro-2-[(2-furanylmethyl)amino]benzoyloxy)butanoyloxymethyl]-2-(3,5-difluorophenyl)-3, 5-dimethyl-2-morpholinol (620)

A solution of the free base of (2S,3S,5R)-2-(3,5-difluorophenyl)-3,5-dimethyl-2-morpholinol (20a (0.023 mole) (U.S. Pat. No. 5,104,870), triethylamine (0.025 mole) and acetonitrile (30 mL) is stirred with cooling on an ice bath. A solution of chloromethyl 4-(5-(aminosulfonyl)-4-chloro-2-[(2-furanylmethyl)amino]benzoyloxy)butanoate (315) (0.025 mole) in acetonitrile (30 mL) is added dropwise. After the addition is complete, the reaction is heated to reflux for 2 hours. The reaction is cooled, the volatiles removed by spin evaporation, and the residue partitioned between dichloromethane and 5% aqueous sodium bicarbonate. The organic layer is washed with water, and then with a saturated sodium chloride solution. The organic layer is dried over sodium sulfate, filtered and concentrated in vacuo to give crude product, which may be purified by column chromatography on silica gel with hexanes/ethyl acetate as eluent. The fractions that contain pure product may be combined and spin evaporated in vacuo to give a solid that may be recrystallized to give (2S,3S,5R)-4-[4-(5-(aminosulfonyl)-4-chloro-2-[(2-furanylmethyl)amino]benzoyloxy)butanoyloxymethyl]-2-(3,5-difluorophenyl)-3,5-dimethyl-2-morpholinol (620). See eg., U.S. Pat. No. 5,104,870 and Sandler, et al., Organic Functional Group Preparations, p. 324 (1968).

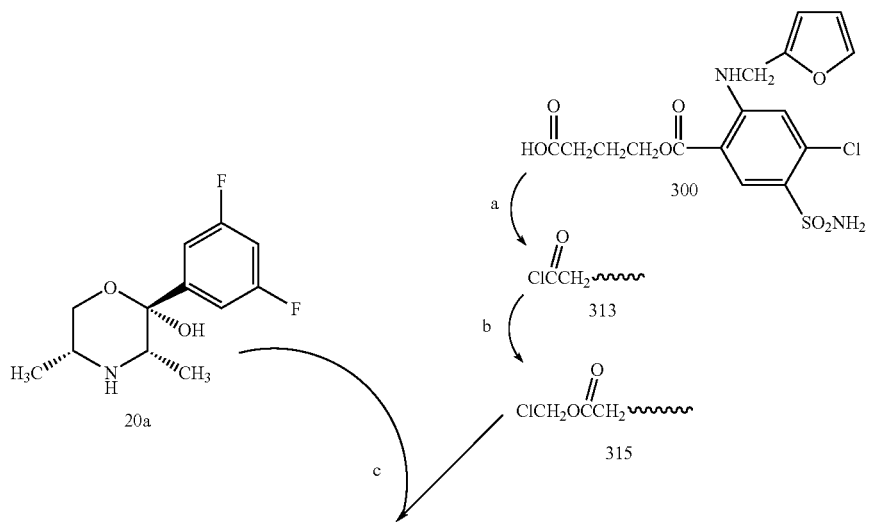

-continued

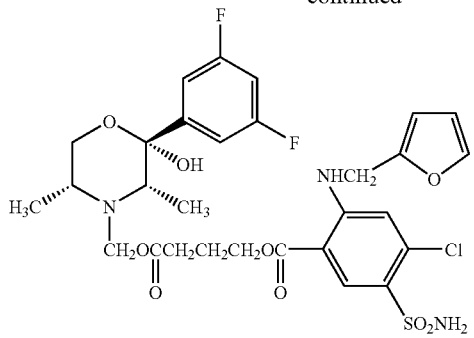

620

The following conjugate compounds may be prepared, for example, by the same general method:
(2S,3S,5R)-4-[1-(4-(5-(aminosulfonyl)-4-chloro-2-[(2-furanylmethyl)amino]benzoyloxy)butanoyloxy)-(R,S)-ethyl]-2-(3,5-difluorophenyl)-3,5-dimethyl-2-morpholinol;
(2S,3S)-4-[1-(4-(5-(aminosulfonyl)-4-chloro-2-[(2-furanylmethyl)amino]benzoyloxy)butanoyloxy)-(R,S)-ethyl]-2-(3-chlorophenyl)-3,5,5-trimethyl-2-morpholinol; and
2-[(1-(4-(5-(aminosulfonyl)-4-chloro-2-[(2-furanylmethyl)amino]benzoyloxy)butanoyloxy)-(R,S)-ethyl)(1,1-dimethylethyl)amino]-1-(3-chlorophenyl)-1-propanone.

Prophetic Example 7

Scheme F depicts a synthesis of a therapeutic amine-arylsulfonamide conjugate compound wherein the linker (W) is —CH$_2$O—.

Preparation of 2-[(5-(aminosulfonyl)-4-chloro-2-[(2-furanylmethyl)amino]benzoyloxymethyl)(1,1-dimethylethyl)amino]-1-(3-chlorophenyl)-1-propanone (720)

a Preparation of 5-(aminosulfonyl)-4-chloro-2-[(2-furanylmethyl)amino]benzoyl chloride (13)

A solution of oxalyl chloride (0.040 mole) in dichloromethane (20 mL) is added dropwise to an ice bath cooled solution of furosemide (5-(aminosulfonyl)-4-chloro-2-[(2-furanylmethyl)amino]benzoic acid), (10) (Aldrich) (0.040 mole) in dichloromethane (50 mL). The reaction is stirred at ambient temperature for 5 hours. The reaction solution is washed with 5% aqueous sodium bicarbonate, with water, and then with a saturated sodium chloride solution. The organic layer is dried over sodium sulfate, filtered and concentrated in vacuo to give 5-(aminosulfonyl)-4-chloro-2-[(2-furanylmethyl)amino]benzoyl chloride (13). See eg., D. L. Musso, et. al., J. Med. Chem., (2003) 46: 409.

b Preparation of chloromethyl 5-(aminosulfonyl)-4-chloro-2-[(2-furanylmethyl)amino]benzoate (15)

A mixture of 5-(aminosulfonyl)-4-chloro-2-[(2-furanylmethyl)amino]benzoyl chloride (13) (0.040 mole) and paraformaldehyde (0.040 mole) is heated in a sealed vessel at 90° C. for 3 hours. The reaction is cooled, and the solids dissolved in dichloromethane. The solution is washed with 5% aqueous sodium bicarbonate, with water, and then with a saturated sodium chloride solution. The organic layer is dried over sodium sulfate, filtered and concentrated in vacuo to give crude product, which may be purified by column chromatography on silica gel with hexanes/ethyl acetate as eluent. The fractions that contain pure product may be combined and spin evaporated in vacuo to give chloromethyl 5-(aminosulfonyl)-4-chloro-2-[(2-furanylmethyl)amino]benzoate (15). See eg., Bodor, et al., J. Med. Chem., 23, 469 (1980), and Ulich, et al., J. Am. Chem. Soc., (1921) 43: 660.

c Preparation of 2-[(5-(aminosulfonyl)-4-chloro-2-[(2-furanylmethyl)amino]benzoyloxymethyl)(1,1-dimethylethyl)amino]-1-(3-chlorophenyl)-1-propanone (720)

A solution of bupropion[1-(3-chlorophenyl)-2-[(1,1-dimethylethyl)amino]-1-propanone hydrochloride (700), (U.S. Pat. No. 3,819,706 and U.S. Pat. No. 3,885,046) (0.025 mole), triethylamine (0.055 mole) and acetonitrile (30 mL) is stirred with cooling on an ice bath. A solution of chloromethyl 5-(aminosulfonyl)-4-chloro-2-[(2-furanylmethyl)amino] benzoate (15) (0.025 mole) in acetonitrile (30 mL) is added dropwise. After the addition is complete, the reaction is heated to reflux for 2 hours. The reaction is cooled, the volatiles removed by spin evaporation, and the residue partitioned between dichloromethane and 5% aqueous sodium bicarbonate. The organic layer is washed with water, and then with a saturated sodium chloride solution. The organic layer is dried over sodium sulfate, filtered and concentrated in vacuo to give crude product, which may be purified by column chromatography on silica gel with hexanes/ethyl acetate as eluent. The fractions that contain pure product may be combined and spin evaporated in vacuo to give a solid that may be recrystallized to give 2-[(5-(aminosulfonyl)-4-chloro-2-[(2-furanylmethyl)amino]benzoyloxymethyl)(1,1-dimethylethyl)amino]-1-(3-chlorophenyl)-1-propanone (720). See eg., U.S. Pat. No. 5,104,870 and Sandler, et al., Organic Functional Group Preparations, p. 324 (1968).

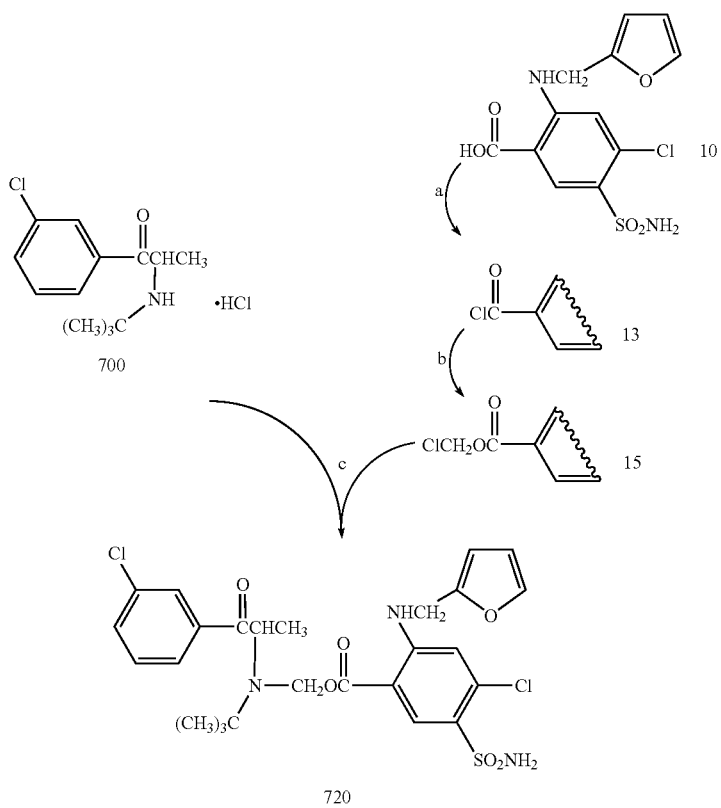

The following conjugate compounds may be prepared, for example, by the same general method:
(2S,3S)-4-[5-(aminosulfonyl)-4-chloro-2-[(2-furanylmethyl)amino]benzoyloxymethyl]-2-(3-chlorophenyl)-3,5,5-trimethyl-2-morpholinol; and
(2S,3S,5R)-4-[5-(aminosulfonyl)-4-chloro-2-[(2-furanylmethyl)amino]benzoyloxymethyl]-2-(3,5-difluorophenyl)-3,5-dimethyl-2-morpholinol.

Prophetic Example 8

Scheme G depicts a synthesis of a therapeutic amine-arylsulfonamide conjugate compound where the linker (W) is —C(O)R¹O—, where R¹ is —(CH₂)ₙC(O)O(CH₂)ₙ—; and where n is 2 and 3, respectively.

Preparation of 2-(1-(3,5-difluorobenzoyl)-(R,S)-ethylamino)-(R)-2-methylethyl 4-(3-(5-(aminosulfonyl)-4-chloro-2-[(2-furanylmethyl)amino]benzoyloxy)propoxy)(4-oxo)butanoate (820)

a Preparation of 3-(5-(aminosulfonyl)-4-chloro-2-[(2-furanylmethyl)amino]benzoyloxy)propanol (805)

A mixture of furosemide (5-(aminosulfonyl)-4-chloro-2-[(2-furanylmethyl)amino]benzoic acid), (10) (Aldrich) (0.060 mole), 3-bromo-1-propanol (Aldrich) (0.055 mole), DBN (1,5-diazabicyclo[4.3.0]non-5-ene, (Aldrich) (0.060 mole) and dry acetonitrile (100 mL) is stirred at ambient temperature for 10 hours. The reaction mixture is diluted with dichloromethane (200 mL) and extracted with sodium bicarbonate solution, washed with water, and then with a saturated sodium chloride solution. The organic layer is dried over sodium sulfate, filtered and concentrated in vacuo to give crude product, which may be purified by column chromatography on silica gel with hexanes/ethyl acetate as eluent. The fractions that contain pure product may be combined and spin evaporated in vacuo to give 3-(5-(aminosulfonyl)-4-chloro-2-[(2-furanylmethyl)amino]benzoyloxy)propanol (805). See eg., T. W. Greene and P. G. M. Wuts, Protective Groups in Organic Synthesis, p. 228 (1991).

b Preparation of 4-(3-(5-(aminosulfonyl)-4-chloro-2-[(2-furanylmethyl)amino]benzoyloxy)propoxy)(4-oxo)butanoic acid (810)

A mixture of 3-(5-(aminosulfonyl)-4-chloro-2-[(2-furanylmethyl)amino]benzoyloxy)propanol (805) (0.060 mole), succinic anhydride (Aldrich) (0.060 mole), DBN (1,5-diazabicyclo[4.3.0]non-5-ene,(Aldrich) (0.060 mole) and dry acetonitrile (50 mL) is stirred at ambient temperature for 10 hours. The reaction mixture is diluted with dichloromethane (200 mL) and extracted with 0.1 N hydrochloric acid solution, washed with water, and then with a saturated sodium chloride solution. The organic layer is dried over sodium sulfate, filtered and concentrated in vacuo to give crude product, which may be purified by column chromatography on silica gel with hexanes/ethyl acetate as eluent. The fractions that contain pure product may be combined and spin evaporated in vacuo to give to give 4-(3-(5-(aminosulfonyl)-4-chloro-2-[(2-furanylmethyl)amino]benzoyloxy)propoxy)(4-oxo)butanoic acid (810).

c Preparation 2-(1-(3,5-difluorobenzoyl)-(R,S)-ethylamino)-(R)-2-methylethyl 4-(3-(5-(aminosulfonyl)-

4-chloro-2-[(2-furanylmethyl)amino]benzoyloxy) propoxy)(4-oxo)butanoate (820)

The following conjugate compound may be prepared by the same general method:

2-(1-(3-chlorobenzoyl)-(R,S)-ethylamino)-2,2-dimethylethyl 4-(3-(5-(aminosulfonyl)-4-chloro-2-[(2-furanylmethyl)amino]benzoyloxy)propoxy)(4-oxo)butanoate.

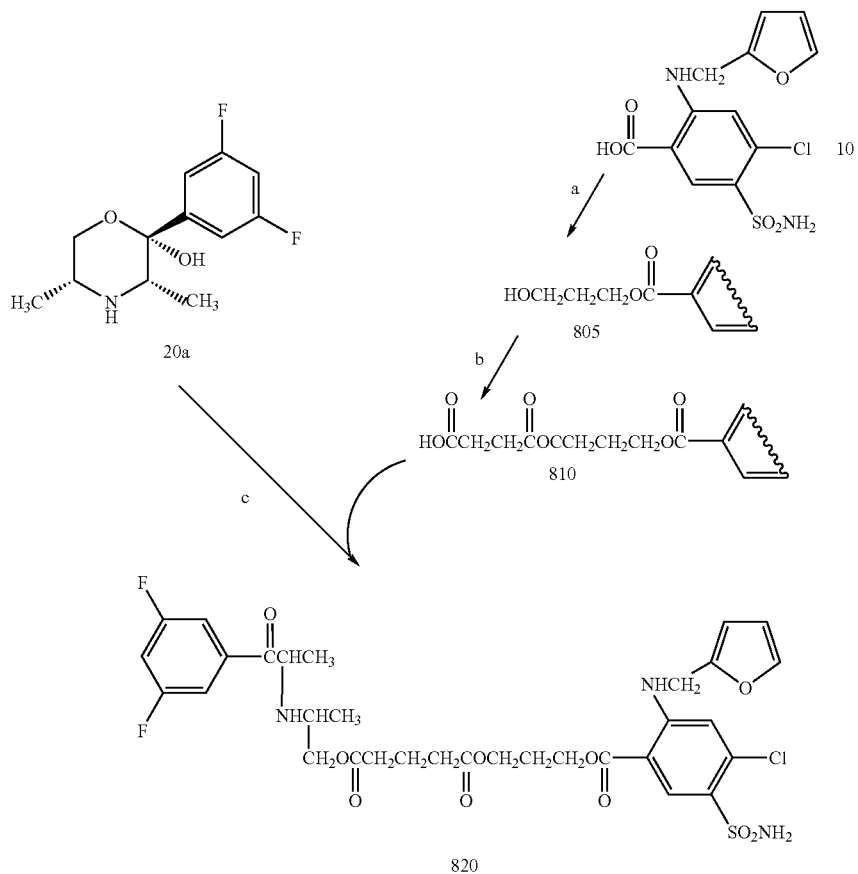

The free base of (2S,3S,5R)-2-(3,5-difluorophenyl)-3,5-dimethyl-2-morpholinol (20a) (0.023 mole) (U.S. Pat. No. 5,104,870) and benzene (30 mL) (or toluene) is added to a round-bottomed flask. 4-(3-(5-(aminosulfonyl)-4-chloro-2-[(2-furanylmethyl)amino]benzoyloxy)propoxy)(4-oxo)butanoic acid (810) (0.025 mole), benzene (30 mL), and p-toluenesulfonic acid (0.026 mole) catalyst is added to the flask. A Dean-Stark trap is filled with benzene, and the contents of the flask is refluxed with stirring for several hours or until no additional water is collected in the trap. The reaction is cooled, extracted with sodium bicarbonate solution, washed with water, and then with a saturated sodium chloride solution. The organic layer is dried over sodium sulfate, filtered and concentrated in vacuo to give crude product, which may be purified by column chromatography on silica gel with hexanes/ethyl acetate as eluent. The fractions that contain pure product may be combined and spin evaporated in vacuo to give a solid that may be recrystallized to give 2-(1-(3,5-difluorobenzoyl)-(R,S)-ethylamino)-(R)-2-methylethyl 4-(3-(5-(aminosulfonyl)-4-chloro-2-[(2-furanylmethyl) amino]benzoyloxy)propoxy)(4-oxo)butanoate (820). See eg. Sandler, et al., Organic Functional Group Preparations, p. 249 (1968).

Prophetic Example 9

Scheme H depicts a synthesis of another therapeutic amine-arylsulfonamide conjugate compound as in Example 8, where the linker (W) is —CH$_2$OC(O)R$^1$O—, R$^1$ is —(CH$_2$)$_n$C(O)O(CH$_2$)$_n$—; where n is 2 and 3, respectively.

Preparation of 2-[(4-(3-(5-(aminosulfonyl)-4-chloro-2-[(2-furanylmethyl)amino]benzoyloxy)propoxy)(4-oxo)butanoyloxymethyl)(1,1-dimethylethyl)amino]-1-(3-chlorophenyl)-1-propanone (920)

a Preparation of 4-(3-(5-(aminosulfonyl)-4-chloro-2-[(2-furanylmethyl)amino]benzoyloxy)propoxy)(4-oxo)butanoyl chloride (813)

A solution of oxalyl chloride (0.040 mole) in dichloromethane (20 mL) is added dropwise to an ice bath cooled solution of 4-(3-(5-(aminosulfonyl)-4-chloro-2-[(2-furanylmethyl)amino]benzoyloxy)propoxy)(4-oxo)butanoic acid (810) (0.040 mole) in dichloromethane (50 mL). The reaction is stirred at ambient temperature for 5 hours. The reaction solution is washed with 5% aqueous sodium bicarbonate, with water, and then with a saturated sodium chloride solution. The organic layer is dried over sodium sulfate, filtered and concentrated in vacuo to provide 4-(3-(5-(aminosulfonyl)-4-chloro-2-[(2-furanylmethyl)amino]benzoyloxy)propoxy)(4-oxo)butanoyl chloride (813). See eg., D. L. Musso, et. al., *J. Med. Chem.*, (2003) 46: 409.

b Preparation of chloromethyl 4-(3-(5-(aminosulfonyl)-4-chloro-2-[(2-furanylmethyl)amino]benzoyloxy)propoxy)(4-oxo)butanoate (815)

A mixture of 4-(3-(5-(aminosulfonyl)-4-chloro-2-[(2-furanylmethyl)amino]benzoyloxy)propoxy)(4-oxo)butanoyl chloride (813) (0.040 mole) and paraformaldehyde (0.040 mole) is heated in a sealed vessel at 90° C. for 3 hours. The reaction is cooled, and the solids are dissolved in dichloromethane. The solution is washed with 5% aqueous sodium bicarbonate, with water, and then with a saturated sodium chloride solution. The organic layer is dried over sodium sulfate, filtered and concentrated in vacuo to give crude product, which may be purified by column chromatography on silica gel with hexanes/ethyl acetate as eluent. The fractions that contain pure product may be combined and spin evaporated in vacuo to give chloromethyl 4-(3-(5-(aminosulfonyl)-4-chloro-2-[(2-furanylmethyl)amino]benzoyloxy)propoxy)(4-oxo)butanoate (815). See eg., Bodor, et al., *J. Med. Chem.*, 23, 469 (1980), and Ulich, et al., *J. Am. Chem. Soc.*, (1921) 43: 660.

c Preparation of 2-[(4-(3-(5-(aminosulfonyl)-4-chloro-2-[(2-furanylmethyl)amino]benzoyloxy)propoxy)(4-oxo)butanoyloxymethyl)(1,1-dimethylethyl)amino]-1-(3-chlorophenyl)-1-propanone (920)

A solution of bupropion[1-(3-chlorophenyl)-2-[(1,1-dimethylethyl)amino]-1-propanone hydrochloride (700), (U.S. Pat. No. 3,819,706 and U.S. Pat. No. 3,885,046) (0.025 mole), triethylamine (0.055 mole) and acetonitrile (30 mL) is stirred with cooling on an ice bath. A solution of chloromethyl 4-(3-(5-(aminosulfonyl)-4-chloro-2-[(2-furanylmethyl)amino]benzoyloxy)propoxy)(4-oxo)butanoate (0.025 mole) in acetonitrile (30 mL) is added dropwise. After the addition is complete, the reaction is heated to reflux for 2 hours. The reaction is cooled, the volatiles removed by spin evaporation, and the residue partitioned between dichloromethane and 5% aqueous sodium bicarbonate. The organic layer is washed with water, and then with a saturated sodium chloride solution. The organic layer is dried over sodium sulfate, filtered and concentrated in vacuo to give crude product, which may be purified by column chromatography on silica gel with hexanes/ethyl acetate as eluent. The fractions that contain pure product may be combined and spin evaporated in vacuo to give a solid that may be recrystallized to give 2-[(4-(3-(5-(aminosulfonyl)-4-chloro-2-[(2-furanylmethyl)amino]benzoyloxy)propoxy)(4-oxo)butanoyloxymethyl)(1,1-dimethylethyl)amino]-1-(3-chlorophenyl)-1-propanone (920). See eg., U.S. Pat. No. 5,104,870 and Sandler, et al., Organic Functional Group Preparations, p. 324 (1968).

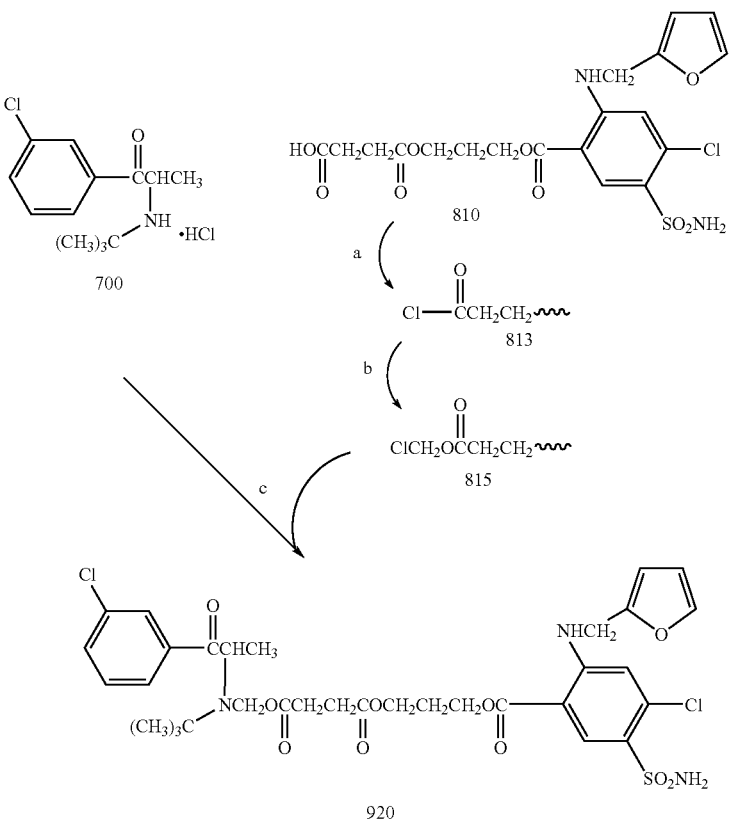

Prophetic Example 10

Scheme I depicts a synthesis of a therapeutic amine-arylsulfonamide conjugate compound having carbamate functionality, wherein the linker (W) is —C(O)OCHRO—, where R is H; and the therapeutic amine radical is coupled to the linker by a nitrogen atom.

Preparation of 2-[(5-(aminosulfonyl)-4-chloro-2-[(2-furanylmethyl)amino]benzoyloxymethoxycarbonyl) (1,1-dimethylethyl)amino]-1-(3-chlorophenyl)-1-propanone (1020)

a Preparation of O-(5-(aminosulfonyl)-4-chloro-2-[(2-furanylmethyl)amino]benzoyloxymethyl) S-ethyl carbonothioate (1005)

Furosemide (5-(aminosulfonyl)-4-chloro-2-[(2-furanylmethyl)amino]benzoic acid), (10) (Aldrich) (0.050 mole) is added to a stirred solution of sodium bicarbonate (0.100 mole) and tetrabutylammonium hydrogen sulfate (0.050 mole) in water (100 mL) at ambient temperature. After 10 minutes 1,2-dichloroethane (100 mL) is added and then after 30 minutes O-iodomethyl S-ethyl carbonothioate (0.050 mole) in 1,2-dichloroethane (25 mL) is added over 15 minutes. The mixture is stirred for 1 hour at ambient temperature. The organic layer is separated, washed with water (50 mL), dried (magnesium sulfate), and the solvent is evaporated. The residue is stirred with diethyl ether (100 mL), insoluble material is filtered off and washed with diethyl ether. The combined ether phases is evaporated, and the residue may be crystallized to give O-(5-(aminosulfonyl)-4-chloro-2-[(2-furanylmethyl)amino]benzoyloxymethyl) S-ethyl carbonothioate (1005). See eg., Folkmann, et al., *Synthesis*, 1159 (1990), Method D.

b Preparation of 5-(aminosulfonyl)-4-chloro-2-[(2-furanylmethyl)amino]benzoyloxymethyl carbonochloridate (1010)

Freshly distilled sulfuryl chloride (0.050 mole) in dichloromethane (25 mL) is added to O-(5-(aminosulfonyl)-4-chloro-2-[(2-furanylmethyl)amino]benzoyloxymethyl) S-ethyl carbonothioate (1005) (0.050 mole) in dichloromethane (25 mL) at 0-5° C. with stirring during 15 minutes followed by stirring at ambient temperature for 45 minutes. The volatiles are removed by evaporation at ambient temperature and then at 20 millibar for 16 hours. The crude product is dissolved in ethyl acetate and applied to a column of silica gel. The column may be eluted with hexanes/ethyl acetate, and the fractions that contain pure product may be combined and spin evaporated in vacuo to give 5-(aminosulfonyl)-4-chloro-2-[(2-furanylmethyl)amino]benzoyloxymethyl carbonochloridate (1010). See eg., Folkmann, et al., Synthesis, 1159 (1990), Method G.

c Preparation of 2-[(5-(aminosulfonyl)-4-chloro-2-[(2-furanylmethyl)amino]benzoyloxymethoxycarbonyl)(1,1-dimethylethyl)amino]-1-(3-chlorophenyl)-1-propanone (1020)

A solution of bupropion[1-(3-chlorophenyl)-2-[(1,1-dimethylethyl)amino]-1-propanone hydrochloride (700), (U.S. Pat. Nos. 3,819,706 and 3,885,046) (0.025 mole), triethylamine (0.055 mole) and acetonitrile (30 mL) is stirred with cooling on an ice bath. A solution of 5-(aminosulfonyl)-4-chloro-2-[(2-furanylmethyl)amino]benzoyloxymethyl carbonochloridate (1010) (0.025 mole) in acetonitrile (30 mL) is added dropwise. After the addition is complete, the reaction is heated to reflux for 2 hours. The reaction is cooled, the volatiles removed by spin evaporation, and the residue partitioned between dichloromethane and 5% aqueous sodium bicarbonate. The organic layer is washed with water, and then with a saturated sodium chloride solution. The organic layer is dried over sodium sulfate, filtered and concentrated in vacuo to give crude product, which may be purified by column chromatography on silica gel with hexanes/ethyl acetate as eluent. The fractions that contain pure product may be combined and spin evaporated in vacuo to give a solid that may be recrystallized to give 2-[(5-(aminosulfonyl)-4-chloro-2-[(2-furanylmethyl)amino]benzoyloxymethoxycarbonyl)(1,1-dimethylethyl)amino]-1-(3-chlorophenyl)-1-propanone (1020). See eg., U.S. Pat. No. 5,104,870 and Sandler, et al., Organic Functional Group Preparations, p. 324 (1968).

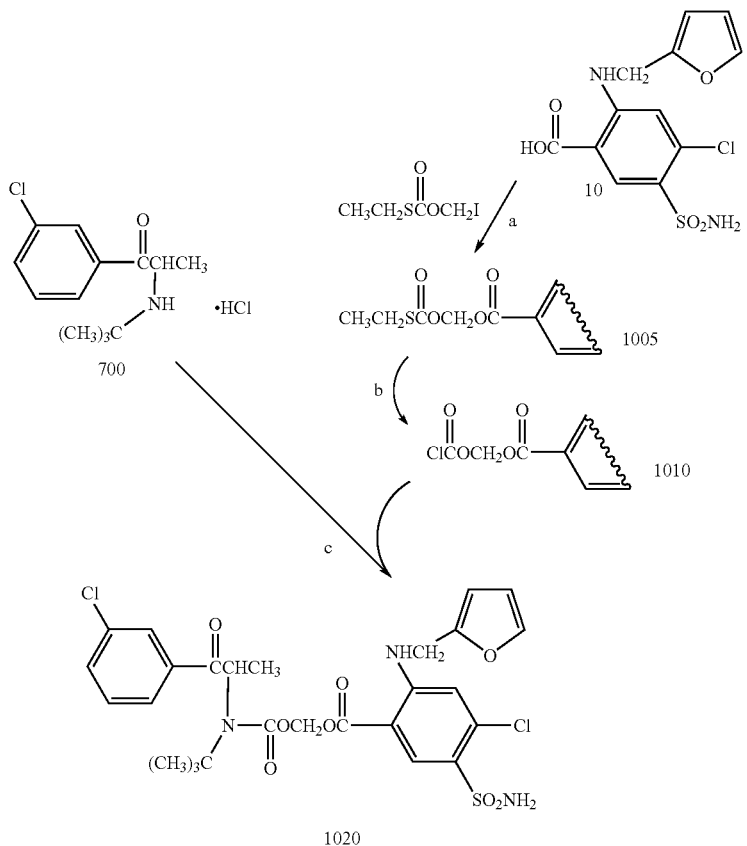

The following conjugate compounds may be prepared, for example, by the same general method:
(2S,3S)-4-[5-(aminosulfonyl)-4-chloro-2-[(2-furanylmethyl)amino]benzoyloxymethoxycarbonyl]-2-(3-chlorophenyl)-3,5,5-trimethyl-2-morpholinol; and
(2S,3S,5R)-4-[5-(aminosulfonyl)-4-chloro-2-[(2-furanylmethyl)amino]benzoyloxymethoxycarbonyl]-2-(3,5-difluorophenyl)-3,5-dimethyl-2-morpholinol.

Prophetic Example 11

Preparation of (5-(aminosulfonyl)-4-chloro-2-[(2-furanylmethyl)amino]benzoyloxymethyl)(10,11-dihydro-5H-dibenz[b,f]azepine-5-propyl)dimethylammonium chloride (1120)

Scheme J depicts a synthesis of a therapeutic amine-arylsulfonamide conjugate compound wherein the linker (W) is —CH$_2$O—, and where the conjugate compound formed would be a quaternary ammonium salt.

a Preparation of 5-(aminosulfonyl)-4-chloro-2-[(2-furanylmethyl)amino]benzoyl chloride (13)

A solution of oxalyl chloride (0.040 mole) in dichloromethane (20 mL) is added dropwise to an ice bath cooled solution of furosemide (5-(aminosulfonyl)-4-chloro-2-[(2-furanylmethyl)amino]benzoic acid), (10) (Aldrich) (0.040 mole) in dichloromethane (50 mL). The reaction is stirred at ambient temperature for 5 hours. The reaction solution is washed with 5% aqueous sodium bicarbonate, with water, and then with a saturated sodium chloride solution. The organic layer is dried over sodium sulfate, filtered and concentrated in vacuo to give 5-(aminosulfonyl)-4-chloro-2-[(2-furanylmethyl)amino]benzoyl chloride (13). See D. L. Musso, et. al., J. Med. Chem., (2003) 46: 409.

b Preparation of chloromethyl 5-(aminosulfonyl)-4-chloro-2-[(2-furanylmethyl)amino]benzoate (15)

A mixture of 5-(aminosulfonyl)-4-chloro-2-[(2-furanylmethyl)amino]benzoyl chloride (13) (0.040 mole) and paraformaldehyde (0.040 mole) is heated in a sealed vessel at 90° C. for 3 hours. The reaction is cooled, and the solids is dissolved in dichloromethane. The solution is washed with 5% aqueous sodium bicarbonate, with water, and then with a saturated sodium chloride solution. The organic layer is dried over sodium sulfate, filtered and concentrated in vacuo to give crude product, which may be purified by column chromatography on silica gel with hexanes/ethyl acetate as eluent. The fractions that contain pure product may be combined and spin evaporated in vacuo to give chloromethyl 5-(aminosulfonyl)-4-chloro-2-[(2-furanylmethyl)amino]benzoate (15). See Bodor, et al., J. Med. Chem., 23, 469 (1980), and Ulich, et al., J. Am. Chem. Soc., (1921) 43: 660.

c Preparation of (5-(aminosulfonyl)-4-chloro-2-[(2-furanylmethyl)amino]benzoyloxymethyl)(10,11-dihydro-5H-dibenz[b,f]azepine-5-propyl)dimethylammonium chloride (1120)

A mixture of imipramine(10,11-dihydro-N,N-dimethyl-5H-dibenz[b,f]azepine-5-propanamine), (1100)(Aldrich)

(0.023 mole) and acetonitrile (30 mL) is stirred with cooling on an ice bath. A solution of chloromethyl 5-(aminosulfonyl)-4-chloro-2-[(2-furanylmethyl)amino]benzoate (15) (0.023 mole) in acetonitrile (30 mL) is added dropwise. After the addition is complete, the reaction is heated to reflux for 2 hours. The reaction is cooled, anhydrous ether (120 mL) is added, and the mixture is stirred for 10 hours. The solid is collected by suction filtration and washed with anhydrous ether. The solid is dried in vacuo to give (5-(aminosulfonyl)-4-chloro-2-[(2-furanylmethyl)amino]benzoyloxymethyl) (10,11-dihydro-5H-dibenz[b,f]azepine-5-propyl)dimethylammonium chloride (1120). U.S. Pat. No. 5,104,870 and Bodor, et al., *J. Med. Chem.*, (1980) 23: 469.

semide (10) (5-(aminosulfonyl)-4-chloro-2-[(2-furanylmethyl)amino]benzoic acid, Aldrich) (0.025 mole), benzene (30 mL), and p-toluenesulfonic acid (0.001 mole) catalyst are added to the flask. A Dean-Stark trap is filled with benzene, and the contents of the flask are refluxed with stirring for several hours or until no additional water is collected in the trap. The reaction is cooled, extracted with sodium bicarbonate solution, washed with water, and then with a saturated sodium chloride solution. The organic layer may be dried over sodium sulfate, filtered and concentrated in vacuo to give 2,2,2-trichloroethyl 5-(aminosulfonyl)-4-chloro-2-[(2-furanylmethyl)amino]benzoate. See Sandler et al., *Organic Functional Group Preparations*, (1968) p. 249.

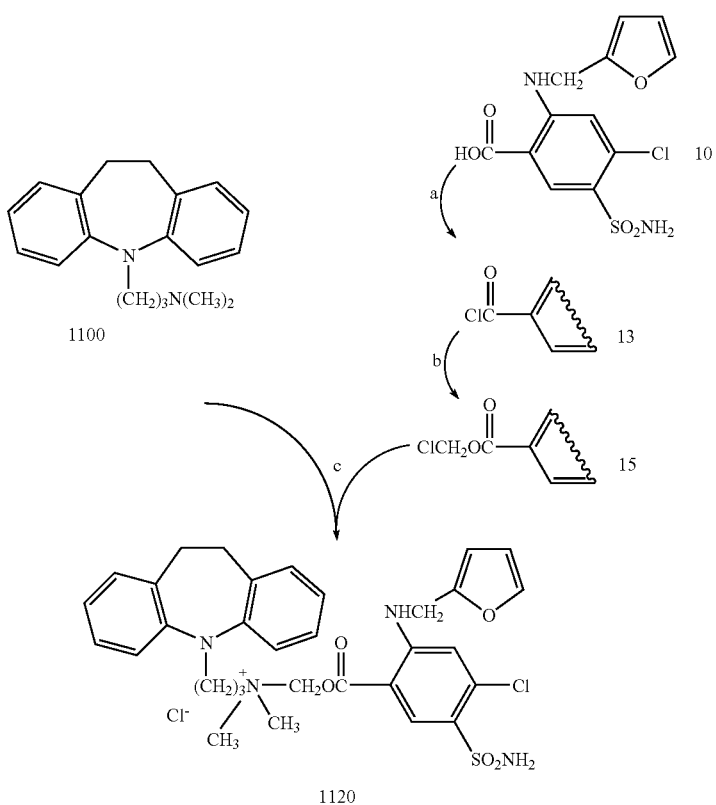

Prophetic Example 12

Scheme K depicts a synthesis of a therapeutic amine-arylsulfonamide conjugate compound where the therapeutic amine is linked to the sulfonamide group of furosemide via a linker (W') that is —CHROC(O)R$^1$C(O)OCHR—; where R$^1$ is —(CH$_2$)$_n$—, where n is 4; and R is H.

Preparation of 2-[(6-(5-carboxy-2-chloro-4-[(2-furanylmethyl)amino]phenylsulfonamidomethoxy) (6-oxo)hexanoyloxymethyl)(1,1-dimethylethyl) amino]-1-(3-chlorophenyl)-1-propanone (1220)

a Preparation of 2,2,2-trichloroethyl 5-(aminosulfonyl)-4-chloro-2-[(2-furanylmethyl)amino]benzoate (11)

Benzene (30 mL) (or toluene) and 2,2,2-trichloroethanol (0.024 mole) are added to a round-bottomed flask. Furob Preparation of 6-methoxy-6-oxohexanoyl chloride A solution of oxalyl chloride (0.040 mole) in dichloromethane (20 mL) is added dropwise to an ice bath cooled solution of adipic acid monomethyl ester (Aldrich) (0.040 mole) in dichloromethane (50 mL). The reaction is stirred at ambient temperature for 5 hours. The reaction solution is washed with 5% aqueous sodium bicarbonate, with water, and then with a saturated sodium chloride solution. The organic layer may be dried over sodium sulfate, filtered and concentrated in vacuo to give 6-methoxy-6-oxohexanoyl chloride. See Musso, et. al., *J. Med. Chem.*, (2003) 46:409.

c Preparation of chloromethyl 6-methoxy-6-oxohexanoate

A mixture of 6-methoxy-6-oxohexanoyl chloride (0.040 mole) and paraformaldehyde (0.040 mole) are heated in a sealed vessel at 90 degrees for 3 hours. The reaction is cooled, and the solids are dissolved in dichloromethane. The solution is washed with 5% aqueous sodium bicarbonate, with water, and then with a saturated sodium chloride solution. The organic layer is dried over sodium sulfate, filtered and concentrated in vacuo to give crude product, which is purified by column chromatography on silica gel with hexanes/ethyl acetate as eluent. The fractions that contain pure product may be combined and spin evaporated in vacuo to give chloromethyl 6-methoxy-6-oxohexanoate. See Bodor et al., *J. Med. Chem.*, (1980) 23: 469; Ulich et al., *J. Am. Chem. Soc.*, (1921) 43: 660.

d Preparation of methyl 6-(2-chloro-4-[(2-furanylmethyl)amino]-5-(2,2,2-trichloroethoxycarbonyl)phenylsulfonamidomethoxy)(6-oxo)hexanoate A mixture of 2,2,2-trichloroethyl 5-(aminosulfonyl)-4-chloro-2-[(2-furanylmethyl)amino]benzoate (0.060 mole), chloromethyl 6-methoxy-6-oxohexanoate (0.060 mole), DBN (1,5-diazabicyclo[4.3.0]non-5-ene, Aldrich) (0.060 mole) and dry acetonitrile (100 mL) is stirred at ambient temperature for 10 hours. The reaction mixture is diluted with dichloromethane (200 mL) and extracted with sodium bicarbonate solution, washed with water, and then with a saturated sodium chloride solution. The organic layer is dried over sodium sulfate, filtered and concentrated in vacuo to give crude product, which is purified by column chromatography on silica gel with hexanes/ethyl acetate as eluent. The fractions that contain pure product may be combined and spin evaporated in vacuo to give methyl 6-(2-chloro-4-[(2-furanylmethyl)amino]-5-(2,2,2-trichloroethoxycarbonyl)phenylsulfonamidomethoxy)(6-oxo)hexanoate.

e Preparation of 6-(2-chloro-4-[(2-furanylmethyl)amino]-5-(2,2,2-trichloroethoxycarbonyl)phenylsulfonamidomethoxy)(6-oxo)hexanoic acid A mixture of methyl 6-(2-chloro-4-[(2-furanylmethyl)amino]-5-(2,2,2-trichloroethoxycarbonyl)phenylsulfonamidomethoxy)(6-oxo)hexanoate (0.060 mole), sodium cyanide (0.060 mole) and hexamethylphosphoramide (Aldrich) (100 mL) is stirred at 75° C. for 24 hours. The volatiles are removed by spin evaporation in vacuo. The residue is dissolved in cold water, and the solution is washed with diethyl ether. The aqueous solution is cooled in an ice bath and acidified by dropwise addition of 1.0 N hydrochloric acid solution (60 mL). The resulting solid may be collected and recrystallized to give 6-(2-chloro-4-[(2-furanylmethyl)amino]-5-(2,2,2-trichloroethoxycarbonyl)phenylsulfonamidomethoxy)(6-oxo)hexanoic acid. See Greene et al., Protective Groups in Organic Synthesis, Second Edition, (1991) p. 232.

f Preparation of chloromethyl 6-(2-chloro-4-[(2-furanylmethyl)amino]-5-(2,2,2-trichloroethoxycarbonyl) phenylsulfonamidomethoxy)(6-oxo)hexanoate The 6-(2-chloro-4-[(2-furanylmethyl)amino]-5-(2,2,2-trichloroethoxycarbonyl)phenylsulfonamidomethoxy)(6-oxo)hexanoic acid (0.060 mole) is dispersed with stirring in a methanol-water mixture (100 mL), and an aqueous solution of cesium carbonate (2 molar) is added dropwise until the solution pH is 6.6. The volatiles are removed by spin evaporation in vacuo. The resulting cesium salt is dried by addition of toluene and removal of the volatiles under reduced pressure. This is repeated several times. The dry cesium salt is dissolved in dimethylformamide (100 mL), and bromochloromethane (Aldrich) (0.060 mole) is slowly added to the solution. The reaction is stirred at ambient temperature in the dark for 12 hours. The mixture is filtered to remove cesium bromide, and the volatiles are removed by spin evaporation in vacuo. The reaction mixture is diluted with dichloromethane (200 mL) and extracted with sodium bicarbonate solution, washed with water, and then with a saturated sodium chloride solution. The organic layer may be dried over sodium sulfate, filtered and concentrated in vacuo to give crude product, which may be purified by column chromatography on silica gel with hexanes/ethyl acetate as eluent. The fractions that contain pure product may be combined and spin evaporated in vacuo to give chloromethyl 6-(2-chloro-4-[(2-furanylmethyl)amino]-5-(2,2,2-trichloroethoxycarbonyl)phenylsulfonamidomethoxy)(6-oxo)hexanoate.

g Preparation of 2-[(6-(2-chloro-4-[(2-furanylmethyl)amino]-5-(2,2,2-trichloroethoxycarbonyl)phenylsulfonamidomethoxy)(6-oxo)hexanoyloxymethyl)(1,1-dimethylethyl)amino]-1-(3-chlorophenyl)-1-propanone A solution of bupropion[1-(3-chlorophenyl)-2-[(1,1-dimethylethyl)amino]-1-propanone hydrochloride, (700) (U.S. Pat. No. 3,819,706; U.S. Pat. No. 3,885,046) (0.025 mole), triethylamine (0.055 mole) and acetonitrile (30 mL) are stirred with cooling on an ice bath. A solution of chloromethyl 6-(2-chloro-4-[(2-furanylmethyl)amino]-5-(2,2,2-trichloroethoxycarbonyl)phenylsulfonamidomethoxy)(6-oxo)hexanoate (0.025 mole) in acetonitrile (30 mL) is added dropwise. After the addition is complete, the reaction is heated to reflux for 2 hours. The reaction is cooled, the volatiles are removed by spin evaporation, and the residue is partitioned between dichloromethane and 5% aqueous sodium bicarbonate. The organic layer is washed with water, and then with a saturated sodium chloride solution. The organic layer may be dried over sodium sulfate, filtered and concentrated in vacuo to give crude product, which may be purified by column chromatography on silica gel with hexanes/ethyl acetate as eluent. The fractions that contain pure product may be combined and spin evaporated in vacuo to give a solid that is recrystallized to give 2-[(6-(2-chloro-4-[(2-furanylmethyl)amino]-5-(2,2,2-trichloroethoxycarbonyl)phenylsulfonamidomethoxy)(6-oxo)hexanoyloxymethyl)(1,1-dimethylethyl)amino]-1-(3-chlorophenyl)-1-propanone. See U.S. Pat. No. 5,104,870; Sandler et al., Organic Functional Group Preparations, (1968) p. 324.

h Preparation of 2-[(6-(5-carboxy-2-chloro-4-[(2-furanylmethyl)amino]phenylsulfonamidomethoxy) (6-oxo)hexanoyloxymethyl)(1,1-dimethylethyl) amino]-1-(3-chlorophenyl)-1-propanone (1220)

A solution of 2-[(6-(2-chloro-4-[(2-furanylmethyl)amino]-5-(2,2,2-trichloroethoxycarbonyl)phenylsulfonamidomethoxy)(6-oxo)hexanoyloxymethyl)(1,1-dimethylethyl)amino]-1-(3-chlorophenyl)-1-propanone (0.060 mole) in acetic acid (100 mL) is cooled in an ice water bath. Zinc dust (0.12 mole) is added in several portions with stirring, and the reaction is stirred for 2.5 hours at 0° C. The mixture is filtered to remove zinc salts, and the volatiles are removed by spin evaporation in vacuo. The residue is dissolved in cold water, and the solution is washed with diethyl ether. The aqueous solution is cooled in an ice bath and acidified by dropwise addition of 1.0 N hydrochloric acid solution (60 mL). The resulting solid may be collected and recrystallized to give 2-[(6-(5-carboxy-2-chloro-4-[(2-furanylmethyl)amino]phenylsulfonamidomethoxy)(6-oxo)hexanoyloxymethyl)(1,1-dimethylethyl)amino]-1-(3-chlorophenyl)-1-propanone (1220). See Greene et al., Protective Groups in Organic Synthesis, Second Edition, (1991) p. 240.
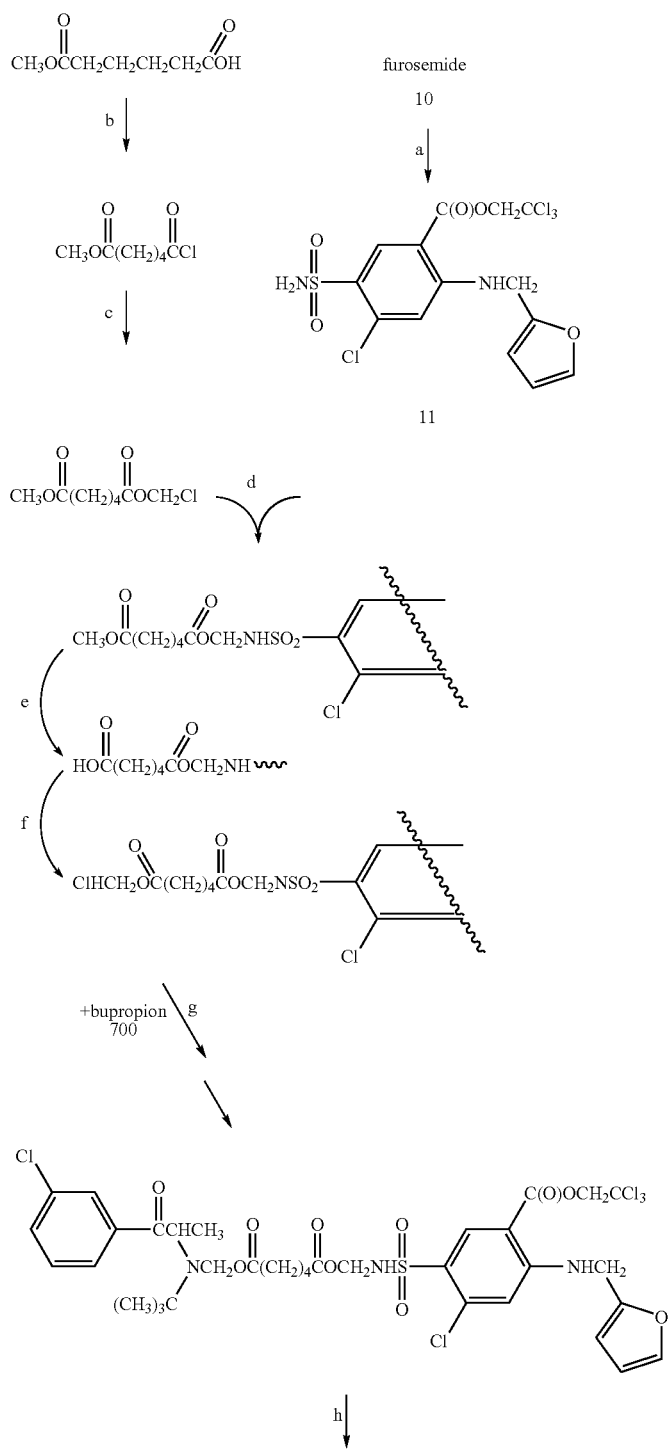

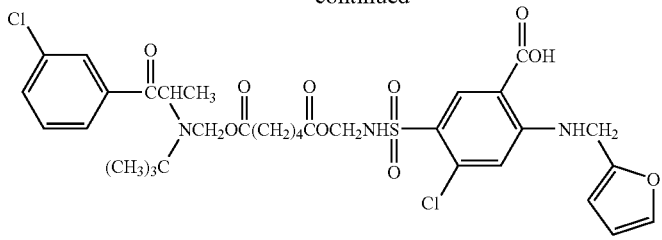

1220

Scheme L represents a therapeutic amine radical coupled to a linker by a nitrogen atom of the arylsulfonamide via a linker (W') that is —C(O)R¹C(O)OCHROC(O)—; where R¹ is —(CH$_2$)$_n$—, where n is 4, and R is H. Thus, {[(ethylthio) carbonyl]oxy}methyl methyl adipate (1313), prepared from 6-methoxyl-6-oxohexanoic acid (1307) and O-iodomethyl S-ethyl carbonothioate (see Example 10 a), is converted to [(chlorocarbonyl)oxy]methyl methyl adipate (1317), in a manner analogus to that for compound (1010) in Scheme I, followed by subsequent reaction with 2,2,2-trichloroethanol ester of furosemide (11). The resulting product (1300) is hydrolyzed, condensed with (21), and oxidized to provide 2-(1-(3,5-difluorobenzoyl)-(R,S)-ethylamino)-(R)-2-methylethyl 6-(5-carboxy-2-chloro-4-[(2-furanylmethyl)amino]phenylsulfonamidocarbonyloxymethoxy)(6-oxo)hexanoate (1320).

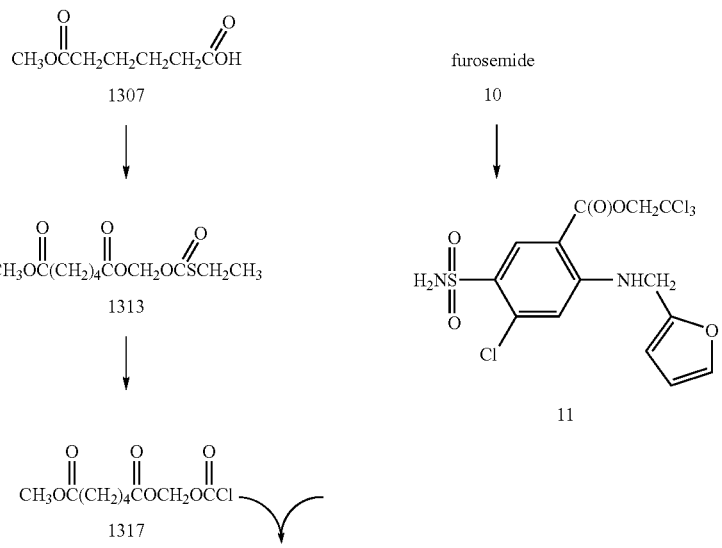

-continued

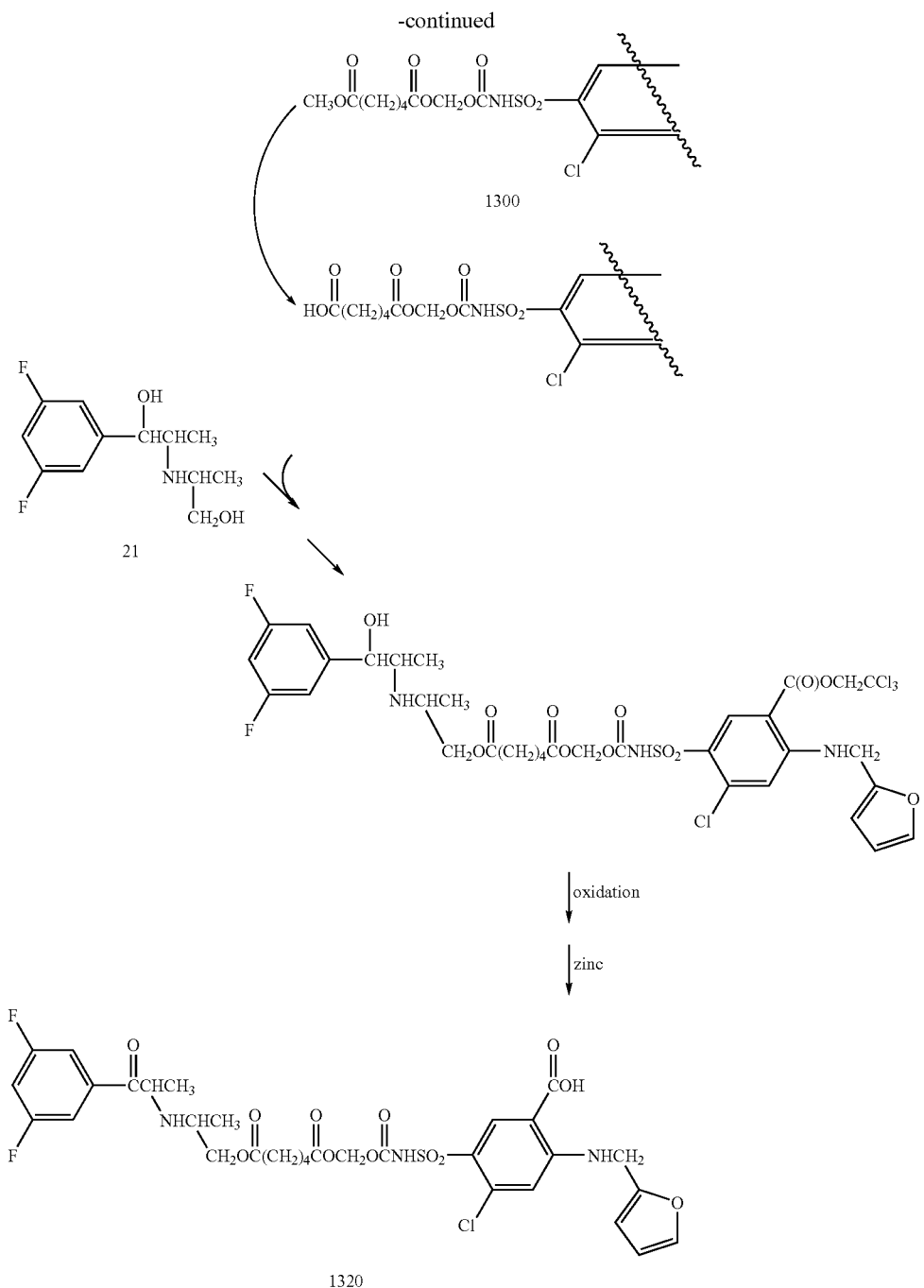

Experimental Example 13

General: Solvents and reagents were purchased from Sigma-Aldrich (St. Louis, Mo.) and were used as received. Nuclear Magnetic Resonance (NMR) data was acquired on a Varian 400 and/or Varian 500 mHz spectrometer. LC/MS data was acquired using a Thermo-Finnegin Surveyor HPLC equipped with a Phenomenex C18 column connected to an AQA mass spectrometer.

Scheme M is a synthesis of a therapeutic amine-arylsulfonamide conjugate compound wherein the linker (W) is —C(O)OCHRO—; where R is hydrogen.

Preparation of (2S,3S,5R)-4-[5-(aminosulfonyl)-4-chloro-2-[(2-furanylmethyl)amino]benzoyloxymethoxycarbonyl]-2-(3,5-difluorophenyl)-3,5-dimethyl-2-morpholinol (1420)

Preparation of (2S,3S,5R)-2-(3,5-difluorophenyl)-2-hydroxy-3,5-dimethylmorpholine-4-carboxylic acid chloromethyl ester (1410)

To a stirring solution of (2S,3S,5R)-2-(3,5-difluorophenyl)-2-hydroxy-3,5-dimethylmorpholine (2.5 g, 10.28 mmol) in dichloromethane (50 mL) at room temperature under nitrogen, was added potassium carbonate (1.42 gm, 10.28 mmol). The mixture was cooled to 5° C. with a wet ice bath, and chloromethyl chloroformate (0.915 mL, 10.28 mmol) in dichloromethane (10 mL) was added dropwise. The mixture was allowed to warm to room temperature slowly and stirred over night. TLC analysis (1:1 heptane:ethyl acetate) indicated that the starting material was consumed and a new less polar spot had formed. Water was added to the mixture and then it was extracted with dichloromethane (3×). The organic layers were combined and dried over magnesium sulfate, filtered and the solvent was removed to afford a crude weight of 2.8 grams of (2S,3S,5R)-2-(3,5-difluorophenyl)-2-hydroxy-3,5-dimethylmorpholine-4-carboxylic acid chloromethyl ester (1410) as an opaque tar.

$^1$H NMR (400 MHz, CDCl$_3$) δ 1.27-1.29 (d, 3H), 1.47-1.49 (d, 3H), 3.79-3.90 (m, 2H), 4.10-4.16 (m, 1H), 4.55-4.60 (m, 1H), 5.64-5.65 (d, 1H), 5.77-5.78 (d, 1H), 6.73-6.77 (m, 1H), 7.02-7.04 (d, 2H). Compound (1410) was used without purification.

Preparation of the cesium salt of furosemide (cesium 5-(aminosulfonyl)-4-chloro-2-[(2-furanylmethyl)amino]benzoate) (10c)

Furosemide (10) (5-(aminosulfonyl)-4-chloro-2-[(2-furanylmethyl)amino]benzoic acid, Aldrich) (4.0 g, 12.1 mmol) was added to dioxane (100 mL), and water (50 mL) was added with stirring to give a solution. Cesium carbonate (1.97 g, 6.0 mmol) was added, and the clear solution was stirred for 1 hour. The solvent was removed by spin evaporation, and the solid was dried overnight on a vacuum pump to afford 5.31 g of cesium 5-(aminosulfonyl)-4-chloro-2-[(2-furanylmethyl)amino]benzoate as a white solid.

SCHEME M

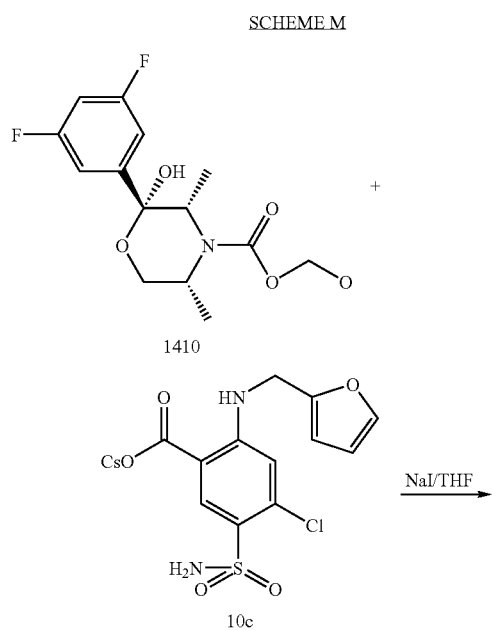

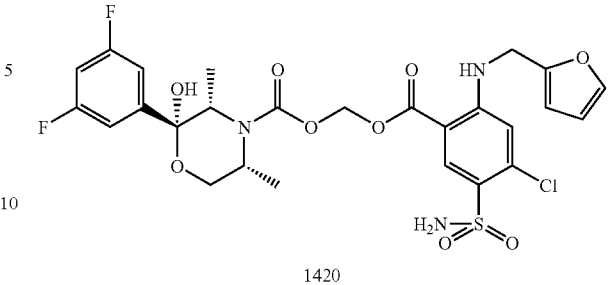

Preparation of (2S,3S,5R)-4-[5-(aminosulfonyl)-4-chloro-2-[(2-furanylmethyl)amino]benzoyloxymethoxycarbonyl]-2-(3,5-difluorophenyl)-3,5-dimethyl-2-morpholinol (1420)

To a stirring solution of (2S,3S,5R)-2-(3,5-difluorophenyl)-2-hydroxy-3,5-dimethylmorpholine-4-carboxylic acid chloromethyl ester (1410) (2.24 g, 6.67 mmol) in 150 mL of anhydrous tetrahydrofuran was added the furosemide cesium salt (10c) (3.09 gm, 6.67 mmol) and sodium iodide (1.10 gm, 7.34 mmol). The mixture was heated to ~60° C. and monitored by TLC (1:1 heptane:ethyl acetate). After heating for 6 hours, TLC analysis indicated a slowing down of product formation with starting materials remaining. The reaction was halted so as not to allow by-product formation. The solvent was removed from the crude yellow mixture, and it was dried onto silica gel. This crude material was purified on an Optix Companion Automated Chromatography system using an 80 gm silica cartridge and eluting with ethyl acetate/heptane (0 to 70% over 50 minutes). This material was dried on a vacuum pump for 24 hours and afforded 0.560 g of (2S,3S,5R)-4-[5-(aminosulfonyl)-4-chloro-2-[(2-furanylmethyl)amino]benzoyloxymethoxycarbonyl]-2-(3,5-difluorophenyl)-3,5-dimethyl-2-morpholinol (1420) as a light yellow foamy solid. Melting point range was 105° C. to 110° C. Elemental analysis calculated for [C$_{26}$H$_{26}$N$_3$ 0.3 EtOAc]: C, 49.76; H, 4.36; N, 6.4. found C, 50.08; H, 4.65; N, 6.23. $^1$H NMR (400 MHz, CDCl$_3$) δ 0.86-0.89 (t, 3H), 1.34 (m, 3H), 3.60-3.67 (m, 1H), 4.23 (m, 1H), 4.33 (m, 1H), 4.45-4.46 (d, 2H), 4.47 (s, 1H), 5.07-5.11 (d, 2H), 6.00-6.05 (dd, 2H), 6.28 (s, 1H), 6.35 (s, 1H), 6.75-6.79 (t, 1H), 6.89 (m, 1H), 7.12-7.14 (br. d, 2H), 7.37-7.39 (d, 1H), 8.53 (br. d., 1H), 8.63 (s, 1H).

The following conjugate compounds may be prepared, for example, by the same general method as described above in Example 13 and depicted in Scheme M:

(2S,3S,5R)-4-[2-(5-(aminosulfonyl)-4-chloro-2-[(2-furanylmethyl)amino]benzoyloxy)ethanoyloxymethoxycarbonyl]-2-(3,5-difluorophenyl)-3,5-dimethyl-2-morpholinol;

(2S,3S,5R)-4-[2-(5-(aminosulfonyl)-4-chloro-2-[(2-furanylmethyl)amino]benzoyloxy)propanoyloxymethoxycarbonyl]-2-(3,5-difluorophenyl)-3,5-dimethyl-2-morpholinol;

(2S,3S,5R)-4-[3-(5-(aminosulfonyl)-4-chloro-2-[(2-furanylmethyl)amino]benzoyloxy)propanoyloxymethoxycarbonyl]-2-(3,5-difluorophenyl)-3,5-dimethyl-2-morpholinol;

(2S,3S,5R)-4-[2-(5-(aminosulfonyl)-4-chloro-2-[(2-furanylmethyl)amino]benzoyloxy)butanoyloxymethoxycarbonyl]-2-(3,5-difluorophenyl)-3,5-dimethyl-2-morpholinol;

(2S,3S,5R)-4-[3-(5-(aminosulfonyl)-4-chloro-2-[(2-furanylmethyl)amino]benzoyloxy)butanoyloxymethoxycarbonyl]-2-(3,5-difluorophenyl)-3,5-dimethyl-2-morpholinol;

(2S,3S,5R)-4-[4-(5-(aminosulfonyl)-4-chloro-2-[(2-furanyl-methyl)amino]benzoyloxy)butanoyloxymethoxycarbonyl]-2-(3,5-difluorophenyl)-3,5-dimethyl-2-morpholinol;

(2S,3S,5R)-4-[4-(5-(aminosulfonyl)-4-chloro-2-[(2-furanyl-methyl)amino]benzoyloxy)crotonyloxymethoxycarbonyl]-2-(3,5-difluorophenyl)-3,5-dimethyl-2-morpholinol;

(2S,3S,5R)-4-[5-(5-(aminosulfonyl)-4-chloro-2-[(2-furanyl-methyl)amino]benzoyloxy)pentanoyloxymethoxycarbonyl]-2-(3,5-difluorophenyl)-3,5-dimethyl-2-morpholinol;

(2S,3S,5R)-4-[6-(5-(aminosulfonyl)-4-chloro-2-[(2-furanyl-methyl)amino]benzoyloxy)hexanoyloxymethoxycarbonyl]-2-(3,5-difluorophenyl)-3,5-dimethyl-2-morpholinol;

(2S,3S,5R)-4-[8-(5-(aminosulfonyl)-4-chloro-2-[(2-furanyl-methyl)amino]benzoyloxy)octanoyloxymethoxycarbonyl]-2-(3,5-difluorophenyl)-3,5-dimethyl-2-morpholinol;

(2S,3S,5R)-4-[2-(2-(5-(aminosulfonyl)-4-chloro-2-[(2-furanylmethyl)amino]benzoyloxy)ethoxy)ethanoyloxymethoxycarbonyl]-2-(3,5-difluorophenyl)-3,5-dimethyl-2-morpholinol;

(2S,3S,5R)-4-[2-(2-(5-(aminosulfonyl)-4-chloro-2-[(2-furanylmethyl)amino]benzoyloxy)ethylthio)ethanoyloxymethoxycarbonyl]-2-(3,5-difluorophenyl)-3,5-dimethyl-2-morpholinol;

(2S,3S,5R)-4-[2-(2-(5-(aminosulfonyl)-4-chloro-2-[(2-furanylmethyl)amino]benzoyloxy)ethylsulfinyl)ethanoyloxymethoxycarbonyl]-2-(3,5-difluorophenyl)-3,5-dimethyl-2-morpholinol;

(2S,3S,5R)-4-[2-(2-(5-(aminosulfonyl)-4-chloro-2-[(2-furanylmethyl)amino]benzoyloxy)ethylsulfonyl)ethanoyloxymethoxycarbonyl]-2-(3,5-difluorophenyl)-3,5-dimethyl-2-morpholinol;

(2S,3S,5R)-4-[2-((2-(5-(aminosulfonyl)-4-chloro-2-[(2-furanylmethyl)amino]benzoyloxy)ethyl)(methyl)amino)ethanoyloxymethoxycarbonyl]-2-(3,5-difluorophenyl)-3,5-dimethyl-2-morpholinol (2S,3S)-4-[2-(5-(aminosulfonyl)-4-chloro-2-[(2-furanylmethyl)amino]benzoyloxy)ethanoyloxymethoxycarbonyl]-2-(3-chlorophenyl)-3,5,5-trimethyl-2-morpholinol;

(2S,3S)-4-[2-(5-(aminosulfonyl)-4-chloro-2-[(2-furanylmethyl)amino]benzoyloxy)propanoyloxymethoxycarbonyl]-2-(3-chlorophenyl)-3,5,5-trimethyl-2-morpholinol;

(2S,3S)-4-[3-(5-(aminosulfonyl)-4-chloro-2-[(2-furanylmethyl)amino]benzoyloxy)propanoyloxymethoxycarbonyl]-2-(3-chlorophenyl)-3,5,5-trimethyl-2-morpholinol;

(2S,3S)-4-[2-(5-(aminosulfonyl)-4-chloro-2-[(2-furanylmethyl)amino]benzoyloxy)butanoyloxymethoxycarbonyl]-2-(3-chlorophenyl)-3,5,5-trimethyl-2-morpholinol;

(2S,3S)-4-[3-(5-(aminosulfonyl)-4-chloro-2-[(2-furanylmethyl)amino]benzoyloxy)butanoyloxymethoxycarbonyl]-2-(3-chlorophenyl)-3,5,5-trimethyl-2-morpholinol;

(2S,3S)-4-[4-(5-(aminosulfonyl)-4-chloro-2-[(2-furanylmethyl)amino]benzoyloxy)butanoyloxymethoxycarbonyl]-2-(3-chlorophenyl)-3,5,5-trimethyl-2-morpholinol;

(2S,3S)-4-[4-(5-(aminosulfonyl)-4-chloro-2-[(2-furanylmethyl)amino]benzoyloxy)crotonyloxymethoxycarbonyl]-2-(3-chlorophenyl)-3,5,5-trimethyl-2-morpholinol;

(2S,3S)-4-[5-(5-(aminosulfonyl)-4-chloro-2-[(2-furanylmethyl)amino]benzoyloxy)pentanoyloxymethoxycarbonyl]-2-(3-chlorophenyl)-3,5,5-trimethyl-2-morpholinol;

(2S,3S)-4-[6-(5-(aminosulfonyl)-4-chloro-2-[(2-furanylmethyl)amino]benzoyloxy)hexanoyloxymethoxycarbonyl]-2-(3-chlorophenyl)-3,5,5-trimethyl-2-morpholinol;

(2S,3S)-4-[8-(5-(aminosulfonyl)-4-chloro-2-[(2-furanylmethyl)amino]benzoyloxy)octanoyloxymethoxycarbonyl]-2-(3-chlorophenyl)-3,5,5-trimethyl-2-morpholinol;

(2S,3S)-4-[2-(2-(5-(aminosulfonyl)-4-chloro-2-[(2-furanylmethyl)amino]benzoyloxy)ethoxy)ethanoyloxymethoxycarbonyl]-2-(3-chlorophenyl)-3,5,5-trimethyl-2-morpholinol;

(2S,3S)-4-[2-(2-(5-(aminosulfonyl)-4-chloro-2-[(2-furanylmethyl)amino]benzoyloxy)ethylthio)ethanoyloxymethoxycarbonyl]-2-(3-chlorophenyl)-3,5,5-trimethyl-2-morpholinol;

(2S,3S)-4-[2-(2-(5-(aminosulfonyl)-4-chloro-2-[(2-furanylmethyl)amino]benzoyloxy)ethylsulfinyl)ethanoyloxymethoxycarbonyl]-2-(3-chlorophenyl)-3,5,5-trimethyl-2-morpholinol;

(2S,3S)-4-[2-(2-(5-(aminosulfonyl)-4-chloro-2-[(2-furanylmethyl)amino]benzoyloxy)ethylsulfonyl)ethanoyloxymethoxycarbonyl]-2-(3-chlorophenyl)-3,5,5-trimethyl-2-morpholinol;

(2S,3S)-4-[2-((2-(5-(aminosulfonyl)-4-chloro-2-[(2-furanylmethyl)amino]benzoyloxy)ethyl)(methyl)amino)ethanoyloxymethoxycarbonyl]-2-(3-chlorophenyl)-3,5,5-trimethyl-2-morpholinol;

(2S,3S,5R)-4-[2-(3-(5-(aminosulfonyl)-4-chloro-2-[(2-furanylmethyl)amino]benzoyloxy)propoxy)(2-oxo)ethanoyloxymethoxycarbonyl]-2-(3,5-difluorophenyl)-3,5-dimethyl-2-morpholinol;

(2S,3S,5R)-4-[2-(2-(5-(aminosulfonyl)-4-chloro-2-[(2-furanylmethyl)amino]benzoyloxy)ethoxy)(2-oxo)ethanoyloxymethoxycarbonyl]-2-(3,5-difluorophenyl)-3,5-dimethyl-2-morpholinol;

(2S,3S,5R)-4-[2-(4-(5-(aminosulfonyl)-4-chloro-2-[(2-furanylmethyl)amino]benzoyloxy)butoxy)(2-oxo)ethanoyloxymethoxycarbonyl]-2-(3,5-difluorophenyl)-3,5-dimethyl-2-morpholinol;

(2S,3S,5R)-4-[2-(5-(5-(aminosulfonyl)-4-chloro-2-[(2-furanylmethyl)amino]benzoyloxy)pentyloxy)(2-oxo)ethanoyloxymethoxycarbonyl]-2-(3,5-difluorophenyl)-3,5-dimethyl-2-morpholinol;

(2S,3S,5R)-4-[2-(6-(5-(aminosulfonyl)-4-chloro-2-[(2-furanylmethyl)amino]benzoyloxy)hexyloxy)(2-oxo)ethanoyloxymethoxycarbonyl]-2-(3,5-difluorophenyl)-3,5-dimethyl-2-morpholinol;

(2S,3S,5R)-4-[2-(2-(2-(5-(aminosulfonyl)-4-chloro-2-[(2-furanylmethyl)amino]benzoyloxy)ethoxy)ethoxy)(2-oxo)ethanoyloxymethoxycarbonyl]-2-(3,5-difluorophenyl)-3,5-dimethyl-2-morpholinol;

(2S,3S,5R)-4-[3-(3-(5-(aminosulfonyl)-4-chloro-2-[(2-furanylmethyl)amino]benzoyloxy)propoxy)(3-oxo)propanoyloxymethoxycarbonyl]-2-(3,5-difluorophenyl)-3,5-dimethyl-2-morpholinol;

(2S,3S,5R)-4-[3-(2-(5-(aminosulfonyl)-4-chloro-2-[(2-furanylmethyl)amino]benzoyloxy)ethoxy)(3-oxo)propanoyloxymethoxycarbonyl]-2-(3,5-difluorophenyl)-3,5-dimethyl-2-morpholinol;

(2S,3S,5R)-4-[3-(4-(5-(aminosulfonyl)-4-chloro-2-[(2-furanylmethyl)amino]benzoyloxy)butoxy)(3-oxo)propanoyloxymethoxycarbonyl]-2-(3,5-difluorophenyl)-3,5-dimethyl-2-morpholinol;

(2S,3S,5R)-4-[3-(5-(5-(aminosulfonyl)-4-chloro-2-[(2-furanylmethyl)amino]benzoyloxy)pentyloxy)(3-oxo)propanoyloxymethoxycarbonyl]-2-(3,5-difluorophenyl)-3,5-dimethyl-2-morpholinol;

(2S,3S,5R)-4-[3-(6-(5-(aminosulfonyl)-4-chloro-2-[(2-furanylmethyl)amino]benzoyloxy)hexyloxy)(3-oxo)propanoyloxymethoxycarbonyl]-2-(3,5-difluorophenyl)-3,5-dimethyl-2-morpholinol;

(2S,3S,5R)-4-[3-(2-(2-(5-(aminosulfonyl)-4-chloro-2-[(2-furanylmethyl)amino]benzoyloxy)ethoxy)ethoxy)(3-oxo)

propanoyloxymethoxycarbonyl]-2-(3,5-difluorophenyl)-3,5-dimethyl-2-morpholinol;

(2S,3S,5R)-4-[4-(3-(5-(aminosulfonyl)-4-chloro-2-[(2-furanylmethyl)amino]benzoyloxy)propoxy)(4-oxo)butanoyloxymethoxycarbonyl]-2-(3,5-difluorophenyl)-3,5-dimethyl-2-morpholinol;

(2S,3S,5R)-4-[4-(2-(5-(aminosulfonyl)-4-chloro-2-[(2-furanylmethyl)amino]benzoyloxy)ethoxy)(4-oxo)butanoyloxymethoxycarbonyl]-2-(3,5-difluorophenyl)-3,5-dimethyl-2-morpholinol;

(2S,3S,5R)-4-[4-(4-(5-(aminosulfonyl)-4-chloro-2-[(2-furanylmethyl)amino]benzoyloxy)butoxy)(4-oxo)butanoyloxymethoxycarbonyl]-2-(3,5-difluorophenyl)-3,5-dimethyl-2-morpholinol;

(2S,3S,5R)-4-[4-(5-(5-(aminosulfonyl)-4-chloro-2-[(2-furanylmethyl)amino]benzoyloxy)pentyloxy)(4-oxo)butanoyloxymethoxycarbonyl]-2-(3,5-difluorophenyl)-3,5-dimethyl-2-morpholinol;

(2S,3S,5R)-4-[4-(6-(5-(aminosulfonyl)-4-chloro-2-[(2-furanylmethyl)amino]benzoyloxy)hexyloxy)(4-oxo)butanoyloxymethoxycarbonyl]-2-(3,5-difluorophenyl)-3,5-dimethyl-2-morpholinol;

(2S,3S,5R)-4-[4-(2-(2-(5-(aminosulfonyl)-4-chloro-2-[(2-furanylmethyl)amino]benzoyloxy)ethoxy)ethoxy)(4-oxo)butanoyloxymethoxycarbonyl]-2-(3,5-difluorophenyl)-3,5-dimethyl-2-morpholinol;

(2S,3S,5R)-4-[5-(3-(5-(aminosulfonyl)-4-chloro-2-[(2-furanylmethyl)amino]benzoyloxy)propoxy)(5-oxo)pentanoyloxymethoxycarbonyl]-2-(3,5-difluorophenyl)-3,5-dimethyl-2-morpholinol;

(2S,3S,5R)-4-[5-(2-(5-(aminosulfonyl)-4-chloro-2-[(2-furanylmethyl)amino]benzoyloxy)ethoxy)(5-oxo)pentanoyloxymethoxycarbonyl]-2-(3,5-difluorophenyl)-3,5-dimethyl-2-morpholinol;

(2S,3S,5R)-4-[5-(4-(5-(aminosulfonyl)-4-chloro-2-[(2-furanylmethyl)amino]benzoyloxy)butoxy)(5-oxo)pentanoyloxymethoxycarbonyl]-2-(3,5-difluorophenyl)-3,5-dimethyl-2-morpholinol;

(2S,3S,5R)-4-[5-(5-(5-(aminosulfonyl)-4-chloro-2-[(2-furanylmethyl)amino]benzoyloxy)pentyloxy)(5-oxo)pentanoyloxymethoxycarbonyl]-2-(3,5-difluorophenyl)-3,5-dimethyl-2-morpholinol;

(2S,3S,5R)-4-[5-(6-(5-(aminosulfonyl)-4-chloro-2-[(2-furanylmethyl)amino]benzoyloxy)hexyloxy)(5-oxo)pentanoyloxymethoxycarbonyl]-2-(3,5-difluorophenyl)-3,5-dimethyl-2-morpholinol;

(2S,3S,5R)-4-[5-(2-(2-(5-(aminosulfonyl)-4-chloro-2-[(2-furanylmethyl)amino]benzoyloxy)ethoxy)ethoxy)(5-oxo)pentanoyloxymethoxycarbonyl]-2-(3,5-difluorophenyl)-3,5-dimethyl-2-morpholinol;

(2S,3S)-4-[2-(3-(5-(aminosulfonyl)-4-chloro-2-[(2-furanylmethyl)amino]benzoyloxy)propoxy)(2-oxo)ethanoyloxymethoxycarbonyl]-2-(3-chlorophenyl)-3,5,5-trimethyl-2-morpholinol;

(2S,3S)-4-[2-(2-(5-(aminosulfonyl)-4-chloro-2-[(2-furanylmethyl)amino]benzoyloxy)ethoxy)(2-oxo)ethanoyloxymethoxycarbonyl]-2-(3-chlorophenyl)-3,5,5-trimethyl-2-morpholinol;

(2S,3S)-4-[2-(4-(5-(aminosulfonyl)-4-chloro-2-[(2-furanylmethyl)amino]benzoyloxy)butoxy)(2-oxo)ethanoyloxymethoxycarbonyl]-2-(3-chlorophenyl)-3,5,5-trimethyl-2-morpholinol;

(2S,3S)-4-[2-(5-(5-(aminosulfonyl)-4-chloro-2-[(2-furanylmethyl)amino]benzoyloxy)pentyloxy)(2-oxo)ethanoyloxymethoxycarbonyl]-2-(3-chlorophenyl)-3,5,5-trimethyl-2-morpholinol;

(2S,3S)-4-[2-(6-(5-(aminosulfonyl)-4-chloro-2-[(2-furanylmethyl)amino]benzoyloxy)hexyloxy)(2-oxo)ethanoyloxymethoxycarbonyl]-2-(3-chlorophenyl)-3,5,5-trimethyl-2-morpholinol;

(2S,3S)-4-[2-(2-(2-(5-(aminosulfonyl)-4-chloro-2-[(2-furanylmethyl)amino]benzoyloxy)ethoxy)ethoxy)(2-oxo)ethanoyloxymethoxycarbonyl]-2-(3-chlorophenyl)-3,5,5-trimethyl-2-morpholinol;

(2S,3S)-4-[3-(3-(5-(aminosulfonyl)-4-chloro-2-[(2-furanylmethyl)amino]benzoyloxy)propoxy)(3-oxo)propanoyloxymethoxycarbonyl]-2-(3-chlorophenyl)-3,5,5-trimethyl-2-morpholinol;

(2S,3S)-4-[3-(2-(5-(aminosulfonyl)-4-chloro-2-[(2-furanylmethyl)amino]benzoyloxy)ethoxy)(3-oxo)propanoyloxymethoxycarbonyl]-2-(3-chlorophenyl)-3,5,5-trimethyl-2-morpholinol;

(2S,3S)-4-[3-(4-(5-(aminosulfonyl)-4-chloro-2-[(2-furanylmethyl)amino]benzoyloxy)butoxy)(3-oxo)propanoyloxymethoxycarbonyl]-2-(3-chlorophenyl)-3,5,5-trimethyl-2-morpholinol;

(2S,3S)-4-[3-(5-(5-(aminosulfonyl)-4-chloro-2-[(2-furanylmethyl)amino]benzoyloxy)pentyloxy)(3-oxo)propanoyloxymethoxycarbonyl]-2-(3-chlorophenyl)-3,5,5-trimethyl-2-morpholinol;

(2S,3S)-4-[3-(6-(5-(aminosulfonyl)-4-chloro-2-[(2-furanylmethyl)amino]benzoyloxy)hexyloxy)(3-oxo)propanoyloxymethoxycarbonyl]-2-(3-chlorophenyl)-3,5,5-trimethyl-2-morpholinol;

(2S,3S)-4-[3-(2-(2-(5-(aminosulfonyl)-4-chloro-2-[(2-furanylmethyl)amino]benzoyloxy)ethoxy)ethoxy)(3-oxo)propanoyloxymethoxycarbonyl]-2-(3-chlorophenyl)-3,5,5-trimethyl-2-morpholinol;

(2S,3S)-4-[4-(3-(5-(aminosulfonyl)-4-chloro-2-[(2-furanylmethyl)amino]benzoyloxy)propoxy)(4-oxo)butanoyloxymethoxycarbonyl]-2-(3-chlorophenyl)-3,5,5-trimethyl-2-morpholinol;

(2S,3S)-4-[4-(2-(5-(aminosulfonyl)-4-chloro-2-[(2-furanylmethyl)amino]benzoyloxy)ethoxy)(4-oxo)butanoyloxymethoxycarbonyl]-2-(3-chlorophenyl)-3,5,5-trimethyl-2-morpholinol;

(2S,3S)-4-[4-(4-(5-(aminosulfonyl)-4-chloro-2-[(2-furanylmethyl)amino]benzoyloxy)butoxy)(4-oxo)butanoyloxymethoxycarbonyl]-2-(3-chlorophenyl)-3,5,5-trimethyl-2-morpholinol;

(2S,3S)-4-[4-(5-(5-(aminosulfonyl)-4-chloro-2-[(2-furanylmethyl)amino]benzoyloxy)pentyloxy)(4-oxo)butanoyloxymethoxycarbonyl]-2-(3-chlorophenyl)-3,5,5-trimethyl-2-morpholinol;

(2S,3S)-4-[4-(6-(5-(aminosulfonyl)-4-chloro-2-[(2-furanylmethyl)amino]benzoyloxy)hexyloxy)(4-oxo)butanoyloxymethoxycarbonyl]-2-(3-chlorophenyl)-3,5,5-trimethyl-2-morpholinol;

(2S,3S)-4-[4-(2-(2-(5-(aminosulfonyl)-4-chloro-2-[(2-furanylmethyl)amino]benzoyloxy)ethoxy)ethoxy)(4-oxo)butanoyloxymethoxycarbonyl]-2-(3-chlorophenyl)-3,5,5-trimethyl-2-morpholinol;

(2S,3S)-4-[5-(3-(5-(aminosulfonyl)-4-chloro-2-[(2-furanylmethyl)amino]benzoyloxy propoxy)(5-oxo)pentanoyloxymethoxycarbonyl]-2-(3-chlorophenyl)-3,5,5-trimethyl-2-morpholinol;

(2S,3S)-4-[5-(2-(5-(aminosulfonyl)-4-chloro-2-[(2-furanylmethyl)amino]benzoyloxy)ethoxy)(5-oxo)pentanoyloxymethoxycarbonyl]-2-(3-chlorophenyl)-3,5,5-trimethyl-2-morpholinol;

(2S,3S)-4-[5-(4-(5-(aminosulfonyl)-4-chloro-2-[(2-furanyl-methyl)amino]benzoyloxy)butoxy)(5-oxo)pentanoy-loxymethoxycarbonyl]-2-(3-chlorophenyl)-3,5,5-trim-ethyl-2-morpholinol;

(2S,3S)-4-[5-(5-(5-(aminosulfonyl)-4-chloro-2-[(2-furanyl-methyl)amino]benzoyloxy)pentyloxy)(5-oxo)pentanoy-loxymethoxycarbonyl]-2-(3-chlorophenyl)-3,5,5-trim-ethyl-2-morpholinol;

(2S,3S)-4-[5-(6-(5-(aminosulfonyl)-4-chloro-2-[(2-furanyl-methyl)amino]benzoyloxy)hexyloxy)(5-oxo)pentanoy-loxymethoxycarbonyl]-2-(3-chlorophenyl)-3,5,5-trim-ethyl-2-morpholinol;

(2S,3S)-4-[5-(2-(2-(5-(aminosulfonyl)-4-chloro-2-[(2-fura-nylmethyl)amino]benzoyloxy)ethoxy)ethoxy)(5-oxo)pentanoyloxymethoxycarbonyl]-2-(3-chlorophenyl)-3,5,5-trimethyl-2-morpholinol;

2-[(5-(aminosulfonyl)-4-chloro-2-[(2-furanylmethyl)amino]benzoyloxymethoxycarbonyl)(1,1-dimethylethyl)amino]-1-(3-chlorophenyl)-1-propanone;

2-[(2-(5-(aminosulfonyl)-4-chloro-2-[(2-furanylmethyl)amino]benzoyloxy)ethanoyloxymethoxycarbonyl)(1,1-dimethylethyl)amino]-1-(3-chlorophenyl)-1-propanone;

2-[(2-(5-(aminosulfonyl)-4-chloro-2-[(2-furanylmethyl)amino]benzoyloxy)propanoyloxymethoxycarbonyl)(1,1-dimethylethyl)amino]-1-(3-chlorophenyl)-1-propanone;

2-[(3-(5-(aminosulfonyl)-4-chloro-2-[(2-furanylmethyl)amino]benzoyloxy)propanoyloxymethoxycarbonyl)(1,1-dimethylethyl)amino]-1-(3-chlorophenyl)-1-propanone;

2-[(2-(5-(aminosulfonyl)-4-chloro-2-[(2-furanylmethyl)amino]benzoyloxy)butanoyloxymethoxycarbonyl)(1,1-dimethylethyl)amino]-1-(3-chlorophenyl)-1-propanone;

2-[(3-(5-(aminosulfonyl)-4-chloro-2-[(2-furanylmethyl)amino]benzoyloxy)butanoyloxymethoxycarbonyl)(1,1-dimethylethyl)amino]-1-(3-chlorophenyl)-1-propanone;

2-[(4-(5-(aminosulfonyl)-4-chloro-2-[(2-furanylmethyl)amino]benzoyloxy)butanoyloxymethoxycarbonyl)(1,1-dimethylethyl)amino]-1-(3-chlorophenyl)-1-propanone;

2-[(4-(5-(aminosulfonyl)-4-chloro-2-[(2-furanylmethyl)amino]benzoyloxy)crotonyloxymethoxycarbonyl)(1,1-dimethylethyl)amino]-1-(3-chlorophenyl)-1-propanone;

2-[(5-(5-(aminosulfonyl)-4-chloro-2-[(2-furanylmethyl)amino]benzoyloxy)pentanoyloxymethoxycarbonyl)(1,1-dimethylethyl)amino]-1-(3-chlorophenyl)-1-propanone;

2-[(6-(5-(aminosulfonyl)-4-chloro-2-[(2-furanylmethyl)amino]benzoyloxy)hexanoyloxymethoxycarbonyl)(1,1-dimethylethyl)amino]-1-(3-chlorophenyl)-1-propanone;

2-[(8-(5-(aminosulfonyl)-4-chloro-2-[(2-furanylmethyl)amino]benzoyloxy)octanoyloxymethoxycarbonyl)(1,1-dimethylethyl)amino]-1-(3-chlorophenyl)-1-propanone;

2-[(2-(2-(5-(aminosulfonyl)-4-chloro-2-[(2-furanylmethyl)amino]benzoyloxy)ethoxy)ethanoyloxymethoxycarbo-nyl)(1,1-dimethylethyl)amino]-1-(3-chlorophenyl)-1-propanone;

2-[(2-(2-(5-(aminosulfonyl)-4-chloro-2-[(2-furanylmethyl)amino]benzoyloxy)ethylthio)ethanoyloxymethoxycarbo-nyl)(1,1-dimethylethyl)amino]-1-(3-chlorophenyl)-1-propanone;

2-[(2-(2-(5-(aminosulfonyl)-4-chloro-2-[(2-furanylmethyl)amino]benzoyloxy)ethylsulfinyl)ethanoyloxymethoxy-carbonyl)(1,1-dimethylethyl)amino]-1-(3-chlorophenyl)-1-propanone;

2-[(2-(2-(5-(aminosulfonyl)-4-chloro-2-[(2-furanylmethyl)amino]benzoyloxy)ethylsulfonyl)ethanoyloxymethoxy-carbonyl)(1,1-dimethylethyl)amino]-1-(3-chlorophenyl)-1-propanone;

2-[(2-((2-(5-(aminosulfonyl)-4-chloro-2-[(2-furanylmethyl)amino]benzoyloxy)ethyl)(methyl)amino)ethanoy-loxymethoxycarbonyl) (1,1-dimethylethyl)amino]-1-(3-chlorophenyl)-1-propanone;

2-[(2-(3-(5-(aminosulfonyl)-4-chloro-2-[(2-furanylmethyl)amino]benzoyloxy)propoxy)(2-oxo)ethanoy-loxymethoxycarbonyl)(1,1-dimethylethyl)amino]-1-(3-chlorophenyl)-1-propanone;

2-[(2-(2-(5-(aminosulfonyl)-4-chloro-2-[(2-furanylmethyl)amino]benzoyloxy)ethoxy)(2-oxo)ethanoyloxymethoxy-carbonyl)(1,1-dimethylethyl)amino]-1-(3-chlorophenyl)-1-propanone;

2-[(2-(4-(5-(aminosulfonyl)-4-chloro-2-[(2-furanylmethyl)amino]benzoyloxy)butoxy)(2-oxo)ethanoyloxymethoxy-carbonyl)(1,1-dimethylethyl)amino]-1-(3-chlorophenyl)-1-propanone;

2-[(2-(5-(5-(aminosulfonyl)-4-chloro-2-[(2-furanylmethyl)amino]benzoyloxy)pentyloxy)(2-oxo)ethanoy-loxymethoxycarbonyl)(1,1-dimethylethyl)amino]-1-(3-chlorophenyl)-1-propanone;

2-[(2-(6-(5-(aminosulfonyl)-4-chloro-2-[(2-furanylmethyl)amino]benzoyloxy)hexyloxy)(2-oxo)ethanoy-loxymethoxycarbonyl)(1,1-dimethylethyl)amino]-1-(3-chlorophenyl)-1-propanone;

2-[(2-(2-(2-(5-(aminosulfonyl)-4-chloro-2-[(2-furanylm-ethyl)amino]benzoyloxy)ethoxy)ethoxy)(2-oxo)ethanoy-loxymethoxycarbonyl)(1,1-dimethylethyl)amino]-1-(3-chlorophenyl)-1-propanone;

2-[(3-(3-(5-(aminosulfonyl)-4-chloro-2-[(2-furanylmethyl)amino]benzoyloxy)propoxy)(3-oxo)propanoy-loxymethoxycarbonyl)(1,1-dimethylethyl)amino]-1-(3-chlorophenyl)-1-propanone;

2-[(3-(2-(5-(aminosulfonyl)-4-chloro-2-[(2-furanylmethyl)amino]benzoyloxy)ethoxy)(3-oxo)propanoy-loxymethoxycarbonyl)(1,1-dimethylethyl)amino]-1-(3-chlorophenyl)-1-propanone;

2-[(3-(4-(5-(aminosulfonyl)-4-chloro-2-[(2-furanylmethyl)amino]benzoyloxy)butoxy)(3-oxo)propanoy-loxymethoxycarbonyl)(1,1-dimethylethyl)amino]-1-(3-chlorophenyl)-1-propanone;

2-[(3-(5-(5-(aminosulfonyl)-4-chloro-2-[(2-furanylmethyl)amino]benzoyloxy)pentyloxy)(3-oxo)propanoy-loxymethoxycarbonyl)(1,1-dimethylethyl)amino]-1-(3-chlorophenyl)-1-propanone;

2-[(3-(6-(5-(aminosulfonyl)-4-chloro-2-[(2-furanylmethyl)amino]benzoyloxy)hexyloxy)(3-oxo)propanoy-loxymethoxycarbonyl)(1,1-dimethylethyl)amino]-1-(3-chlorophenyl)-1-propanone;

2-[(3-(2-(2-(5-(aminosulfonyl)-4-chloro-2-[(2-furanylm-ethyl)amino]benzoyloxy)ethoxy)ethoxy)(3-oxo)pro-panoyloxymethoxycarbonyl)(1,1-dimethylethyl)amino]-1-(3-chlorophenyl)-1-propanone;

2-[(4-(3-(5-(aminosulfonyl)-4-chloro-2-[(2-furanylmethyl)amino]benzoyloxy)propoxy)(4-oxo)butanoy-loxymethoxycarbonyl)(1,1-dimethylethyl)amino]-1-(3-chlorophenyl)-1-propanone;

2-[(4-(2-(5-(aminosulfonyl)-4-chloro-2-[(2-furanylmethyl)amino]benzoyloxy)ethoxy)(4-oxo)butanoyloxymethoxy-carbonyl)(1,1-dimethylethyl)amino]-1-(3-chlorophenyl)-1-propanone;

2-[(4-(4-(5-(aminosulfonyl)-4-chloro-2-[(2-furanylmethyl)amino]benzoyloxy)butoxy)(4-oxo)butanoyloxymethoxy-carbonyl)(1,1-dimethylethyl)amino]-1-(3-chlorophenyl)-1-propanone;

2-[(4-(5-(5-(aminosulfonyl)-4-chloro-2-[(2-furanylmethyl)amino]benzoyloxy)pentyloxy)(4-oxo)butanoyloxymethoxycarbonyl)(1,1-dimethylethyl)amino]-1-(3-chlorophenyl)-1-propanone;

2-[(4-(6-(5-(aminosulfonyl)-4-chloro-2-[(2-furanylmethyl)amino]benzoyloxy)hexyloxy)(4-oxo)butanoyloxymethoxycarbonyl)(1,1-dimethylethyl)amino]-1-(3-chlorophenyl)-1-propanone;

2-[(4-(2-(2-(5-(aminosulfonyl)-4-chloro-2-[(2-furanylmethyl)amino]benzoyloxy)ethoxy)ethoxy)(4-oxo)butanoyloxymethoxycarbonyl)(1,1-dimethylethyl)amino]-1-(3-chlorophenyl)-1-propanone;

2-[(5-(3-(5-(aminosulfonyl)-4-chloro-2-[(2-furanylmethyl)amino]benzoyloxy)propoxy)(5-oxo)pentanoyloxymethoxycarbonyl)(1,1-dimethylethyl)amino]-1-(3-chlorophenyl)-1-propanone;

2-[(5-(2-(5-(aminosulfonyl)-4-chloro-2-[(2-furanylmethyl)amino]benzoyloxy)ethoxy)(5-oxo)pentanoyloxymethoxycarbonyl)(1,1-dimethylethyl)amino]-1-(3-chlorophenyl)-1-propanone;

2-[(5-(4-(5-(aminosulfonyl)-4-chloro-2-[(2-furanylmethyl)amino]benzoyloxy)butoxy)(5-oxo)pentanoyloxymethoxycarbonyl)(1,1-dimethylethyl)amino]-1-(3-chlorophenyl)-1-propanone;

2-[(5-(5-(5-(aminosulfonyl)-4-chloro-2-[(2-furanylmethyl)amino]benzoyloxy)pentyloxy)(5-oxo)pentanoyloxymethoxycarbonyl)(1,1-dimethylethyl)amino]-1-(3-chlorophenyl)-1-propanone;

2-[(5-(6-(5-(aminosulfonyl)-4-chloro-2-[(2-furanylmethyl)amino]benzoyloxy)hexyloxy)(5-oxo)pentanoyloxymethoxycarbonyl)(1,1-dimethylethyl)amino]-1-(3-chlorophenyl)-1-propanone; and 2-[(5-(2-(2-(5-(aminosulfonyl)-4-chloro-2-[(2-furanylmethyl)amino]benzoyloxy)ethoxy)ethoxy)(5-oxo)pentanoyloxymethoxycarbonyl)(1,1-dimethylethyl)amino]-1-(3-chlorophenyl)-1-propanone.

Animal Studies of Therapeutic Amine-Arylsulfonamide Conjugate Compound

Substances having an antidepressant action antagonize a number of the behavioral effects induced by tetrabenazine including locomotor activity, ptosis and hypothermia. Tetrabenazine-induced behavioral effects can be quantified using a composite index, X, where X=(1−ptosis score)/(activity score*[Temp., treated/Temp., control]) as described by Cooper, B. R., J. L. Howard, and F. E. Soroko, Animal models used in prediction of antidepressant effects in man, *Journal of Clinical Psychiatry* 44:63-6, 1983). 50% effective dose ($ED_{50}$) values indicate a dose of compound with 'antitetrabenazine activity' at which the composite index, X, induced by 20 mg/kg of tetrabenazine intraperitoneally is reduced 50%.

Prevention of tetrabenazine-induced behavioral effects were measured using a modification of the method of Vernier et al., First Hahnemann Symposium on Psychosomatic Medicine, ed. Nodim and Moyer, pub Lea and Febiger, Philadelphia 1962 as described previously (Cooper, B. R., J. L. Howard, and F. E. Soroko, Animal models used in prediction of antidepressant effects in man, *Journal of Clinical Psychiatry* 44:63-6, 1983). Mice, groups of 12 CD1 males each, were injected intraperitoneally (i.p.) with the compounds (1420), (20a) and furosemide (10) suspended in a 0.5% 4000-centipoise methyl cellulose solution at 3 mg/mL or vehicle. All injections were administered at a vehicle volume of 10 ml/kg. The 50% effective dose ($ED_{50}$) of each compound was determined by linear regression analysis of log probit plots of dose effect curves and is reported in Table 3:

TABLE 3

Antitetrabenazine Activity in the Mouse

| Compound | $ED_{50}$ (mg/kg i.p.) |
|---|---|
| (2S,3S,5R)-4-[5-(aminosulfonyl)-4-chloro-2-[(2-furanylmethyl)amino]benzoyloxymethoxycarbonyl]-2-(3,5-difluorophenyl)-3,5-dimethyl-2-morpholinol (1420) | 3.6 |
| (2S,3S,5R)-2-(3,5-difluorophenyl)-2-hydroxy-3,5-dimethylmorpholine (20a) | 0.2 |
| furosemide (10) | >30 |

Thus, conjugate compound (1420) inhibited tetrabenazine-induced behavioral effects as did the therapeutic amine compound (20a).

Safety and Toxicity: Dose-ranging studies were performed to determine the range of safe doses for compound (1420). Animals were observed for the presence of serious adverse events (e.g. seizures and deaths) following administration of compound (1420) by the oral route. Mice, groups of 6 CD1 males each, were administered compound suspended in a 0.5% 4000-centipoise methyl cellulose vehicle at a volume of 10 mL/kg p.o. using a 22-gauge stainless steel mouse feeding tube and 1-mL syringe at doses up to 300 mg/kg. Animals were observed for a period of one hour. No seizures or deaths were observed in any animals at any dose (data not shown).

The following examples illustrated above are also representative of pharmaceutical compositions where the "Active Ingredient" may be any conjugate compound of (I) or a pharmaceutical acceptable salt thereof.

The conjugate compounds herein disclosed may be produced by a method of reacting at least one therapeutic amine radical, at least one arylsulfonamide radical, and optionally a linker as described above.

Methods of using therapeutic amine-arylsulfonamide conjugate compounds include, for example, the treatment of psychiatric, neurologic and metabolic disorders such as depression, obesity, fibromyalgia, neuropathic pain, restless leg syndrome, attention deficit hyperactivity disorder (ADHD), migraine, pain, sexual dysfunction, Parkinson's disease, Alzheimer's disease, anxiety, narcolepsy-cataplexy syndrome, seizures or drug/substance addiction/cessation. In embodiments, the use of a therapeutic amine-arylsulfonamide conjugate compound as described herein is provided for the manufacture of a composition intended to treat a known or potential convulsant condition, a known or potential proconvulsant condition, a known or potential abuse liability, one or more psychiatric disorders and/or one or more neurologic disorders and/or one or more metabolic disorders in an individual in need thereof by administering a therapeutically effective amount of the therapeutic amine-arylsulfonamide conjugate.

Conjugate compounds described herein may be administered to a patient in a variety of routes, for example, orally, parenterally, intravenously, intradermally, intranasally, subcutaneously, or topically, in liquid, cream, gel or solid form. The conjugate compounds may be formulated into, for example, a reconstitutable powder, a paste, ointment, cream, gel, or transdermal patch. For example, an oral administration of the conjugate compounds for therapeutic amine compounds with potential seizure or abuse liability would be the preferred method of administration.

In most embodiments, the conjugate compound will contain the substances to be delivered in an amount sufficient to deliver to a patient a therapeutically effective amount of at least one of the individual components of the conjugated compound and independently or simultaneously alleviate or ameliorate the severity of, or reduce the likelihood of, adverse effects of one or more of the individual components of the conjugate compound. The desired concentration of either compound in the conjugate compound will depend on absorption, inactivation, and excretion rates. Dosage values may also vary with the severity of the condition to be alleviated. Effective amounts of each constituent of the conjugate compound are known or may be determined by routine experimentation. Thus, appropriate combinations of each constituent of the conjugate compound are determinable by one skilled in the art, for example, by selection of the appropriate chemical linker to provide the desired molar ratio of therapeutic amine radical to arylsulfonamide radical.

Such factors to be considered in selecting the appropriate ratio of therapeutic amine to arylsulfonamide include, but are not limited to: the enzymatic degradability and enzymatic cleavability of the chemical linker; the bioavailability of each constituent therapeutic amine and arylsulfonamide and combinations thereof; interactions between the constituents; pharmacokinetic and pharmacodynamic properties of the therapeutic amine and arylsulfonamide and combinations thereof; and the degree and severity of the patient's condition. Further, for any particular patient, specific dosage regimens may be adjusted over time according to the individual need and the professional judgment of the person administering or supervising the administration of the conjugate compound compositions.

The conjugate compounds may be administered once, or may be divided into a number of smaller doses to be administered at varying intervals of time, depending in part on the in vivo degradation rate of the linker and the desired dosage.

Those skilled in the art will recognize, or be able to ascertain using no more than routine experimentation, many equivalents to the specific embodiments of the invention described herein.

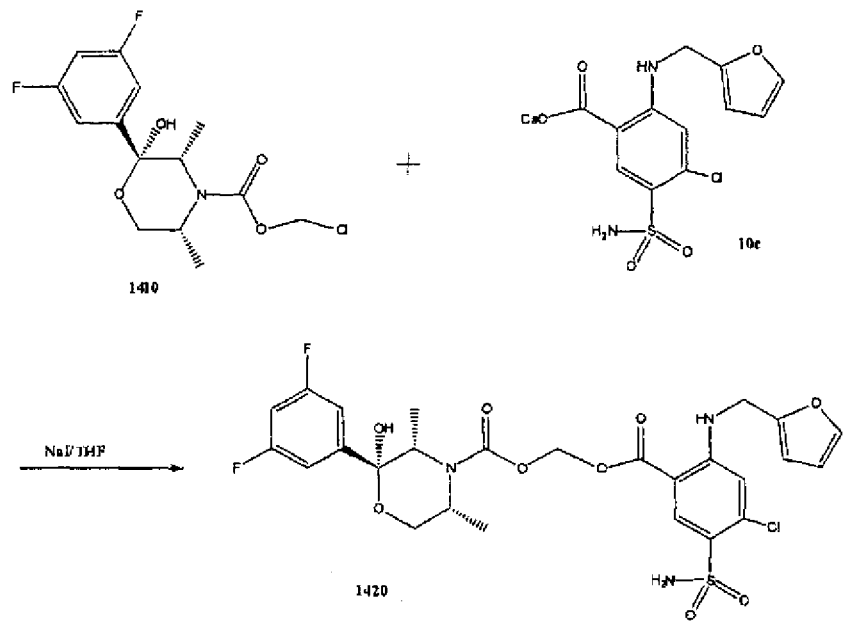

The invention claimed is:

1. A therapeutic amine-arylsulfonamide conjugate compound, comprising structure (I):

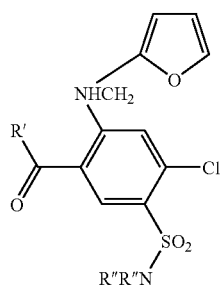

(I)

wherein
R' is [D-W-], hydroxyl, or alkoxyl;
R" is independently [D-W'-], hydrogen, alkyl, or alkoxyl;
D is independently a therapeutic amine radical comprising at least one nitrogen atom and optionally at least one oxygen atom coupled to W or W' by a nitrogen or oxygen atom;
W and W' are a chemical bond or linker;
wherein either R' is [D-W-] or at least one R" is [D-W'-]; and pharmaceutically acceptable esters, amides, salts or solvates thereof;
wherein the therapeutic amine radical is derived from amines selected from the group consisting of: manifaxine; 2-(1-(3,5-difluorobenzoyl)-(R,S)-ethylamino)-(R)-2-methylethanol; (2S,3S)-2-(3-chlorophenyl)-3,5,5-trimethyl-2-morpholinol; radafaxine; 2-(1-(3-chlorobenzoyl)-(R,S)-ethylamino)-2,2-dimethylethanol; bupropion; citalopram; escitalopram; paroxetine; fluoxetine; fluvoxamine; sertraline; phenelzine; tranylcypromine; amitriptyline; amoxapine; clomipramine; desipramine; doxepine; imipramine; nortryptyline; protriptyline; trimipramine; maprotiline; mirtazapine; duloxetine; nefazodone; trazodone; and venlafaxine.

2. The therapeutic amine-arylsulfonamide conjugate compound of claim 1, wherein the therapeutic amine radical is derived from amines selected from the group consisting of: manifaxine; 2-(1-(3,5-difluorobenzoyl)-(R,S)-ethylamino)-(R)-2-methylethanol; (2S,3S)-2-(3-chlorophenyl)-3,5,5-trimethyl-2-morpholinol; radafaxine; 2-(1-(3-chlorobenzoyl)-(R,S)-ethylamino)-2,2-dimethylethanol; bupropion; citalopram; escitalopram; paroxetine; fluoxetine; fluvoxamine; sertraline; phenelzine; tranylcypromine; amitriptyline; amoxapine; clomipramine; desipramine; doxepine; imipramine; nortryptyline; protriptyline; trimipramine; maprotiline; mirtazapine; duloxetine; nefazodone; trazodone; and venlafaxine.

3. The therapeutic amine-arylsulfonamide conjugate of claim 1, wherein at least one of the R" is cycloalkyl, alkenyl, alkynyl, or aryl optionally substituted with alkyl, hydroxy, hydroxyalkyl, alkoxy, amino, mercapto, nitro, or cyano.

4. The therapeutic amine-arylsulfonamide conjugate of claim 1, wherein the R" and R" together with the nitrogen atom to which they are attached form a 4-, 5-, 6-, 7- or 8-membered ring optionally containing one or two further heteroatoms independently selected from nitrogen, oxygen and sulfur, the ring being optionally substituted by hydroxy, hydroxyalkyl, oxo, alkyl, haloalkyl, and/or haloalkoxy.

5. The therapeutic amine-arylsulfonamide conjugate of claim 1, wherein the linker W is selected from the group consisting of:
—CHRO—;
—C(O)OCHRO—;
—C(O)OCHROC(O)R$^1$O—;
—C(O)R$^1$O—;
—CHROC(O)R$^1$O—;
—C(O)R$^1$OC(O)R$^1$O—; and
—CHROC(O)R$^1$OC(O)R$^1$O—;
wherein
R$^1$ is, independently,
—(CH$_2$)$_n$—;
—(CH$_2$)$_o$CHY(CH$_2$)$_n$—;
—(CH$_2$)$_o$CH═CH(CH$_2$)$_n$—;
—(CH$_2$)$_n$O(CH$_2$)$_n$—;
—(CH$_2$)$_n$NR(CH$_2$)$_n$—;
—(CH$_2$)OC═C(CH$_2$)$_n$—;
—(CH$_2$)$_n$C(O)O(CH$_2$)$_n$—;
—(CH$_2$)$_n$C(O)O(CH$_2$)$_n$CHY(CH$_2$)$_n$—;
—(CH$_2$)$_n$C(O)O(CH$_2$)$_n$CH═CH(CH$_2$)$_n$—;
—(CH$_2$)$_n$C(O)O(CH$_2$)$_n$O(CH$_2$)$_n$—;
—(CH$_2$)$_n$C(O)O(CH$_2$)$_n$NR(CH$_2$)$_n$—;
—(CH$_2$)$_n$C(O)O(CH$_2$)$_n$S(O)$_m$(CH$_2$)$_n$—;
—(CH$_2$)$_n$C(O)O(CH$_2$)$_n$C═C(CH$_2$)$_n$—; or
a 5- or 6-membered aromatic ring diradical optionally containing 1 or more heteroatoms independently selected from oxygen, nitrogen and sulfur, the 5- or 6-membered aromatic ring diradical optionally substituted by hydroxy, hydroxyalkyl, halogen, amino, alkyl, or alkoxyalkyl;
R is independently hydrogen, alkyl, cycloalkyl or aryl;

Y is a halogen;
n is independently 1-8;
m is 0, 1, or 2; and
o is 0-8.

6. The therapeutic amine-arylsulfonamide conjugate of claim 1, wherein the linker W' is selected from the group consisting of:
—CHROC(O)R$^1$C(O)OCHR—;
—C(O)R$^1$C(O)OCHR—;
—C(O)OCHROC(O)R$^1$C(O)OCHR—;
—CHROC(O)R$^1$C(O)OCHROC(O)—;
—C(O)R$^1$C(O)OCHROC(O)—; and
—C(O)OCHROC(O)R$^1$C(O)OCHROC(O)—;
wherein
R$^1$ is independently
—(CH$_2$)$_n$—;
—(CH$_2$)$_o$CHY(CH$_2$)$_n$—;
—(CH$_2$)$_o$CH=CH(CH$_2$)$_n$—;
—(CH$_2$)$_n$O(CH$_2$)$_n$—;
—(CH$_2$)$_n$NR(CH$_2$)$_n$—;
—(CH$_2$)$_n$C≡C(CH$_2$)$_n$—;
—(CH$_2$)$_n$C(O)O(CH$_2$)$_n$—;
—(CH$_2$)$_n$C(O)O(CH$_2$)$_n$CHY(CH$_2$)$_n$—;
—(CH$_2$)$_n$C(O)O(CH$_2$)$_n$CH=CH(CH$_2$)$_n$—;
—(CH$_2$)$_n$C(O)O(CH$_2$)$_n$O(CH$_2$)$_n$—;
—(CH$_2$)$_n$C(O)O(CH$_2$)$_n$NR(CH$_2$)$_n$—;
—(CH$_2$)$_n$C(O)O(CH$_2$)$_n$S(O)$_m$(CH$_2$)$_n$—;
—(CH$_2$)$_n$C(O)O(CH$_2$)$_n$C≡C(CH$_2$)$_n$— or;
a 5- or 6-membered aromatic ring diradical optionally containing 1 or more heteroatoms independently selected from oxygen, nitrogen and sulfur, the 5- or 6-membered aromatic ring diradical optionally substituted by hydroxy, hydroxyalkyl, halogen, amino, alkyl, or alkoxyalkyl;
R is independently hydrogen, alkyl, cycloalkyl or aryl;
Y is a halogen;
n is independently 1-8;
m is 0, 1, or 2; and
o is 0-8.

7. The therapeutic amine-arylsulfonamide conjugate of claim 1, wherein W or W' is enzymatically degradable in vivo.

8. The therapeutic amine-arylsulfonamide conjugate of claim 1, wherein said D or said arylsulfonamide is enzymatically cleaved in vivo from said chemical bond or linker.

9. The therapeutic amine-arylsulfonamide conjugate of claim 1, wherein said D or said arylsulfonamide is physiologically hydrolyzed in vivo from said chemical bond or linker.

10. The therapeutic amine-arylsulfonamide conjugate of claim 1, wherein said therapeutic amine-arylsulfonamide conjugate is:
(2S,3S,5R)-4-[5-(aminosulfonyl)-4-chloro-2-[(2-furanylmethyl)amino]benzoyloxymethoxycarbonyl]-2-(3,5-difluorophenyl)-3,5-dimethyl-2-morpholinol;
(2 S,3S,5R)-4-[2-(5-(aminosulfonyl)-4-chloro-2-[(2-furanylmethyl)amino]benzoyloxy)ethanoyloxymethoxycarbonyl]-2-(3,5-difluorophenyl)-3,5-dimethyl-2-morpholinol;
(2S,3S,5R)-4-[2-(2-(5-(aminosulfonyl)-4-chloro-2-[(2-furanylmethyl)amino]benzoyloxy)ethoxy)ethanoyloxymethoxycarbonyl]-2-(3,5-difluorophenyl)-3,5-dimethyl-2-morpholinol;
(2S,3S)-4-[5-(aminosulfonyl)-4-chloro-2-[(2-furanylmethyl)amino]benzoyloxymethoxycarbonyl]-2-(3-chlorophenyl)-3,5,5-trimethyl-2-morpholinol;
(2 S,3S)-4-[2-(5-(aminosulfonyl)-4-chloro-2-[(2-furanylmethyl)amino]benzoyloxy)ethanoyloxymethoxycarbonyl]-2-(3-chlorophenyl)-3,5,5-trimethyl-2-morpholinol;
2-(1-(3,5-difluorobenzoyl)-(R,S)-ethylamino)-(R)-2-methylethyl 4-(3-(5 (aminosulfonyl)-4-chloro-2-[(2-furanylmethyl)amino]benzoyloxy)propoxy)(4-oxo)butanoate;
2-(1-(3-chlorobenzoyl)-(R,S)-ethylamino)-2,2-dimethylethyl 4-(3-(5-(aminosulfonyl)-4-chloro-2-[(2-furanylmethyl)amino]benzoyloxy)propoxy)(4-oxo)butanoate;
2-[(5-(aminosulfonyl)-4-chloro-2-[(2-furanylmethyl)amino]benzoyloxymethoxycarbonyl)(1,1-dimethylethypamino]-1-(3-chlorophenyl)-1-propanone;
2-[(2-(5-(aminosulfonyl)-4-chloro-2-[(2-furanylmethyl)amino]benzoyloxy)ethanoyloxymethoxycarbonyl)(1,1-dimethylethyl)amino-1-(3-chlorophenyl)-1-propanone;
2-(1-(3,5-difluorobenzoyl)-(R,S)-ethylamino)-(R)-2-methylethyl 5-(aminosulfonyl)-4-chloro-2-[(2-furanylmethyl)amino]benzoate;
2-(1-(3-chlorobenzoyl)-(R,S)-ethylamino)-2,2-dimethylethyl 5-(aminosulfonyl)-4-chloro-2-[(2-furanylmethyl)amino]benzoate; or
2-(1-(3,5-difluorobenzoyl)-(R,S)-ethylamino)-(R)-2-methylethyl 6-(5-carboxy-2-chloro-4-[(2-furanylmethyl)amino]phenylsulfonamidocarbonyloxymethoxy)(6-oxo)hexanoate.

11. A method of making a therapeutic amine-sulfonamide conjugate compound as defined in claim 1, comprising:
reacting a therapeutic amine radical, an arylsulfonamide radical, and optionally a linker; and
isolating a therapeutic amine-arylsulfonamide conjugate compound connected by a chemical bond or the linker, or a pharmaceutically acceptable salt or solvate of said therapeutic amine-arylsulfonamide conjugate compound.

12. A method of ameliorating or attenuating a known or potential convulsant, pro-convulsant, or abuse liability condition, said condition resulting from administration of a therapeutic amine, comprising: administering to a patient in need thereof a therapeutically effective amount of an therapeutic amine-arylsulfonamide conjugate compound (I):

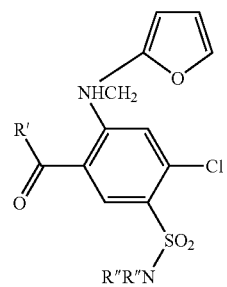

(I)

wherein
R' is [D-W-], hydroxyl, or alkoxyl;
R" is independently [D-W'-], hydrogen, alkoxy, alkyl, cycloalkyl, alkenyl, alkynyl or aryl, or R" and R" together with the nitrogen atom to which they are attached form a 4-, 5-, 6-, 7- or 8-membered ring optionally containing one or two further heteroatoms independently selected from nitrogen, oxygen and sulfur;

D is independently a therapeutic amine radical comprising at least one nitrogen atom and optionally at least one oxygen atom coupled to W or W' by a nitrogen or oxygen atom;

W and W' are a chemical bond or linker;

wherein either R' is [D-W-] or at least one R" is [D-W'-], and pharmaceutically acceptable esters, amides, salts or solvates thereof.

13. The method of claim 12, wherein the therapeutic amine radical is derived from amines selected from the group consisting of: manifaxine; 2-(1-(3,5-difluorobenzoyl)-(R,S)-ethylamino)-(R)-2-methylethanol; (2S,3S)-2-(3-chlorophenyl)-3,5,5-trimethyl-2-morpholinol; radafaxine; 2-(1-(3-chlorobenzoyl)-(R,S)-ethylamino)-2,2-dimethylethanol; bupropion; citalopram; escitalopram; paroxetine; fluoxetine; fluvoxamine; sertraline; phenelzine; tranylcypromine; amitriptyline; amoxapine; clomipramine; desipramine; doxepine; imipramine; nortryptyline; protriptyline; trimipramine; maprotiline; mirtazapine; duloxetine; nefazodone; trazodone; and venlafaxine.

14. A method of treating one or more or a combination of one or more of a psychiatric, a neurologic and/or a metabolic disorder, the method comprising:

administering to a patient in need thereof a therapeutically effective amount of a therapeutic amine-arylsulfonamide conjugate compound (I):

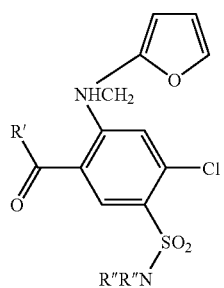

(I)

wherein
R' is [D-W-], hydroxyl, or alkoxyl;

R" is independently [D-W'-], hydrogen, alkoxy, alkyl, cycloalkyl, alkenyl, alkynyl or aryl, or R" and R" together with the nitrogen atom to which they are attached form a 4-, 5-, 6-, 7- or 8-membered ring optionally containing one or two further heteroatoms independently selected from nitrogen, oxygen and sulfur;

D is independently a therapeutic amine radical comprising at least one nitrogen atom and optionally at least one oxygen atom coupled to W or W' by a nitrogen or oxygen atom;

W and W' are a chemical bond or linker;

wherein either R' is [D-W-] or at least one R" is [D-W'-], and pharmaceutically acceptable esters, amides, salts or solvates thereof.

15. The method of claim 14, wherein the psychiatric, neurologic and/or metabolic disorder is depression, obesity, fibromyalgia, neuropathic pain, restless leg syndrome, attention deficit hyperactivity disorder (ADHD), migraine, pain, sexual dysfunction, Parkinson's disease, Alzheimer's disease, anxiety, narcolepsy-cataplexy syndrome, seizures, drug/substance addiction/cessation or combinations thereof.

16. A therapeutic amine-arylsulfonamide conjugate compound: (2 S,3S,5R)-4-[5-(aminosulfonyl)-4-chloro-2-[(2-furanylmethyl)amino]benzoyloxymethoxycarbonyl]-2-(3,5-difluorophenyl)-3,5-dimethyl-2-morpholinol, represented by the structure:

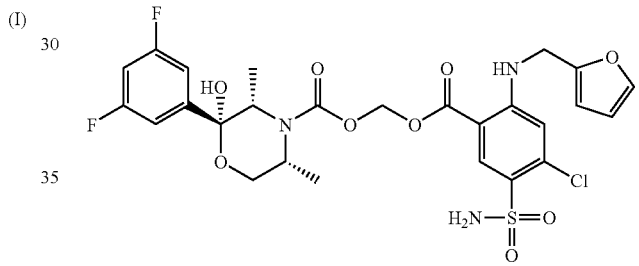

and pharmaceutically acceptable esters, amides, salts or solvates thereof.

* * * * *

UNITED STATES PATENT AND TRADEMARK OFFICE
CERTIFICATE OF CORRECTION

Page 1 of 2

PATENT NO.        : 7,763,612 B2
APPLICATION NO.   : 11/619291
DATED             : July 27, 2010
INVENTOR(S)       : Philip F. Morgan et al.

It is certified that error appears in the above-identified patent and that said Letters Patent is hereby corrected as shown below:

Columns 15 and 16: Lines 25-30: In the middle of column, just above the row beginning with "i" the words "wherein R1 may be" are missing.

Columns 35 and 36, Lines 10-45: Scheme designation "Scheme D" is missing.

Columns 37 and 38, Lines 35-65: Scheme designation "Scheme E" is missing.

Columns 41 and 42, Lines 5-30: Scheme designation "Scheme F" is missing.

Columns 43 and 44, Lines 5-40: Scheme designation "Scheme G" is missing.

Columns 45 and 46, Lines 30-60: Scheme designation "Scheme H" is missing.

Columns 49 and 50, Lines 1-35: Scheme designation "Scheme I" is missing.

Columns 51 and 52, Lines 15-45: Scheme designation "Scheme J" is missing.

Column 76, Line 23, Claim 16: "pound: (2,S,3S,5R)-4-[5-aminosulfonyl)-4-chloro-2-[(2-", should be --pound: (2S,3S,5R)-4-[5-(aminosulfonyl)-4-chloro-2-[(2- --

Signed and Sealed this
Thirteenth Day of March, 2012

David J. Kappos
*Director of the United States Patent and Trademark Office*

CERTIFICATE OF CORRECTION (continued)
U.S. Pat. No. 7,763,612 B2

Columns 61 and 62: structure should be

SCHEME M